(12) United States Patent
Biehler et al.

(10) Patent No.: US 12,357,775 B2
(45) Date of Patent: Jul. 15, 2025

(54) METHOD FOR ASSESSING THE EFFICACY OF AN AEROSOL FOR PULMONARY DRUG DELIVERY AS WELL AS INHALER DEVICE, ORALLY INHALED AND/OR NASAL DRUG PRODUCT AND DRUG/DEVICE COMBINATION PRODUCT

(71) Applicant: Ebenbuild GmbH, Munich (DE)

(72) Inventors: Jonas Biehler, Grafing b. Munich (DE); Karl-Robert Klaus Wichmann, Munich (DE); Kei Wieland Müller, Munich (DE); David Rudlstorfer, Munich (DE); Maximilian Josef Grill, Munich (DE); Jakob Richter, Munich (DE)

(73) Assignee: Ebenbuild GmbH, Munich (DE)

( * ) Notice: Subject to any disclaimer, the term of this patent is extended or adjusted under 35 U.S.C. 154(b) by 0 days.

(21) Appl. No.: 18/636,164

(22) Filed: Apr. 15, 2024

(65) Prior Publication Data

US 2024/0399078 A1 Dec. 5, 2024

(30) Foreign Application Priority Data

May 31, 2023 (DE) .................... 10 2023 114 221.6

(51) Int. Cl.
*A61M 15/06* (2006.01)
*A61M 15/00* (2006.01)
(Continued)

(52) U.S. Cl.
CPC ....... *A61M 15/0065* (2013.01); *G06T 1/0007* (2013.01); *G06T 7/00* (2013.01);
(Continued)

(58) Field of Classification Search
CPC ........ A61M 15/0065; A61M 2202/064; A61M 2205/3334; G06T 1/0007; G06T 2207/30061
(Continued)

(56) References Cited

U.S. PATENT DOCUMENTS

2023/0133374 A1  5/2023  Müller et al.

FOREIGN PATENT DOCUMENTS

CN  204797996 U  11/2015
EP  2255843 B1  8/2011
(Continued)

OTHER PUBLICATIONS

Hartung_2020 (A mechanistic framework for a priori phamacokinetic predictions of orally inhaled drugs, PLOS Computational Biology, 2020). (Year: 2020).*

(Continued)

*Primary Examiner* — Brian S Cook
(74) *Attorney, Agent, or Firm* — Bookoff McAndrews, PLLC

(57) ABSTRACT

The invention relates to systems and methods for assessing the efficacy of an aerosol for pulmonary drug delivery as well as to an inhaler device, an orally inhaled drug product and a drug/device combination product. An aerosol can be generated by an inhaler device and comprises aerosol particles containing an orally inhaled drug product. The method comprises the steps of providing a computational lung model and a computational particle transport and deposition model, computing a spatial particle deposition distribution of discrete particles based on a determined aerosol value of an aerosol parameter, computing an efficacy value of an efficacy parameter based on the spatial particle deposition (Continued)

Figure 1:
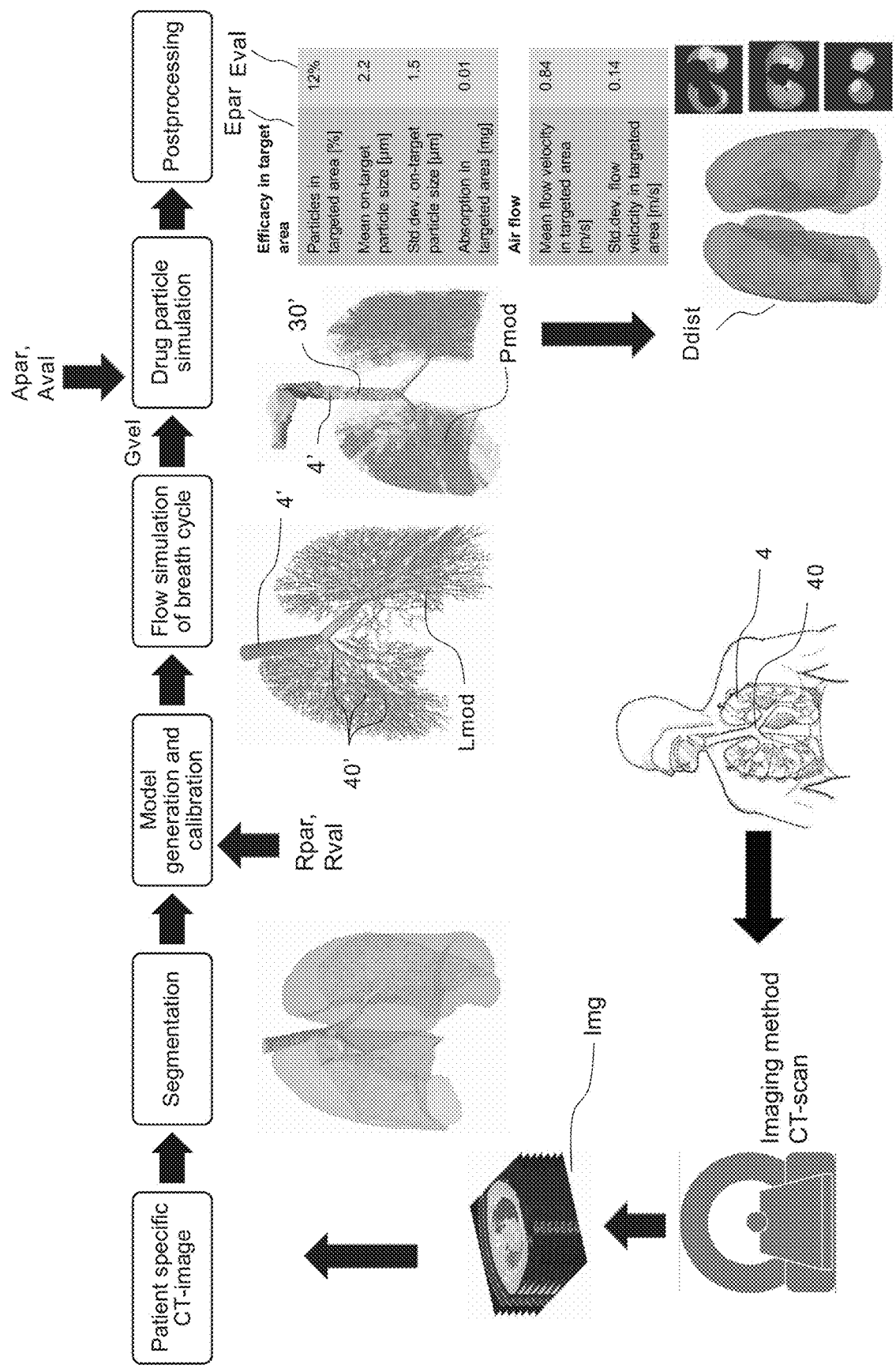

distribution and using the efficacy value for automatically assessing the efficacy for pulmonary drug delivery of the aerosol.

34 Claims, 19 Drawing Sheets

(51) Int. C

Figure 10g

METHOD FOR ASSESSING THE EFFICACY OF AN AEROSOL FOR PULMONARY DRUG DELIVERY AS WELL AS INHALER DEVICE, ORALLY INHALED AND/OR NASAL DRUG PRODUCT AND DRUG/DEVICE COMBINATION PRODUCT

CROSS-REFERENCE TO RELATED APPLICATION AND PRIORITY

This application claims the benefit of priority to German Application No. 10 2023 114 221.6, filed May 31, 2023, which is herein incorporated by reference in its entirety.

TECHNICAL FIELD

The invention relates to a method for assessing the efficacy of an aerosol for pulmonary drug delivery. Furthermore, the invention relates to an inhaler and/or ventilator device for administering orally inhaled and/or nasal drug products, to an orally inhaled and/or nasal drug product and to a drug/device combination product of such a drug product and such a device.

Moreover, the invention relates to assessing the efficacy of an orally inhaled and/or nasal drug product and of a drug/device combination product for pulmonary drug delivery as well as to assessing the performance of an inhaler and/or ventilator device for pulmonary drug delivery. The invention also relates to methods for generating an aerosol, designing and/or producing an inhaler and/or ventilator device and producing an orally inhaled and/or nasal drug product.

BACKGROUND

Drug delivery to the lungs (pulmonary drug delivery) is a favorable and important route of drug administration. The big crux, however, is that the delivered dose at the site of action in the lungs is unpredictable and even difficult to measure a posteriori. The delivered dose predominantly determines efficacy of pulmonary drug delivery.

Different types of inhaler devices are typically used for administering different kinds of orally inhaled drugs. Among other factors, the properties of the generated aerosol using the inhaler device significantly influence the transport of aerosol particles to the lungs and hence the efficacy of pulmonary drug delivery.

The local delivered drug dose is in practice unpredictable because aerosol transport and deposition depend on a variety of factors ranging from inhaler design and inhalation pattern over aerosol type to the constitution of patients. It can vary drastically, both between subjects and within the lungs, depending on lung morphology/physiology, and disease since lungs afflicted with diseases such as COPD or IPF no longer show a homogenous air distribution but rather exhibit strong regional differences. It is therefore desirable to provide orally inhaled drug products, inhaler devices and drug/device combination products that achieve a predictable efficacy of pulmonary drug delivery.

Numerous drug administration devices are currently available on the market to deliver medications into the lungs. The most common available inhaler devices can be separated into three main categories. Metered-dose inhalers (MDIs) comprise pressurized metered-dose inhalers (pMDIs) and breath-actuated metered-dose inhalers (BAMDIs). Dry powder inhalers (DPIs) comprise single-dose dry powder inhalers, multi-unit-dose dry powder inhalers and multi-dose dry powder inhalers. Soft-mist inhalers (SMIs) comprise vibrating mesh nebulizers (VMNs), jet nebulizers (JNs) and ultrasound nebulizers.

Metered-dose inhalers (MDIs) are widely used for the treatment of respiratory diseases such as asthma and chronic obstructive pulmonary disease (COPD). Due to their ease of use, portability and quick relief of respiratory symptoms, they are a popular choice. However, proper technique is essential for effective delivery of medication, and some patients may find it challenging to use MDIs correctly. Pressurized metered-dose inhalers (pMDIs) have a canister that contains a pressurized formulation of medication and a mouthpiece through which the medication is inhaled. The medication is released when the patient presses down on the canister, regardless of whether the patient is inhaling or not. The efficacy of medication delivery with MDIs can depend on the patient's coordination and ability to inhale at the right time. Breath activated metered-dose inhalers (BAMDIs), on the other hand, only release medication when the patient is actively inhaling. This removes the need for the patient's coordination when releasing the medication and simultaneously inhaling.

Dry powder inhalers (DPIs) are medical devices used to deliver drugs directly into the lungs. Unlike MDIs, which deliver the drug in the form of a mist, DPIs deliver the drug in a dry powder form. Furthermore, DPIs do not rely on the coordination of the patient due to only releasing drugs during inhalation which simplifies their use. On the downside the dosage of medication is not consistent due to small differences in each inhalation. Generally, three different types of DPIs are available. Single-dose DPIs contain a single dose of medication in a pre-measured capsule. During usage this capsule is punctured, the medication exits and the inhaler is discarded. Multi unit-dose DPIs contain multiple doses of medication which are punctured like single-dose DPIs. These inhalers are discarded once all dosages are consumed. Multi-dose DPIs contain a reservoir with medication which is measured at each use. Furthermore, the medication can be refilled after the inhaler is empty.

Soft-mist inhalers (SMIs), also called nebulizer inhalers, use a mechanical system to generate a mist which is inhaled by patients. Due to the mist generation not relying on the inhalation of the patient, SMIs are often used for patients which have difficulties using an MDI or a DPI. Downsides of SMIs include long treatment times, large unportable devices, the requirement of external energy sources, regular cleaning and maintenance and a high price of the device. Among soft-mist inhalers, vibrating mesh nebulizers (VMNs) use a vibrating mesh membrane to convert liquid medication into a fine mist which can be inhaled. They can be further grouped into actively and passively vibrating mesh nebulizers. Jet Nebulizers (JNs) use a high-pressure gas flow onto a liquid reservoir of medication. Due to the high flow rate and surface tension of the liquid it gets converted into small droplets. Too large droplets are deflected and get further nebulized by the jet of air before exiting the nebulizer. Further types of Jet nebulizers include open-vent nebulizers and breath-enhanced open-vent nebulizers. Ultrasound Nebulizers use a piezoelectric crystal to produce high-frequency vibrations that cause the liquid medication to form a fine mist which is inhaled by the patient.

Besides the three main categories, there are also other types of inhalers, such as spinning disk aerosol generators, Spinning top aerosol generators or Centrifugal aerosol generators. These types use a rapidly spinning disk with embedded grooves to produce aerosol particles from a medication reservoir. Due to the high rotational speed, and thereby resulting centrifugal force, the medication is forced into a thin film, broken into fine droplets and finally leave the spinning disk. The fine mist is then carried away by a stream of air.

Due to the geometric complexity of the (human) respiratory system including the lungs—in the following often simply referred to as the lungs-, experimental investigations using physical models of the lungs or parts thereof are only possible in overly simplified systems and even then, experiments are notoriously difficult to conduct. Suitable animal models are also difficult to develop and are associated with ethical and other disadvantages. In-vivo imaging of aerosol inhalation and deposition in human subjects is possible using modern nuclear imaging techniques such as radio scintigraphy or 3D SPECT imaging. However, those imaging modalities do have limited spatial and temporal resolution, amongst others, due to motion artefacts or depth-dependent spatial blurring. In addition, their use in susceptible populations is often not feasible or ethical.

In-silico modelling techniques for simulating the pulmonary system of a specific patient have been contemplated as an alternative and several computational approaches have been developed to approximate particle transport in human lungs. However, existing models are severely limited by morphological truncation, i.e., not encompassing the whole airway tree and spatial resolution. In addition, existing models do not account for lung tissue nor ribcage and diaphragm.

Before existing modeling approaches are discussed in more detail, it is important to clarify certain terminologies related to the spatial distribution and deposition of particles within the lungs. The relevant literature commonly uses the term 'regional' deposition within the lungs, which typically involves distinguishing between larger subdomains of the pulmonary system, such as the mouth-throat region, the tracheo-bronchial region, and the discrimination between lung lobes or certain airway generations (levels of bifurcation of the airway tree of the lungs). In contrast, the suggested modeling approach according to the invention can achieve a much higher resolution, predicting the precise trajectory of all particles across both space and time. Therefore, we use the term 'spatio-temporal' to refer to patterns in both space and time, and the term 'regional' to refer to different compartments and subdomains within the pulmonary system.

That being said, known modelling approaches for pulmonary drug delivery vary widely, depending on the specific application and purpose of the model. Historically, three approaches have dominated the simulation of drug delivery to the lungs. More specifically, the physical phenomena that govern particle transport and deposition can be encapsulated in a computational model by deriving the mathematical equations either empirically, heuristically, or from first principles, i.e., the physical laws that govern the particle transport within the lungs.

The so-called ICRP model (*The New ICRP Model for the Respiratory Tract*. Radiation Protection Dosimetry. 1994; 53 (1-4): 107-114. doi: 10.1093/rpd/53.1-4.107) is an example for an empirical model. Essentially, the model is comprised of a series of mathematical filter functions with empirically determined deposition fractions for different regions within the lung. Empirical models neglect the intricate geometric structure of the lungs, thus can neither account for patient-specific lung or airway geometry nor lung tissue damage in given subdomains.

Similarly, Trumpet models (see, Taulbee D B, Yu C P. *A theory of aerosol deposition in the human respiratory tract*. Journal of Applied Physiology. 1975; 38 (1): 77-85. doi: 10.1152/jappl.1975.38.1.77, Taulbee D B, Yu C P, Heyder J. *Aerosol transport in the human lung from analysis of single breaths*. Journal of Applied Physiology. 1978; 44 (5): 803-812. doi: 10.1152/jappl.1978.44.5.803, Robinson R J, Yu C P. *Deposition of Cigarette Smoke Particles in the Human Respiratory Tract*. Aerosol Science and Technology. 2001; 34 (2): 202-215. doi: 10.1080/027868201300034844) approximate the human airway system through a one-dimensional, variable cross-section channel. Particle transport and deposition are described by differential equations in a one-dimensional channel accounting for increasing generational airway volume but neglecting all internal structure of the lungs. While its simplicity and elegance are appealing, the crude geometric simplification of the trumpet model precludes its application to individual patients.

In contrast, heuristic models incorporate some information about the geometry of the airway tree. Hence, these models are also often referred to as morphometric models. Examples of this class of models are single-path (typical path) models (Human respiratory tract model for radiological protection. A report of a Task Group of the International Commission on Radiological Protection. Ann ICRP. 1994; 24 (1-3): 1-482.) or multiple path models, such as MPPD (Asgharian B, Hofmann W, Bergmann R. *Particle Deposition in a Multiple-Path Model of the Human Lung*. Aerosol Science and Technology. 2001; 34 (4): 332-339. doi: 10.1080/02786820119122).

Within these models, the computation of the distribution of the airflow within the lungs is not based on physical principles but rather heuristic assumption like flow splitting proportional to the distal lung volume supplied by either daughter airway. An assumption that is obviously violated in almost all cases where the conducting or respiratory airways are afflicted by disease and show pathologic abnormalities. In addition, these models are not well suited to model patient-specific drug transport and deposition. Thus, these models are only useful for investigations where the aim is a broad understanding of particle deposition phenomena within a large cohort of rather healthy lungs, since these models are unable to uncover specific deposited particle locations (e.g. hotspots) and cannot account for complex flow patterns within the airway system. Another limitation of these models is that they have been conceived for the deposition simulation of ambient particles which does not reflect the situation of spray aerosol inhalation.

On the other end of the spectrum are physics-based Computational Fluid Particle Dynamics (CFPD) models that are based on physics-based equations and actual or idealized patient-specific geometries.

EP 2 255 843 A1 describes such an approach where the geometry of the first few generations of the airways is extracted from a CT (Computed Tomography) scan, meshed, and then used as in input for a CFD simulation of the airflow in the first few generations (levels of bifurcation) of the airway tree. Such models are inherently limited to the larger generations of the conducting airways, typically the 6th to 7th generation because of the limited resolution of CT scans as well as the prohibitive computational costs required to conduct a fully resolved 3D CFPD simulation of the entire airway tree. Since this approach omits large portions of the conducting and respiratory airways as well as any tissue or structures surrounding the lungs. A particular disadvantage is, that estimation of outlet boundary conditions for the distal ends of the simulated part of the airway tree requires two CT scans. Using a CT scan at full inspiration and expiration, respectively, image-processing techniques are used to compute the lobar inflation across the breathing cycle. This data is then used to adjust outflow boundary conditions such that the lobar inflation in the model matches the measured lobar inflation. Moreover, lobar expansion is assumed to be uniform. Aside from the requiring at least two CT scans, the approach described in EP 2 255 843 A1 cannot revolve structures beyond the lobes. The model does not encompass smaller distal airways and neither the alveolar region nor the thorax are accounted for. The approach is not predictive in the sense that it cannot extrapolate beyond what was measured with the two CT scans, which are needed to calibrate the model. Another shortcoming of EP 2 255 843 A1 is that exhalation cannot be modelled. Deposition statistics can only be estimated under the assumption that all inhaled particles are deposited. Central to peripheral deposition is approximated by computing the fraction of particles deposited in the first few generations and the total number of seeded particles. Further regional information beyond the lobe-level or deposition statistics for higher generations cannot be computed. Since calibration of the model always requires a second CT, which limits the use cases of the approach to scenarios where two CT-scans are available and precludes the application in longitudinal studies where only routine data is available.

The concept of performing 3D CFD analysis can be extended beyond the airway generations that are visible in the CT-scan by augmenting the airway segmentation using morphological models of the higher generation airways (Kronbichler M, Fehn N, Munch P, et al. *A next-generation discontinuous Galerkin fluid dynamics solver with application to high-resolution lung airflow simulations*. In: Proceedings of the International Conference for High Performance Computing, Networking, Storage and Analysis. SC '21. Association for Computing Machinery; 2021:1-15. doi: 10.1145/3458817.3476171). However, resolving the structure and flow field in a three-dimensional fashion result in computational costs that can only be coped with in feasibility studies on very large High-Performance-Computing systems. Extending this approach to a 3D CFPD simulation by adding particle transport would further multiply the computational costs.

The method described in WO 2014/125059 A1 determines the respiratory condition and furthermore aims at optimizing its treatment by means of 3D CFD simulation. It is stated that the disclosed method was able to determine the patient specific lung dose as a function of the patient specific morphology, aerosol and device characteristics, and inhalation profiles. However, the modelling approach described in WO 2014/125059 A1 is the same as the one described in EP 2 255 843 A1, of course having the same limitations.

First, the structural model of the lungs is limited to geometric information that is extractable from high resolution image data. The airway model is thus limited to the larger airways that are discernable in a high-resolution CT scan. Second, neither the lung tissue nor other structures in the thorax are part of the model described in WO 2014/125059 A1. Therefore, the outflow boundary conditions, i.e., pressures at the bronchioli outlets for the 3D CFD simulations have to be adjusted such that the mass flow rate is identical to the mass flow rate obtained via at least two CT images. The requirement of two or more volumetric images for the construction of the model presents a major disadvantage in and by itself as it requires a special treatment or study protocols. These requirements expose the patient to a higher dose of radiation compared to the acquisition single volumetric images that are used in clinical routine. In addition, as exhalation cannot be simulated in WO 2014/125059 A1, the method described therein can only approximate the effective lung dose by assuming that all particles that are transported beyond the glottis during inhalation are deposited in the lungs.

By only including the upper part of the airway tree in the model while furthermore omitting lung tissue as well as surrounding structures, the lung model described in WO 2014/125059 A1 and the obtainable spatial resolution of the aerosol deposition pattern is very limited. Information beyond the lobar level cannot be obtained. This limited approach is also described in (De Backer J W, Vos W G, Vinchurkar S C, et al. *Validation of Computational Fluid Dynamics in CT-based Airway Models with SPECT/CT*. Radiology. 2010; 257 (3): 854-862. doi: 10.1148/radiol.10100322).

In summary, known approaches relying on 3D-CFD models do not encompass the entire airway tree. The airway tree is either truncated before the respiratory zone or only a few selected airway paths into the respiratory zone are modelled. A 3D-CFD simulation of the entire airway tree would cause prohibitive computational costs, even for scientific applications using high-performance computers, let alone for commercial applications.

A method for determining a patient-specific ventilation parameter for setting a ventilation machine by means of which the patient is to be ventilated is disclosed in WO 2021/204931 A1 based on a modelling approach for fluid and structural mechanics of the lungs. Neither particle transport in general, nor pulmonary drug delivery is considered therein.

None of the aforementioned methods is suited to assess the efficacy of pulmonary drug delivery throughout the entire lung of a human (or animal) subject. Furthermore, the known methods for predicting or evaluating pulmonary drug delivery suffer from low accuracy due to limited resolution and overly simplified modeling approaches. In particular, the effects of inhaler devices on the properties of the generated drug aerosol to be inhaled are not adequately accounted for in the prior art.

SUMMARY

An objective of the invention is overcoming at least one problem described with respect to the prior art. In particular assessing the efficacy of pulmonary drug delivery throughout the entire lung, preferably with increased accuracy and/or in shorter time, is one aim of the invention.

It is a further objective of the invention to make assessments of the efficacy of pulmonary drug delivery available for use in technical applications, such as assessing the performance of an inhaler device, assessing the efficacy and/or safety of an orally inhaled and/or nasal drug product, in particular of a dose of an active ingredient in the drug product, or assessing the efficacy of a drug/device combination product.

Another objective of the invention is providing a method for designing and/or producing an inhaler device for pulmonary drug delivery with improved efficacy and providing such an inhaler device.

It is also an objective of the invention to provide a method for operating an inhaler device such that it generates an aerosol having improved efficacy for pulmonary drug delivery.

Yet another objective of the invention is providing a method for producing an orally inhaled and/or nasal drug product with improved efficacy and/or safety and providing such a drug.

A further objective of the invention is providing a drug/device combination product of an orally inhaled and/or nasal drug product and an inhaler device for administering orally inhaled and/or nasal drug products with improved efficacy and/or safety.

In particular, the problem is solved by a method for assessing the efficacy of an aerosol for pulmonary drug delivery, wherein the aerosol comprises aerosol particles containing an orally inhaled and/or nasal drug product, comprising the following steps:
- determining at least one aerosol value of at least one aerosol parameter characterizing the aerosol, wherein in particular the aerosol is generated by an inhaler device, providing a computational lung model representing the structure of a, preferably human, respiratory system and transient gas flow in the airways of the respiratory system at least between the trachea and the lungs, in particular during inhalation and exhalation, wherein the computational lung model is based on a discretized respiratory-system structure derived from processed image data representing at least one, preferably human, respiratory system, wherein, preferably, the discretized respiratory-system structure is derived from processed image data of a single tomographic image of each of the at least one respiratory system;

providing a computational particle transport and deposition model representing transient transport of individual aerosol particles in the gas flow in the airways and deposition of individual aerosol particles in the respiratory system, computing a spatial particle deposition distribution of a plurality of discrete particles deposited in the discretized respiratory-system structure based on the at least one aerosol value using the computational lung model and the computational particle transport and deposition model;

computing at least one efficacy value of an efficacy parameter indicating efficacy of pulmonary drug delivery of the aerosol based on the spatial particle deposition distribution;

using the efficacy value for automatically assessing the efficacy for pulmonary drug delivery, storing the efficacy value in a storage device, displaying the efficacy value using a display device and/or transmitting the efficacy value for use in assessing the efficacy for pulmonary drug delivery.

The efficacy value may be used or made available for use (exclusively) in technical applications, such as (automatically) assessing the performance of an inhaler device for pulmonary drug delivery, assessing the efficacy and/or safety of an orally inhaled and/or nasal drug product, in particular of a dose of an active ingredient, or assessing the efficacy of a drug/device combination product for pulmonary drug delivery.

Further possible technical uses of the efficacy value comprise: designing and/or producing an inhaler device for pulmonary drug delivery, in particular choosing (setting/implementing) an inhaler design parameter, based on the efficacy value; operating an inhaler device for pulmonary drug delivery, in particular setting a device operation parameter of the inhaler device, based on the efficacy value; producing an orally inhaled and/or nasal drug product based on the efficacy value; producing or providing a drug/device combination product of an orally inhaled and/or nasal drug product and an inhaler device based on the efficacy value.

Orally inhaled and/or nasal drug products within the scope of the invention refer to drugs that are intended to be delivered to the lungs (pulmonary drug delivery). Typically, such drugs are administered to be inhaled through the mouth, but depending on the circumstances could (intentionally or unintentionally) be (partly) inhaled commonly through the mouth and the nose or (intentionally or unintentionally) only through the nose. For example, a patient may use an inhalation mask, e.g. of a nebulizing device, covering both mouth and nose for inhaling an aerosol of a drug that is typically referred to as an orally inhaled drug. Insofar, the invention predominantly refers to drugs that are (exclusively) inhaled orally. Accordingly, drugs administered to be inhaled through the nose and intended to be (predominantly) delivered (only) to the nose (but not to the lungs), in particular to be absorbed by the nasal mucous membrane, such as nasal sprays, are not comprised by orally inhaled and/or nasal drug products in the sense of the invention.

Furthermore, orally inhaled and/or nasal drug products can be inhaled actively, i.e. by spontaneous breathing of an individual (healthy person or patient), or passively, i.e. by artificial respiration of a patient, in particular using artificial (mechanical) ventilation. Any mixed form of active and passive breathing, such as assisted spontaneous breathing, is included. Accordingly, the term "inhaler device" refers to any device suited to provide an aerosol for pulmonary drug delivery, irrespective whether drug deliver to the lungs is caused by active or passive inhalation.

The efficacy of pulmonary drug delivery can be assessed for, but not limited to, drugs administered to treat lung diseases such as asthma, chronic obstructive pulmonary disease (COPD) or idiopathic pulmonary fibrosis (IPF), in particular to treat (local) tissue-level pathologies such as emphysema or fibrosis, in particular inflammation of lung tissue. Further drugs can be administered to treat pulmonary arterial hypertension (PAH), respiratory distress syndrome (RDS) or infective diseases. The efficacy of pulmonary drug delivery can also be assessed for cannabis as a drug.

Active ingredients in orally inhaled and/or nasal drug products can comprise, but are not limited to, inhaled bronchodilators to treat obstructive airway diseases such as asthma and COPD, anti-inflammatory products including gluococorticoids to treat inflammation of lung tissue, anti-infectives to treat infective diseases, recombinant human deoxyribonuclease (rhDNase) for treatment of cystic fibrosis, mannitol in treatment of bronchiectasis and cystic fibrosis, prostacyclins utilized for pulmonary arterial hypertension (PAH) or lung surfactant for treating respiratory distress syndrome (RDS). Drug products can also be intended for systemic therapies not restricted to pure respiratory diseases, including active ingredients such as Nicotine or Loxapine. Also THC can be an active ingredient, in particular of orally inhaled drug products containing or being cannabis.

An aerosol can be understood as a mixture of solid or/and liquid particles (suspended particles) and a carrier gas. The carrier gas can be or comprise air and/or a different gas, in particular oxygen and/or helium. A carrier gas can be a mixture of different gases, in particular air oxygen and/or helium. An aerosol with solid particles may be generated from a powder. An aerosol with liquid particles in the form of droplets may be generated by nebulizing a liquid.

An aerosol parameter can be understood as a parameter characterizing an aerosol, preferably by indicating one or more physical properties of an aerosol, in particular physical properties of the particles or the carrier gas comprised by the aerosol or of the aerosol (as a whole).

Assessing the efficacy for pulmonary drug delivery can mean predicting, monitoring and/or evaluating the efficacy of an orally inhaled and/or nasal drug, which could be administered to a (human or animal) body theoretically or in the future, or has been administered to a (human or animal) body in the past. However, methods according to the invention are no therapeutic methods for treatment of the human or animal body. A step of actually administering a drug to human or animal are not comprised by the methods described.

An efficacy parameter indicating efficacy of pulmonary drug delivery of an aerosol can indicate how well the aerosol is suited for pulmonary drug delivery, in particular with respect to the quantity of the aerosol particles delivered to (deposited in) the lung and/or the area (location, zone and/or airway generation) in which the aerosol particles deposit in the lung (spatial particle deposition distribution), in particular an active ingredient of the drug contained in the aerosol particles. In particular, the efficacy parameter can indicate a quantity and/or ratio of a drug (active ingredient) delivered to at least one, preferably specific, area(s) in the lung, such as location(s) in the airways, left/right lung, pulmonary lobe(s), and/or airway generation(s), etc. Further, the efficacy parameter can indicate a quantity and/or ratio of a drug (active ingredient) reaching the blood circulation and/or the lung tissue through the lung.

The processed image data representing at least one respiratory system is preferably obtained from an imaging (tomographic) method applied to a (human or animal) respiratory system, in particular to the lungs, in a (real) body of a healthy (human or animal) individual or to a (human or animal) patient, in particular a patient having a lung disease. Preferably, the discretized respiratory-system structure is derived from processed image data of (only) a single, preferably tomographic, image of each of the at least one (real) respiratory system. In particular, the single (tomographic) image represents (only) one state (inhaled, exhaled or in between) of the respiratory system, preferably at (only) one point in time. The processed image data can represent (exactly) one (real) respiratory system or a (averaged) plurality of (real) respiratory systems, preferably of different individuals. The processed image data can represent a (single) real respiratory system or a (single) virtual (averaged and/or modified) respiratory system. The processed image data can represent (parts of) a healthy and/or (parts of) a pathological respiratory system.

Transient (time-dependent) gas flow in the airways in particular refers to (laminar and/or turbulent) flow of gas (air and/or carrier gas) in the airways during inhalation and/or exhalation. Particle transport in particular refers to the (passive) transport (motion) of a (solid or liquid) aerosol particle in the gas flow, in particular due to the forces of the gas flow acting on the particle.

A drug/device combination product can be understood as a medicinal product containing both a drug product, in particular containing a specific dose of a drug, and a medical device for administering the drug. In the context of this disclosure, a drug/device combination product for pulmonary drug delivery contains an orally inhaled and/or nasal drug product and an inhaler device for administering the orally inhaled and/or nasal drug product. In particular the efficacy of the drug/device combination product for pulmonary drug delivery in combination depends on both the efficacy (and/or safety) of the drug product and the performance of the inhaler device.

At least some, preferably all, steps can be carried out using a computer (computer-implemented method). In particular method steps containing computations can be carried out by at least one processor. In particular method steps providing computational models can use at least one storage medium and/or database providing the computational model.

The method has the advantage that the efficacy of pulmonary drug delivery can be assessed throughout the (entire) lung. This is achieved by considering transport and deposition of individual aerosol particles throughout the (entire) lung throughout inhalation and exhalation. Moreover, using a single (tomographic) image of a respiratory system of an individual (patient), reduces the dose of radiation the individual is exposed to. This comprehensive approach results in increased accuracy of the obtained spatial particle deposition distribution. As a result, a more precise and reliable prediction and/or evaluation of drug delivery to the lung is possible, in particular of targeted drug delivery to specific areas of the lung. The local aerosol deposition and quantification of the delivered drug dose at any desired site of action in the (entire) lung can be accurately evaluated and/or predicted, in particular for a specific individual (patient-specific).

In embodiments of the method, the at least one aerosol parameter is indicative of one or more of a particle size, preferably a mean particle size, a particle size distribution, a particle density, a particle shape, preferably a mean particle shape, an aerosol flow, which is preferably time-dependent, in particular relative to a respiration cycle, a flow velocity of the aerosol, a type of carrier gas and a pressure of a carrier gas of the aerosol. An aerosol parameter can constitute a set of a plurality of individual aerosol parameters, which commonly characterize the aerosol.

Normally, homogeneous aerosol parameters (particle size, particle density, particle volume, particle shape, particle velocity, etc.) within an aerosol are not technically achievable in physical reality. In practice, aerosol parameters (particle size, etc.) are typically subject to a distribution (size distribution, etc., usually a log-normal distribution). Insofar, an aerosol value of an aerosol parameter (particle size, etc.) for an aerosol particle can be understood as the value of those particles of the distribution (size distribution, etc.) with the highest probability or a (narrow) range of the distribution around the value with the highest probability.

The particle size can be understood as an equivalent particle size, for example of a droplet (liquid) or of a solid particle, e.g. from a powder. The particle size can be a (mean) particle diameter, in particular of (spherical) droplets, or of the equivalent diameters of solid particles of different shapes, in particular from a powder. The particle size distribution is preferably a log-normal distribution, preferably described by mass median aerodynamic diameter and/or geometric standard deviation. A log-normal distribution can be understood as a continuous probability distribution of a random variable (e.g. particle diameter), whose logarithm is normally distributed. Particle sizes for aerosols generated by nebulizing devices, for example, can be determined according to DIN EN 13544-1. The particle density can be a (averaged) number of particles contained per aerosol volume. Particle size (particle size distribution) and particle density belong to the most relevant parameters determining particle transport within the lungs.

An aerosol flow can be an aerosol mass flow or an aerosol volume flow, preferably time-dependent relative to a (human) respiration cycle. The pressure of the carrier gas as an aerosol parameter can be time-dependent. A flow velocity of the aerosol or a particle (mean) velocity can be defined at a specific point along the aerosol flow path, preferably at the inlet of the trachea and/or at the outlet of an inhaler device.

A carrier gas preferably contains of air, helium, oxygen or a mixture thereof. An aerosol parameter characterizing the (carrier gas of an) aerosol can be a density, composition and/or molecular weight of the carrier gas. The type of carrier gas of the aerosol has an effect on particle transport in the lungs, in particular the relation between the density of the carrier gas and the density of the aerosol particles.

In addition to the above mentioned aerosol parameters, further aerosol parameters can comprise, but are not limited to, particle (surface) charge, particle hydrophobicity and/or particle binding affinity. An aerosol parameter can indicate the quantity of active ingredient of the drug contained in a particle, in particular a quantity of active ingredient per particle volume.

In embodiments of the method, the at least one aerosol value is determined by

- measuring the aerosol value,
- obtaining the aerosol value from a database containing data indicating physical properties of the aerosol,
- obtaining or deriving the aerosol value from specification data of an inhaler device,
- computing the aerosol value based on analytical relations of physical properties of the aerosol, and/or
- computing the aerosol value, in particular as a result of a computational simulation of a generation process and/or flow of the aerosol, in particular in an inhaler device, preferably using a computational inhaler device model.

Aerosol values of aerosol parameters can be measured (in experiments), obtained (from a database) and/or computed (analytically or in computer simulations) prior to carrying out the method for assessing the efficacy of the aerosol for pulmonary drug delivery, possibly stored (buffered), and subsequently used as input aerosol values for the method. Data obtained from a database can be (previously) measured or previously computed (pre-computed) data. The determined aerosol values can be a combination of measured, computed and otherwise obtained aerosol values.

In one embodiment, the method further comprises a step of determining at least one respiration value of a respiration parameter characterizing respiration of the respiratory system, in particular spontaneous breathing, assisted spontaneous breathing and/or artificial respiration, wherein the respiration value defines a boundary condition of the computational lung model. Preferably, the respiration parameter is one or more of

- a, preferably time-dependent, pressure difference, preferably between a pleural space and the trachea,
- a, preferably time-dependent, inhalation and/or exhalation gas flow,
- a minimum and/or maximum lung pressure value and a respiration cycle frequency value, in particular for pressure-controlled artificial respiration, and
- an inhalation and/or exhalation gas volume, in particular for volume-controlled artificial respiration.

A respiration parameter can be a breathing curve indicating individual (patient-specific) respiration over time, such as an (individual) inhalation and/or exhalation gas flow, an (individual) lung volume or an (individual) lung pressure over time, preferably over at least one (full) respiration cycle (respiration time interval over inhalation and exhalation). A breathing curve can refer to spontaneous breathing, assisted spontaneous breathing and/or artificial respiration. The breathing curve, particularly the (sequence of) respiration value(s), can be used to calibrate the computational lung model, in particular to determine (all) necessary boundary conditions for the computational lung model. Preferably, the (measured) breathing curve is matched (synchronized) with the lung state in which the tomographic image was made (e.g. full inhalation or full exhalation) for calibrating the computational lung model.

Respiration value(s), in particular a sequence of respiration values representing a (discrete) breathing curve, can be derived (optionally using additional calculations and/or parameters) from a measured individual (patient-specific), time-dependent breathing curve, preferably over a full respiration cycle. A respiration value can be derived based on a measured, preferably time-dependent, inhalation and/or exhalation (respiration cycle: inhalation and exhalation) gas flow and/or lung volume of an individual (patient). One or more respiration value(s) of a respiration parameter can be determined or derived based on at least one measurement, for example using a spirometer.

In a preferred embodiment, a respiration value is derived based on a time-dependent inhalation and exhalation gas volume flow (v(t) [ml/s]), measured for the individual (patient) to whom the (tomographic image of the) respiratory system belongs. Preferably, the measurement (e.g. measurement of a breathing curve v(t)) is carried out using a spirometer. Generally, a spirometer is a known medical apparatus for measuring the volume of air (gas) inspired and expired by the lungs. A respiration value can be a tidal lung volume (e.g. in liters [l] or milliliters [ml]), indicating a volume difference ($\Delta V$ [ml]) between a (fully) exhaled and a (fully) inhaled state of the lung (i.e., tidal volume [ml]). A (tidal) lung volume can be derived from a measured inhaled and/or exhaled gas flow, e.g. by integration over time. The respiration value can be determined or derived based on previously recorded (pre-recorded) measured respiration data representing an inhaled and/or exhaled gas flow, particularly over a (full) respiration cycle, of an individual (patient-specific measured respiration data). In an alternative embodiment, a respiration value could be derived based on at least on measured lung pressure (pressure curve p(t)), in particular based on a minimum lung pressure value (fully exhaled lung state) and a maximum lung pressure value (fully inhaled lung state). A respiration value can also be based on a combination of measured gas volume flow(s) and measured lung pressure(s).

A pressure difference, in particular between a pleural space and the trachea, can be derived (calculated) based on measured values, in particular based on a measured time-dependent inhalation and/or exhalation gas flow and/or lung volume, and prescribed as a boundary condition for the lung model. A derived (calculated) pressure difference can correspond to a measured gas flow. A respiration value characterizing artificial respiration can refer to pressure-controlled (applied pressure-time curve) or volume-controlled (applied flow-time curve) artificial respiration.

Based on the respiration value(s), in particular the (time-dependent) boundary conditions derived therefrom, the computational lung model is preferably able to represent gas flow in the airways during both inhalation and exhalation, in particular based on (only) a single (tomographic) image of a respiratory system in combination with at least one, preferably measured, respiration value characterizing respiration of the respiratory system.

In one embodiment of the method, the discretized respiratory-system structure is based on a spatial segmentation of the structure of the, preferably conductive, airways of the respiratory system into a plurality of discrete, preferably spatially three-dimensional, more preferably tubular, airway segments and preferably a time discretization of time steps. Preferably, the gas flow velocity within at least a part of the airway segments is constant for each time step.

A (3D) air segment preferably comprises a (tubular) airway wall (hollow cylinder), preferably straight in axial direction and/or with axis-symmetric cross-section. The cross-section within each way segment can be constant (straight-cylinder airway segment) or decreasing (conical airway segment) in the downstream (inhaling) direction. Preferably, the discretized respiratory-system structure represents the (entire) airway tree of the (human) lung, preferably comprising at least the (conductive) airways downwards from the trachea, optionally further comprising the regions of the mouth, pharynx and/or larynx. Such a discretized respiratory-system structure adequately models the anatomical structure of the airways of the (human) lung. Typically, medical literature distinguishes 23 airway generations of the human lung. Within the conductive airways, each generation corresponds to a level of bifurcation of the airways (i.e., n levels of airway bifurcation correspond to n+1 airway generations).

The gas flow velocity can be modelled as a three-dimensional (3D-flow) discretized velocity field in some airway segments, preferably in lower airway generations (e.g. in generations 0, 0-1 or 0-2), and as a reduced-dimensional, preferably zero-dimensional (0D-flow, scalar velocity value), discretized velocity field in other airway segments, preferably in high airway generations (e.g. in generations higher than 0, 1 or 2). It is possible to compute a (computationally expensive) 3D-CFD simulation for low (the first few) airway generations and compute a (computationally cheaper) 0D-simulation for higher airway generations (up to the last structurally resolved airway generation). In a preferred embodiment, the gas flow velocity within all airway segments of the discretized respiratory-system structure is constant for each time step. Modelling (setting) the gas flow velocity constant within airway segments when computing the spatial particle deposition distribution, results in reduced computational cost.

In one embodiment of the method, the computational lung model represents the structure of at least six, preferably at least eight, more preferably at least ten, more preferably at least twelve generations of the airways. Preferably, the computational lung model further represents the mouth, the pharynx and/or the larynx and preferably further represents the alveoli of the lungs. Preferably, the computational lung model represents transient gas flow in the airways between the mouth and the lungs, in particular between the mouth and the alveoli of the lungs. Preferably, the computational lung model represents a closed volume of the airways and/or the computational lung model represents structural elasticity of the airways, in particular structural elasticity of airway walls and/or structural elasticity of lung tissue. Preferably, the computational lung model additionally represents the diaphragm and/or the thorax (ribcage), in particular by applying a, preferably volume-dependent, force on the (discretized respiratory-system structure of the) lung as a boundary condition.

Since the computational lung model can represent resilience (mechanical reaction force due to elasticity) of the airway walls and/or lung tissue and resolves and/or models the airways of the (entire) lung, meaning that the discretized airways incorporate a closed volume in which aerosol particles are transported, it also (automatically) accounts for exhalation, in particular of exhalation of previously inhaled aerosol particles.

Computational lung models of the prior art, however, are unable to account for exhalation of aerosol particles. In particular the computational lung model in EP 2 255 843 A1, due to truncation of structural resolution of the airways at a relatively low airway generation, does not encompass smaller distal airways and the alveolar region. Therefore, the lung model represents an open volume of the airways (open at the outflow in inhalation direction), meaning that exhalation of previously inhaled aerosol particles cannot be accounted for in EP 2 255 843 A1. Inhaled particles reaching the last results generation of airways leave the computational domain and are "lost".

In one embodiment of the method, the computational lung model is based on a discretized individual respiratory-system structure derived from processed image data representing an individual respiratory system, preferably of a healthy individual or a patient suffering from a lung disease. A computational lung model can represent an individual (patient-specific) respiratory system of a real individual (patient). In a preferred embodiment, the computational lung model is based on a discretized patient-specific respiratory-system structure derived from processed image data representing an individual pathological respiratory system of a patient suffering from a lung disease. Such a lung model can be used to assess the efficacy of pulmonary drug delivery for this individual patient.

In another embodiment of the method, the computational lung model is based on a discretized averaged respiratory-system structure derived from, preferably averaged, processed image data representing an average of a plurality of, preferably individual, respiratory systems, preferably of at least one healthy individual and/or at least one patient suffering from a lung disease. Processed image data of a plurality of single (tomographic) images of different respiratory systems, i.e. from different individuals, can be averaged, preferably using an image-data averaging algorithm, to obtain averaged processed image data. A discretized averaged respiratory-system structure representing a (virtual) averaged respiratory system can then be derived based on averaged processed image data.

If the computational lung model represents an averaged healthy lung (derived from a plurality of images of different healthy lungs), the model can be used to assess the (potential) efficacy of pulmonary drug delivery in a comparative study of a normal (average) healthy lung. If the computational lung model represents an averaged pathological lung (derived from a plurality of images of different pathological lungs), the model can be used to assess the (potential) efficacy of pulmonary drug delivery in a representative study of a typical (average) pathological lung. Such studies could significantly accelerate and/or reduced cost of medical admission procedures for orally inhaled and/or nasal drug products, for example by applying the method to a digital cohort of persons represented by corresponding computational lung models.

In one embodiment of the method, the computational lung model is based on a discretized respiratory-system structure derived from processed image data representing at least one healthy respiratory system and at least one predetermined pathological image-data pattern representing a, preferably local, pathological modification of at least one zone of the respiratory system caused by a lung disease. The processed image data can represent (parts of) at least one healthy and/or (parts of) at least one pathological respiratory system. In particular, individual or averaged processed image data can be modified by an image-data modification algorithm using at least one predetermined pathological image-data pattern.

A predetermined pathological image-data pattern can represent typical pathological changes of a (tomographic) image of a normal (healthy) lung caused by a specific lung disease and identifiable in (tomographic) images as a pathological pattern. Such pathological changes can be local changes of the airways (altered airway diameter) or of the lung tissue (pathologic tissue), for example, which can typically be observed in (tomographic) images of patients having a specific lung disease.

A pathological image-data pattern can be an instance (data set) of (tomographic) image data representing a (local) section of a (tomographic) image (locally) showing a pathological pattern. An image-data modification algorithm can modify image data, in particular averaged processed image data, using the pathological image-data pattern, e.g. by adding the pathological image-data pattern as a data sub set and/or by replacing a part of the averaged processed image data by the pathological image-data pattern (data sub set). A predetermined pathological image-data pattern can be obtained from a database storing a plurality of different typical pathological image-data patterns, preferably collected for various different types of patients (lung disease, individual medical record, age, gender, habits, lung volume, received pre-treatments, other non-lung specific drugs, etc.).

Alternatively, a pathological image-data pattern can be an instance (data set) of structural data representing a (pathological section of a) discretized respiratory-system structure extracted (as a data sub set) from a discretized averaged respiratory-system structure, which has been derived from averaged processed image data representing an average of a plurality of respiratory systems of a plurality of patients suffering from a specific lung disease. Thus, instead of modifying the (averaged) image data and deriving a (locally) modified discretized respiratory-system structure therefrom, also the derived discretized respiratory-system structure can be (locally) modified according to the (local) pathological change.

If the computational lung model represents an individual healthy lung and is modified based on a lung model of an averaged pathological lung, the model can be used to assess the (potential) efficacy of pulmonary drug delivery for a specific (healthy) person, in case the corresponding individual person gets the corresponding lung disease. If the computational lung model represents an averaged individual healthy lung and is modified based on a lung model of an average pathological lung, the model can be used to assess the (potential) efficacy of pulmonary drug delivery, in case a general healthy individuals get the corresponding lung disease. Such studies could significantly accelerate and/or reduced cost of medical admission procedures for orally inhaled and/or nasal drug products, for example by applying the method to a digital cohort of persons represented by corresponding computational lung models.

In one embodiment of the method, the computational particle transport and deposition model implements a Lagrangian approach to tracking individual discrete particles transported in the gas flow, in particular based on modelling at least one physical force acting on each individual discrete particle, in particular a gravitational force, a flow resistance force, a buoyancy force and/or a Brownian motion force. In particular, the transient motion (dynamic) and deposition of each individual discrete particle is tracked individually, particularly within each airway segment, preferably throughout inhalation and exhalation. The implemented Lagrangian approach is preferably a one-way coupled approach, meaning that the effect of the transient gas flow in the airways on the particles is considered, but not vice versa. In particular, the direction of the gravitational force in the computational particle transport and deposition model is set depending on the spatial, preferably vertical or horizontal, orientation of the respiratory system represented by the processed image data. A spatial orientation of the respiratory system preferably corresponds to an upright-sitting (vertical) position or lying-down (horizontal) position of an individual, in particular patient. Different directions of the gravitational force can be applied to assess the effect on pulmonary drug delivery on upright inhalation (and exhalation) compared to inhalation (and exhalation) while lying down. The flow resistance force is preferably computed based on the density and/or the viscosity of a predetermined type of carrier gas, preferably air, helium or oxygen, of the aerosol. The buoyancy force is preferably computed based on differing densities of the aerosol particle and the carrier gas. The Brownian motion force is preferably computed based on randomly generated velocity fluctuations, in particular if a discrete particle is located within an alveolar zone of the discretized respiratory-system structure. The implemented Lagrangian approach enables tracking of individual aerosol particles at any location in the entire airway tree and in the lung tissue, throughout inhalation and exhalation. Hence, more accurate, in particular also local, spatial particle deposition distributions taking into account (all) individual particles within the computational domain can be computed.

In one embodiment of the method, a discretized particle transport velocity field, in particular within a spatially three-dimensional airway segment, has a higher spatial dimension than a discretized gas flow velocity field, in particular within the spatially three-dimensional airway segment, at least within a part of the discretized respiratory-system structure, preferably within airway segments belonging to at least a second, more preferably at least a third, generation of the airways represented by the computational lung model. Preferably, a three-dimensional (3D-flow) discretized particle transport velocity field within a (each) spatially three-dimensional airway segment is computed (reconstructed) based on a constant (0D-flow) discretized gas flow velocity within a (each) spatially three-dimensional airway segment, at least within a part of the discretized respiratory-system structure, preferably in the entire discretized respiratory-system. Particularly, the discretized particle transport velocity field is used as input (one-way coupled approach) for the computational particle transport and deposition model. The discretized gas flow velocity field can be obtained from the computational lung model. Using a reduced dimensional approach for the gas velocity field, reduces computational cost, particularly saving computational resources for improving the spatial resolution of the airway tree. Overall, tracking individual particles throughout the entire elementary becomes possible while the transient gas flow is still resolved sufficiently.

In one embodiment of the method, the computational particle transport and deposition model tracks individual discrete particles within a spatially three-dimensional airway segment by applying a, preferably three-dimensional, particle transport velocity vector as the velocity of a particle. The particle transport velocity vector is preferably computed based on a predetermined three-dimensional velocity profile across the cross-section of the airway segment and a, preferably constant, gas flow velocity obtained from the computational lung model for the airway segment. The gas velocity field is preferably (spatially) constant within an (each) airway segment and, in particular, discontinuous between adjacent airway segments. Preferably, a normalized velocity profile corresponding to laminar flow (Poiseuille flow, particularly parabolic) or turbulent flow, particularly taking into account turbulent boundary layer at the airway walls, is multiplied by the (constant) gas velocity.

In one embodiment, the method further comprises a step of seeding individual discrete particles into the gas flow in the airways comprising
- assigning a seeding location in an inflow cross-section of the discretized respiratory-system structure, preferably in an inflow cross-section of the trachea, to each individual discrete particle, and/or
- assigning a seeding time to each individual discrete particle based on a determined aerosol flow, which is preferably time-dependent, in particular relative to a respiration cycle.

Seeding individual discrete particles preferably further comprises assigning one or more of a seeding velocity, seeding acceleration, particle density, particle size, particle shape, particle mass and drag coefficient to each individual discrete particle. The seeding location is preferably determined based on
- obtaining or deriving a statistical spatial distribution of aerosol particles in the aerosol, preferably based on measured, pre-computed and/or randomly generated aerosol particle distribution data,
- computing a particle location of the individual discrete particle in a computational simulation of a generation process and/or flow of the aerosol, in particular in an inhaler device, preferably using a computational inhaler device model, and/or
- measuring a spatial distribution of aerosol particles in the aerosol.

Seeding of individual discrete particles can be based on the condition of an equal spatial distribution across an inflow cross section (of the trachea) averaged over time. A seeding time is preferably a seeding time step, preferably derived from a predetermined seeding frequency or obtained from a predetermined sequence of seeding time steps. A computed seeding location can be the result of a particle location as output of a 3D-CFPD simulation of at least one generation of the (larger, i.e. upper) airways, preferably of the trachea. Particularly the particle location of an individual discrete particle as a result of a 3D-CFPD simulation of a first (lower) generation of airways can be assigned as a seeding location in an inflow cross-section of a second, preferably next, (higher) generation of the (still rather large) airways of the discretized respiratory-system structure. In particular, a particle location as result of a 3D-CFPD simulation of an upper section of the (larger) airways is used as input for a 0D-particle simulation in the (remaining) lower section of the (smaller) airways.

In one embodiment of the method, the computational particle transport and deposition model determines the flow path of an individual discrete particle across an airway bifurcation, preferably during exhalation and/or inhalation, by assigning the particle to one downstream airway segment based on evaluating at least one geometric bifurcation criterion. A geometric bifurcation criterion is preferably based on a geometric relation between an outflow cross-section of an upstream airway segment and an inflow cross-section of a downstream airway segment. Preferably, a geometric bifurcation criterion is evaluated based on a location of the particle, in particular a radial and/or a circumferential location in an outflow cross-section of an upstream airway segment.

An airway bifurcation particularly comprises one upstream airway segment and two downstream airway segments. In the inhalation flow direction of a respiratory system, an airway bifurcation comprises one upstream airway segment and two downstream airway segments branching off therefrom. In the exhalation flow direction of a respiratory system, an airway bifurcation comprises two upstream airway segments joining into one downstream airway segment.

Evaluating a (purely) geometric bifurcation criterion requires little computational time. In particular during exhalation (reverse bifurcation transfer), using a geometric bifurcation criterion can be sufficient, since the flow path of particles across a bifurcation leads into a common downstream airway segment. Only the radial and circumferential location of the particle remains to be determined based on the geometric criterion.

In one embodiment of the method, the computational particle transport and deposition model determines the flow path of an individual discrete particle across an airway bifurcation, preferably during inhalation, using at least one pre-computed airway bifurcation scenario. Preferably, each pre-computed airway bifurcation scenario is based on an evaluation of at least one previously performed higher-dimensional, preferably three-dimensional, simulation of particle transport in the gas flow across an airway bifurcation. The at least one pre-computed airway bifurcation scenario is preferably obtained from an airway bifurcation library, preferably storing a plurality of different pre-computed airway bifurcation scenarios.

A pre-computed inhalation airway bifurcation scenario may assign a particle in an upstream airway segment of an airway bifurcation to one of two downstream airway segments of the airway bifurcation, in particular to a specific cross-sectional location in an inflow cross-section of the downstream airway segment. A pre-computed exhalation airway bifurcation scenario may assign a discrete particle in one of two upstream airway segments of an airway bifurcation to a downstream airway segment of the airway bifurcation and assigns a specific cross-sectional location in an inflow cross-section of the downstream airway segment to the discrete particle.

The method may comprise a step of interpolating between more than one, preferably two, pre-computed airway bifurcation scenarios. Particularly, the flow path of an individual discrete particle across an airway bifurcation having a specific bifurcation geometry, preferably a specific bifurcation angle, may be derived from an interpolation of at least two (preferably two) pre-computed airway bifurcation scenarios having different bifurcation geometries, preferably different bifurcation angles. The interpolation of pre-computed airway bifurcation scenarios is preferably based on an interpolation of at least two (preferably two) bifurcation geometry parameters and a corresponding interpolation of at least two (preferably two) cross-sectional locations in an inflow cross-section of the downstream airway segment.

A pre-computed bifurcation scenario is preferably used as an alternative to a (purely) geometric bifurcation criterion, but could also be used in addition. Pre-computed bifurcation scenarios can be based on relatively complex pre-computed three-dimensional fluid flow/particle transport simulations (3D-CFPD: 3D Computational Fluid and Particle Dynamics) across bifurcations at high spatial and temporal resolution, preferably taking account turbulent flow, in particular, depending on a specific (type of) geometry of the bifurcation. Using pre-computed bifurcation scenarios allows for computing a spatial particle deposition distribution accurately although (only) a reduced dimensional (OD-flow) gas velocity field is used. The flow path of an individual particle across a bifurcation, particularly during inhalation, can be predicted accurately, in particular with similar accuracy as in a 3D-CFD simulation at reduced computational cost.

In one embodiment, preferably the previous embodiment, a pre-computed airway bifurcation scenario predicts the transport of a discrete particle across an airway bifurcation based on a classified type of bifurcation geometry of the airway bifurcation and/or based on a location of the discrete particle in an upstream airway segment, preferably in a radial sector and/or in a circumferential sector of the upstream airway segment. Preferably, a pre-computed airway bifurcation scenario assigns a cross-sectional location in an inflow cross-section of a downstream airway segment to the discrete particle.

In one embodiment, preferably one of the previous two embodiments, for determining the flow path of an individual discrete particle across a specific airway bifurcation, a suited pre-computed airway bifurcation scenario is selected, preferably from an airway bifurcation library, based on at least one or more of: a, preferably radial and/or circumferential, location of the discrete particle in an upstream airway segment, at least one geometrical parameter indicative of the bifurcation geometry of the airway bifurcation, a particle size of the discrete particle, a particle density in the zone of the airway bifurcation, and a particle velocity upstream of the airway bifurcation.

The geometrical parameter is preferably one or more of: a bifurcation angle between two downstream airway segments, a rotational orientation of one or more downstream segments about a central axis of an upstream airway segment and/or a flow deviation angle between a central axis of an upstream airway segment and a middle axis between two downstream airway segments.

In one embodiment of the method, the computational particle transport and deposition model determines deposition of a discrete particle based on evaluating at least one deposition criterion, wherein evaluating the deposition criterion preferably comprises at least one or more of: evaluating if a computed distance value of the discrete particle to an airway wall of an airway segment is equal to or less than a predetermined deposition distance, evaluating if a computed particle velocity of the discrete particle is equal to or less than a predetermined minimum velocity, and/or evaluating if a computed impact angle between the flow path of the discrete particle and an airway wall of an airway segment exceeds a predetermined minimum angle, which is preferably at least 45°, more preferably at least 60%, more preferably at least 75°. Optionally, a deposition criterion depends on the shape of the discrete particle and/or attraction forces between the discrete particle and the airway segment. Two or more of the described deposition criteria can be combined. Deposition criterion is used to determine whether, where and when an individual particle deposits within an airway segment. Computing the (all) location(s) of (all) deposited particles based on evaluating at least one deposition criterion is the basis for computing the spatial article deposition distribution.

In one embodiment of the method, the step of determining at least one aerosol value uses a computational inhaler device model representing a generation process and/or a flow of an aerosol in an inhaler device. The inhaler device preferably comprises a (dry) powder inhaler device, a metered-dose inhaler device, a soft-mist inhaler device and/or an inhaler device including a ventilation tubing.

The computational inhaler device model represents in particular one or more of:
a particle size distribution of the aerosol,
a particle density of the aerosol,
a pressure of the carrier gas of the aerosol, preferably at the outflow from a mouth piece and/or ventilation tubing of the inhaler device, preferably time-dependent relative to a respiration cycle,
an aerosol flow, preferably at the outflow from a mouth piece and/or ventilation tubing of the inhaler device, preferably time-dependent relative to a respiration cycle, and
a flow velocity of the aerosol, preferably at the outflow from a mouth piece and/or ventilation tubing of the inhaler device, preferably time-dependent relative to a respiration cycle,
preferably depending on at least one or more of a chosen device design parameter, a set device operation parameter and a respiration value of a respiration parameter influencing the generation process and/or flow of the aerosol in the inhaler device. The computational inhaler device model can be based on a CFD simulation (Computational Fluid Dynamics), preferably 3D-CFD, based on a structural model of the geometry of (parts of) the inhaler device, preferably obtained from a CAD-model (Computer Aided Design). A device design parameter can be indicative of a dimension of the inhaler device, in particular characterizing (a part of a) a flow domain of (a component of) the inhaler device.

A respiration value of a respiration parameter can be a boundary condition for the computational inhaler device model, preferably a inhalation gas flow and/or a inhalation suction pressure, prescribed at an outflow of the computational inhaler device model, preferably time-dependent relative to a respiration cycle.

In one embodiment of the method, the step of determining at least one aerosol value uses a computational inhaler device model representing flow of an aerosol in an inhaler device. The computational inhaler device model preferably represents at least one component of the inhaler device characterized by at least one device design parameter. The device design parameter is preferably indicative of one or more of
a shape of a mouth piece and/or ventilation tubing of the inhaler device,
a diameter and/or shape of a nozzle of the inhaler device,
a flow channel geometry from an outlet of an aerosol generation and/or aerosol storage chamber to an outlet, preferably of a mouth piece and/or ventilation tubing, of the inhaler device, and
a volume and/or geometry of a canister containing a, preferably liquid, orally inhaled and/or nasal drug product.

A device operation parameter can be indicative of an (adjustable) setting of the inhaler device. An inhaler operation parameter is particularly selected from one or one of:
a, preferably time-dependent, pressure in a canister containing an orally inhaled drug product, preferably a canister configured to be received in a metered-dose inhaler device;
a mass and/or volume flow of a carrier gas supplied to the inhaler device;
a jet velocity of a jet of a liquid orally inhaled drug product impinging of a nebulizer device, such as a baffle, preferably of a soft-mist inhaler device;

a vibration frequency of a nebulizer device, preferably of a soft-mist inhaler device; and a rotational speed and/or a groove geometry of a nebulizer device.

Preferably at least one device design parameter, respiration parameter and/or inhaler operation parameter influences the generation process and/or flow of the aerosol in the inhaler device and is represented by the computational inhaler device model. The specific parameter(s) represented by the computational inhaler device model depend(s) on the inhaler device used, for example a (dry) powder inhaler device, a metered-dose inhaler device, a soft-mist inhaler device and/or an inhaler device including a ventilation tubing.

In one embodiment of the method, the efficacy parameter is indicative of one or more of: an, preferably local, effective dose; a, preferably local, density of deposited aerosol particles; and a, preferably local, concentration of an active ingredient of the orally inhaled and/or nasal drug product. An effective dose may be an amount of active ingredient delivered to the lung. A local effective dose may be an amount of active ingredient delivered to a specific area of the respiratory system, in particular an area in the lung, such as (a) specific location(s) (zone) in the airways or the lung tissue, left or right lung, pulmonary lobe(s) and/or airway generation(s).

A (local) effective dose or a concentration of an active ingredient can be determined at least based on the computed spatial particle deposition distribution and a predetermined dose (concentration and/or amount) of active ingredient contained in an (each) deposited particle. A density of deposited aerosol particles can be determined based on the computed spatial particle deposition distribution, in particular as a number of deposited aerosol particles per (lung) volume and/or (internal) airway surface. In particular, particles that were inhaled, but exhaled again later, are not part of the spatial particle deposition distribution.

The efficacy parameter, in particular a (local) effective dose, can be an equivalent efficacy parameter, in particular an equivalent (local) effective dose, of a similar (generic) drug product, in particular in relation to an original drug product. The described method for assessing the efficacy for pulmonary drug delivery can be used to assess whether a similar, in particular generic, drug product, preferably containing the same active ingredient, has the same efficacy for pulmonary drug delivery than the original drug product. Hence medical administration processes could be accelerated and/or simplified using the described method.

In one embodiment of the method, the aerosol particles contain a predetermined dose of an active ingredient of the orally inhaled and/or nasal drug product. The efficacy parameter can be indicative of a blood concentration of the active ingredient in the blood. Preferably, computing of at least one value of the blood concentration uses a computational absorption model representing absorption of the active ingredient contained in the aerosol particles into a blood circulation. Alternatively or additionally, the efficacy parameter can be indicative of a tissue concentration of an active ingredient in the lung tissue. Preferably, computing of at least one value of the tissue concentration uses a computational absorption model representing absorption of the active ingredient contained in the aerosol particles into a lung tissue. A computational absorption model is preferably based on pharmacometric modelling described in more detail below. Since some drugs are intended to be delivered to the blood (blood plasma) circulation and/or the lung tissue via the lungs, particularly to reach a systemic effect in the body, it is of interest to assess the efficacy based on the concentration of the active ingredient in the blood and/or the lung tissue.

In one embodiment of the method, the efficacy parameter is indicative of a, preferably time-dependent, spatial concentration distribution of an active ingredient of the orally inhaled and/or nasal drug product in a lung tissue of the respiratory system and/or in a blood circulation. Preferably, the at least one efficacy value is at least one, preferably time-dependent, concentration value of the active ingredient in the lung tissue and/or in the blood circulation. Computing the at least one efficacy value preferably uses a computational absorption model representing absorption of the active ingredient, which is contained in aerosol particles deposited in the respiratory system, in the lung tissue and/or in the blood circulation. A first, preferably time-dependent, concentration value of the active ingredient in a lung tissue in a first region of the discretized respiratory-system structure is preferably different from a second, preferably time-dependent, concentration value of the active ingredient in a lung tissue in a second region of the discretized respiratory-system structure. A first, preferably time-dependent, concentration value of the active ingredient in a blood circulation in a first region of the discretized respiratory-system structure is preferably different from a second, preferably time-dependent, concentration value of the active ingredient in a blood circulation in a second region of the discretized respiratory-system structure. A higher concentration of active ingredient typically indicates a higher efficacy of pulmonary drug delivery. The concentration value can indicate a (local) effective dose of the active ingredient and optionally whether a toxic concentration is reached (locally). Obtaining a spatial concentration distribution of the active ingredient enables assessment of the efficacy of pulmonary drug delivery locally, in particular pulmonary drug delivery to specific areas of interest of the lungs, preferably to pathological regions of the lungs to be treated by the drug (lung diseases) or to regions where the drug can be effectively absorbed in the blood circulation to reach pathological areas of the body outside of the lungs (no lung diseases).

In one embodiment of the method, the spatial particle deposition distribution comprises, preferably averaged, subdomain-specific particle deposition distributions in a plurality of subdomains of the discretized respiratory-system structure, wherein the at least one efficacy value of the at least one efficacy parameter is determined depending on at least one of the subdomain-specific particle deposition distributions. Preferably, each subdomain represents: a healthy region or a pathological region of the respiratory system; and/or at least a part of the conducting airways, in particular a specific generation of the (conducting) airways, or at least a part of the respiratory airways, in particular of the alveoli; and/or a specific lobe of the lungs; and/or a region of the respiratory system in proximity to (or within a defined radius around) a tumor; and/or a (pathological) region of the lung targeted for surgery (e.g. segmentectomy); and/or a branch of the respiratory system effected by endobronchial valves (for patients suffering from COPD). The plurality of subdomains can collectively represent a partition of the domain of the lung (respiratory system) or the domain of the whole lung (respiratory system). A subdomain-specific particle deposition distribution can be indicative of the particle deposition distribution in each of a plurality of subdomains of the discretized respiratory-system structure. A subdomain-specific particle deposition distribution in a specific subdomain preferably refers to a specific section of the lung (e.g., a specific lobe, left/right lung, specific airway generation, etc.). In this way, pulmonary drug delivery to specific subdomains of interest in the lungs can be assessed based on a subdomain-specific efficacy value. A subdomain-specific particle deposition distribution Ddist can be derived from a spatial distribution of the density of deposited aerosol particles (particle sizes) in different areas of the discretized respiratory system, preferably by averaging over the subdomain. Considering drug absorption for a reduced number of subdomains, in particular by using averaged subdomain-specific particle deposition distributions reduces the need for computational resources.

In one embodiment, the computational absorption model may represent absorption of the active ingredient, which may be contained in aerosol particles deposited in the respiratory system, in a lung tissue and/or in a blood circulation based on the spatial particle deposition distribution and at least one absorption value of at least one absorption parameter. The computational absorption model may be preferably based on pharmacokinetic modeling. In particular, besides absorption of the active ingredient in the lung tissue, the computational absorption model can further represent at least one or more of mucociliary clearance, dissolution of the active ingredient in a pulmonary lining fluid and disposition of the active ingredient, preferably from the lung tissue, into the blood circulation. A pulmonary lining fluid is preferably a mucus of the conducting airways or an alveolar lining fluid of the respiratory airways. Pharmacokinetic (PK) modelling is more accurate, particularly with respect to the location in the lungs where absorption processes of the drug take place. Thus, local predictions with high spatial resolution of efficacy parameters, such as the drug (active ingredient) concentration, in different regions of the lungs become possible, even in different regions of the lung tissue (before the drug enters the systemic blood circulation). PK modeling can circumvent experiments in which an orally inhaled and/or nasal drug product has to first be administered to patients or healthy individuals in order to then determine the dose that has effectively reached the blood circulation by taking blood samples.

In a preferred embodiment, the at least one efficacy value is computed using a physiologically structured population model (PSPM) according to "Hartung N, Bor-ghardt J. *A mechanistic framework for a priori pharmacokinetic predictions of orally inhaled drugs*. PLOS Computational Biology (2020); 16: e1008466".

In one embodiment, the at least one efficacy value may include the amount or fraction of the active ingredient removed from the lung due to mucociliary clearance. In a further embodiment, the at least one efficacy value may include the local concentration $C_{flu}$ of the active ingredient in the pulmonary lining fluid. In another embodiment, the at least one efficacy value may include the local concentration $C_{flu}$ of the active ingredient in the pulmonary lining fluid and/or the local concentration $C_{tis}$ of the active ingredient in the lung tissue (pulmonary tissue). In other embodiments, the at least one efficacy value may include the local concentration $C_{tis}$ of the active ingredient in the lung tissue and/or the local concentration $C_{sys}$ of the active ingredient in the systemic blood circulation.

The at least one absorption value of the at least one absorption parameter is preferably measured or obtained from a database. Absorption values obtained from a database can in particular indicate physical properties of the aerosol, the active ingredient and/or the lung tissue. The at least one absorption value may be computed based on analytical relations of physical properties of the aerosol particles and/or of the active ingredient of the orally inhaled and/or nasal drug product. In some cases, absorption values, such as gas flow velocities, can be or be obtained from the computational lung model.

Figure 2:
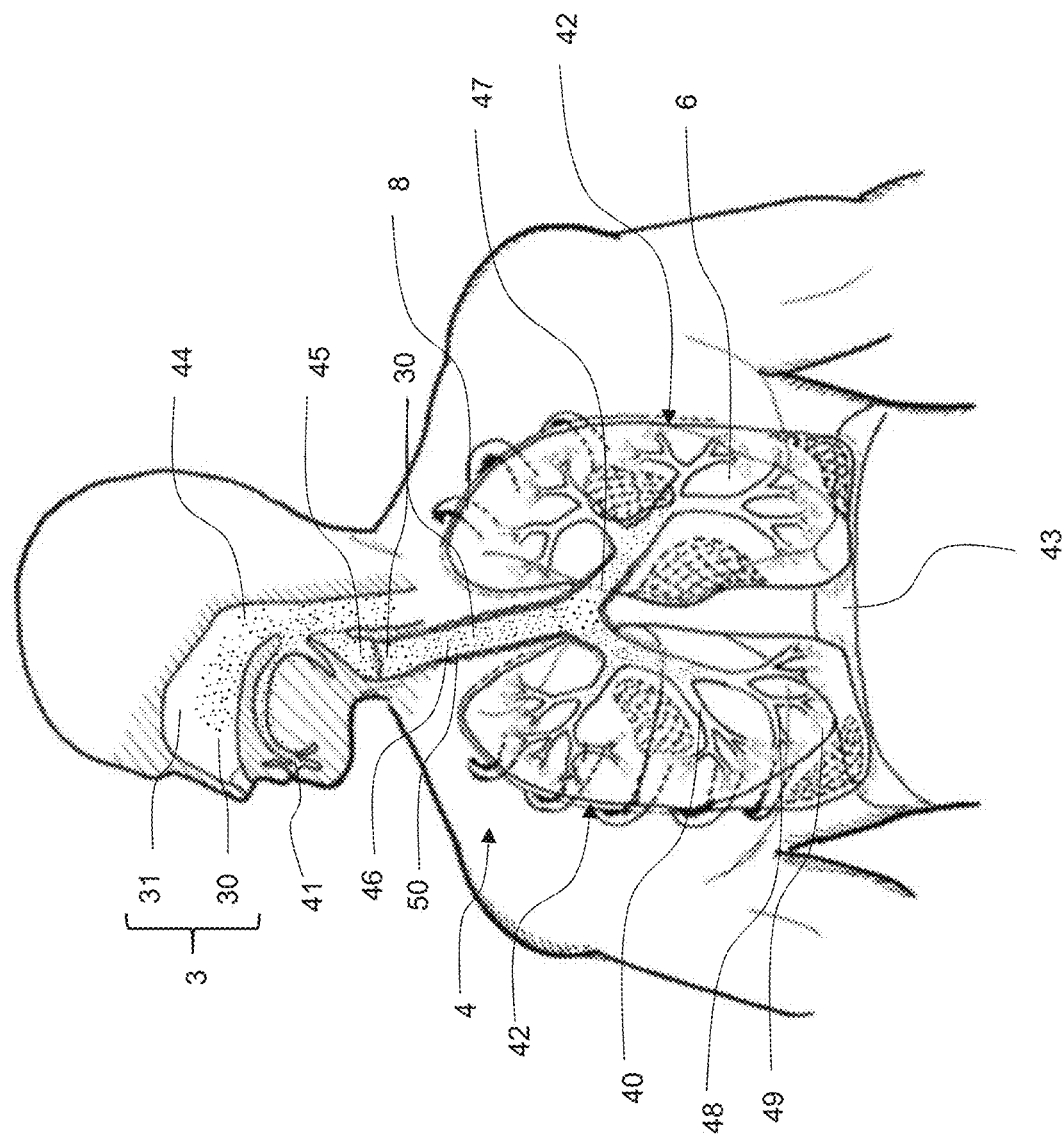

Geometric absorption parameters can be derived from the discretized respiratory-system structure. Values of the at least one absorption parameter may also be a value of the at least one aerosol parameters (e.g. particle size, particle density). The at least one absorption value may be a function of the generational depth, an anatomical lung entity (as shown in FIG. 2), real spatial location, or any combination thereof.

Typical absorption parameters are: geometric particle size/volume (distribution), particle density (distribution), absorption rate, (effective/apparent) permeability, partition coefficient (lung-to-plasma, lung-to-unbound-plasma, tissue), fraction unbound/unionized, (saturation) solubility, dissolution rate, diffusivity, blood-to-plasma ratio, epithelial lining fluid (ELF) depth, tissue depth, perfusion, metabolic kinetics, transport kinetics, drug degradation rate, and tissue binding constant.

In one embodiment of the method, preferably the previous embodiment, the at least one absorption parameter is indicative of one or more of
- a saturation solubility $C_s$ of the active ingredient of the orally inhaled and/or nasal drug product in a pulmonary lining fluid,
- a dissolution rate $k_{diss}$, preferably a local maximum dissolution rate, of the active ingredient of the orally inhaled and/or nasal drug product in a pulmonary lining fluid,
- an effective permeability $P_{app}$ of an airway wall for the active ingredient of the orally inhaled and/or nasal drug product,
- a tissue-to-unbound plasma partition coefficient $K_{pu,tis}$ indicating the partition of a concentration of the unbound active ingredient in the lung tissue to a concentration of the active ingredient in the blood plasma,
- a tissue-to-plasma partition coefficient $K_{p,tis}$ indicating the partition of a concentration of the active ingredient in the lung tissue to a concentration of the active ingredient in the blood plasma.

Further parameters can comprise a particle density, preferably an averaged particle density, a particle size, preferably a mean particle size, an airway radius $r^{br}$, diffusivity D, a surface area SA of an airway, local perfusion/blood flow Q or the blood-to-plasma ratio in the lung BP.

In one embodiment of the method, the at least one absorption value of the at least one absorption parameter, in particular a value of the saturation solubility $C_s$, the dissolution rate $k_{diss}$, the effective permeability $P_{app}$, the tissue-to-unbound plasma partition coefficient $K_{pu,tis}$ and/or the tissue-to-plasma partition coefficient $K_{p,tis}$, is determined depending on a predetermined pathological modification of at least one zone of the respiratory system caused by a lung disease of the lung. Values of absorption parameters can depend on a pathological condition of the lung. For example, asthma can result in thickened airway walls, mucociliary clearance can be affected by lung diseases and fibrotic lung tissue can have modified absorption properties. In this way, a more accurate, in particular patient-specific, assessment of efficacy of pulmonary drug delivery is possible.

In one embodiment of the method, the at least one absorption value of the at least one absorption parameter is determined depending on the spatial particle deposition distribution. The spatial particle deposition distribution preferably comprises subdomain-specific particle deposition distributions in a plurality of subdomains of the discretized respiratory-system structure. In particular, each subdomain represents: a healthy region or a pathological region of the respiratory system; and/or at least a part of the conducting airways, in particular a specific generation of the airways, or at least a part of the alveoli; and/or a specific lobe of the lungs. The at least one absorption value is preferably determined depending on a subdomain of the discretized respiratory-system structure. As a result, a first absorption value of an absorption parameter in a first subdomain can differ from a second absorption value of the absorption parameter in a second subdomain. Values of absorption parameters (e.g. dissolution rate) can vary depending on the particle deposition (e.g. in a conducting airway region or in an alveolar region), in particular depending on the airway generation.

The at least one absorption value may be obtained from an in-vitro analysis (in-vitro experiment), in particular from an in-vitro measurement, in particular per-formed in a laboratory (e.g. measurements of dissolution and/or solubility, in-vitro assay). In-vitro measurements may use real or artificial human or animal pulmonary tissue. The at least one absorption value may also be obtained from a database storing values of absorption parameters that have been obtained in-vivo using one or more of: bronchosorption, bronchial brush, mucosal biopsy, bronchoalveolar lavage (BAL) or blood sampling. However, methods according to the invention do not involve any steps of surgery and are in particular no methods for treatment of the human or animal body by surgery or therapy.

In one embodiment of the method, the at least one absorption value is determined by in-vitro measurement, in particular using a microfluidic lung-on-a-chip device. Such devices emulate the mechanical and biochemical behavior of the (human) lung in a microfluidic device (lung-on-a-chip) using tissue engineering. By applying a simulated air and/or blood flow relevant parameters for absorption processes involving lung tissue can be measured. Lung-on-a-chip devices are known in general. WO 2013/086486 A1 discloses technical aspects of a microfluidic lung-on-a-chip device. A person skilled in the art is able conduct an in-vitro measurement of an absorption value of an absorption parameter to evaluate the present computational absorption model using a microfluidic lung-on-a-chip device. In-vitro measurement of absorption parameters has the advantage that drugs do not actually have to be administered to patients or healthy individuals in order to determine relevant absorption parameters. Furthermore, the different parameters can be measured accurately under defined laboratory conditions.

In one embodiment, the method comprises the following further steps:
  determining a predetermined minimum efficacy value of the efficacy parameter;
  using the determined at least one aerosol value as a start value;
  adapting the aerosol value, preferably in an iterative loop of repeatedly performing at least some the steps of the method according to any one of the preceding claims, until the computed efficacy value is equal to or larger than the predetermined minimum efficacy value; and
  storing the adapted aerosol value in a storage device, outputting the adapted aerosol value to a display device and/or providing the adapted aerosol value for use in assessing the efficacy for pulmonary drug delivery as an optimized aerosol value of the aerosol parameter.

The method can be carried out iteratively, preferably controlled by an optimization algorithm. Obtaining an optimized aerosol value is a particular advantage of the described method, since improved (optimize) efficacy values can be used in the technical applications described in this disclosure.

In one embodiment of the method, the at least one aerosol value, in particular if the at least one efficacy value is equal to or larger than a predetermined minimum efficacy value of the efficacy parameter and preferably lower than a predetermined maximum efficacy value of the efficacy parameter, is used for one or more of

- generating an aerosol comprising aerosol particles containing an orally inhaled and/or nasal drug product, preferably using an inhaler device, wherein the aerosol is characterized by the aerosol value,
- setting a device operation parameter of an inhaler device such that the inhaler device generates an aerosol characterized by the aerosol value, and
- designing and/or producing an inhaler device configured to generate an aerosol characterized by the aerosol value and
- producing an orally inhaled and/or nasal drug product, preferably in form of a dry powder, characterized by the aerosol value of the aerosol parameter, preferably being a particle size, a mean particle size and/or a particle size distribution.

A predetermined minimum efficacy value can define a lower threshold of a (desired) efficacy of pulmonary drug delivery, in particular above which a (positive and/or desired) medical effect of the active ingredient is known or observed (or below which no medical effect is known or observed, respectively). A predetermined maximum efficacy value can define an upper threshold of a (desired) efficacy of pulmonary drug delivery, in particular above which a (negative and/or undesired) effect of the active ingredient is known or observed, in particular (strong or undesired) side effects or a toxic effect. Accordingly, using the method for the described technical applications renders possible providing an aerosol, and inhaler device and/or a drug product having a desired efficacy for pulmonary drug delivery, in particular a causing or facilitating a desired medical effect.

In one embodiment of the method, the at least one efficacy value, in particular if the at least one efficacy value is larger than a predetermined minimum efficacy value of the efficacy parameter and preferably lower than a predetermined maximum efficacy value of the efficacy parameter, is used for one or more of:

- assessing the performance of an inhaler device for pulmonary drug delivery, in particular the effect of a setting of a device operation parameter and/or the effect of a device design parameter of the inhaler device on the performance for pulmonary drug delivery, wherein the inhaler device is configured, in particular when operated with a predetermined setting of a device operation parameter, to generate an aerosol for pulmonary drug delivery such that the aerosol is characterized by the aerosol value of the aerosol parameter,
- assessing the efficacy and/or safety of an orally inhaled and/or nasal drug product, in particular of a dose of an active ingredient of an orally inhaled and/or nasal drug product, for pulmonary drug delivery, wherein the orally inhaled and/or nasal drug product is prepared to be administered in the form of an aerosol, preferably using an inhaler device, characterized by the aerosol value of the aerosol parameter, and
- assessing the efficacy of a drug/device combination product of an orally inhaled and/or nasal drug product and an inhaler device for pulmonary drug delivery, wherein the orally inhaled and/or nasal drug product is prepared to be administered in the form of an aerosol characterized by the aerosol value using the inhaler device, in particular when operated with a predetermined setting of a device operation parameter, and the inhaler device is configured, in particular when operated with a predetermined setting of a device operation parameter, to generate an aerosol characterized by the aerosol value of the aerosol parameter.

Similarly, as previously described, using the described method for the described technical applications renders possible designing and/or operating an inhaler device, producing a drug product or providing a drug/device combination product having a desired efficacy for pulmonary drug delivery, in particular causing or facilitating a desired medical effect. In particular, the method can be used to select an appropriate combination of an orally inhaled and/or nasal drug and an inhaler device as a suited (efficient and/or safe) pair for a drug/device combination product.

According to a different possible application, the described methods for assessing the efficacy and/or safety could be used to accelerate and simplify medical or pharmaceutical approval procedures for medical devices or drug products by health administrations.

The invention also relates to a method for assessing the performance of an inhaler device for pulmonary drug delivery, wherein the inhaler device is configured to generate an aerosol comprising aerosol particles containing an orally inhaled and/or nasal drug product, wherein the performance of the inhaler device for pulmonary drug delivery is assessed depending on the efficacy of the aerosol for pulmonary drug delivery when assessed according any one of the previously described embodiments of the method. The performance of an inhaler is preferably determined based on the efficacy for pulmonary drug delivery of the aerosol it generates depending on device design and/or operation parameters. The effects and advantages of the method are similar to those of at least one previously described method.

The invention also relates to a method for assessing the efficacy and/or safety of an orally inhaled and/or nasal drug product for pulmonary drug delivery, wherein the orally inhaled and/or nasal drug product is prepared to be administered in the form of an aerosol, preferably using an inhaler device, wherein the efficacy of the orally inhaled and/or nasal drug product for pulmonary drug delivery is assessed depending on the efficacy of the aerosol for pulmonary drug delivery when assessed according to any one of the previously described embodiments of the method. Efficacy and/or safety of a drug product can be assessed in comparison to predetermined minimum and/or maximum efficacy values. The effects and advantages of the method are similar to those of at least one previously described method.

The invention also relates to a method for assessing the efficacy of a drug/device combination product of an orally inhaled and/or nasal drug product and an inhaler device for pulmonary drug delivery, wherein the inhaler device is configured to generate an aerosol comprising aerosol particles containing the orally inhaled and/or nasal drug product and the orally inhaled and/or nasal drug product is prepared to be administered in the form of the aerosol using the inhaler device, wherein the efficacy of a drug/device combination product for pulmonary drug delivery is assessed is depending on the efficacy of the aerosol for pulmonary drug delivery when assessed according to any one of the previously described embodiments of the method. The performance of an inhaler is preferably determined based on the efficacy for pulmonary drug delivery of the aerosol it generates depending on device design and/or operation parameters. Efficacy and/or safety of the drug product can be assessed in comparison to predetermined minimum and/or maximum efficacy values. The effects and advantages of the method are similar to those of at least one previously described method.

At least one problem underlying the invention is solved by a computer program product comprising instructions which, when the program is executed by a computer, cause the computer to carry out at least some (preferably all) steps of the previously described methods. The computer program can be carried out on a distributed computer system comprising a plurality of computers and/or servers connected via a wireless and/or wired network.

At least one problem underlying the invention is solved by a computer-readable medium comprising instructions, the instructions, when being executed by a computer, implementing at least some (preferably all) steps of the previously described methods for assessing the efficacy of an aerosol for pulmonary drug delivery.

The invention also relates to a method for generating an aerosol comprising aerosol particles containing an orally inhaled and/or nasal drug product using an inhaler device, the method comprising the following steps:

carrying out the method according to any one of the preceding claims;

providing an orally inhaled and/or nasal drug product, in particular based on an efficacy assessment according to a previously described method, in particular if the at least one efficacy value is equal to or larger than a predetermined minimum efficacy value of the efficacy parameter;

providing an inhaler device, in particular based on an efficacy assessment according to a previously described method, in particular if the at least one efficacy value is equal to or larger than a predetermined minimum efficacy value of the efficacy parameter;

supplying the orally inhaled and/or nasal drug product to the inhaler device;

operating the inhaler device, preferably by setting a device operation parameter of the inhaler device based on an efficacy assessment according to a previously described method, in particular if the at least one efficacy value is equal to or larger than a predetermined minimum efficacy value of the efficacy parameter, such that the inhaler device generates an aerosol characterized by the aerosol value of the aerosol parameter.

The effects and advantages of the method for generating an aerosol are similar to those of the previously described method. Furthermore, the generated aerosol can be used for testing (in a testing process, preferably as part of a design process) of an inhaler device, in particular by analyzing properties of the aerosol (aerosol particles) generated by the inhaler device, preferably by measuring at least one aerosol value of the aerosol parameter and preferably comparing the determined aerosol value (used as input value for the simulation) to the measured aerosol value of the aerosol parameter. The tested inhaler device is preferably a (dry) powder inhaler device, metered-dose inhaler device, nebulizer (soft-mist) inhaler device or an inhaler device including a ventilation tubing.

The invention also relates to a method of designing and/or producing an inhaler device configured to generate an aerosol comprising aerosol particles containing an orally inhaled and/or nasal drug product, the method comprising the following steps:

choosing at least one value of a device design parameter characterizing an inhaler device;

carrying out the previously described method, wherein preferably the step of determining at least one aerosol value uses a computational inhaler device model representing flow of an aerosol in an inhaler device;

designing and/or producing an inhaler device, in particular based on an efficacy assessment according to any one of the preceding claims, in particular if the at least one efficacy value is equal to or larger than a predetermined minimum efficacy value of the efficacy parameter, such that the inhaler device implements the chosen value of the device design parameter.

The computational inhaler device model can represent at least one component of the inhaler device characterized by at least one device design parameter. A device design parameter in this method can be one or more of the device design parameters previously described with reference to a computational inhaler device model. The effects and advantages of the method are similar to those of at least one previously described method.

The invention also relates to an inhaler device for administering orally inhaled and/or nasal drug products designed and/or produced by performing the method steps of the previously described method of designing and/or producing an inhaler and/or ventilator device. The effects and advantages of the inhaler device are similar to those of at least one previously described method.

In one embodiment, the inhaler device comprises a ventilation tubing for administering orally inhaled and/or nasal drug products to mechanically ventilated patients. The ventilation tubing preferably comprises a first inlet for an aerosol flow and a second inlet for a ventilation gas flow generated by a ventilation device. Preferably, the ventilation tubing further comprises a common outlet for the aerosol flow and the ventilation gas (air) flow. An aerosol flow generated by a nebulizer device can be supplied to (merge with) a ventilation gas flow generated by the ventilation device and jointly supplies to the patient via a ventilation tubing. Such an inhaler device has the advantage that an aerosol of an orally inhaled and/or nasal drug product can be administered to a patient who is mechanically ventilated and unable to use a type of inhaler device requiring active breathing.

Figure 10A:
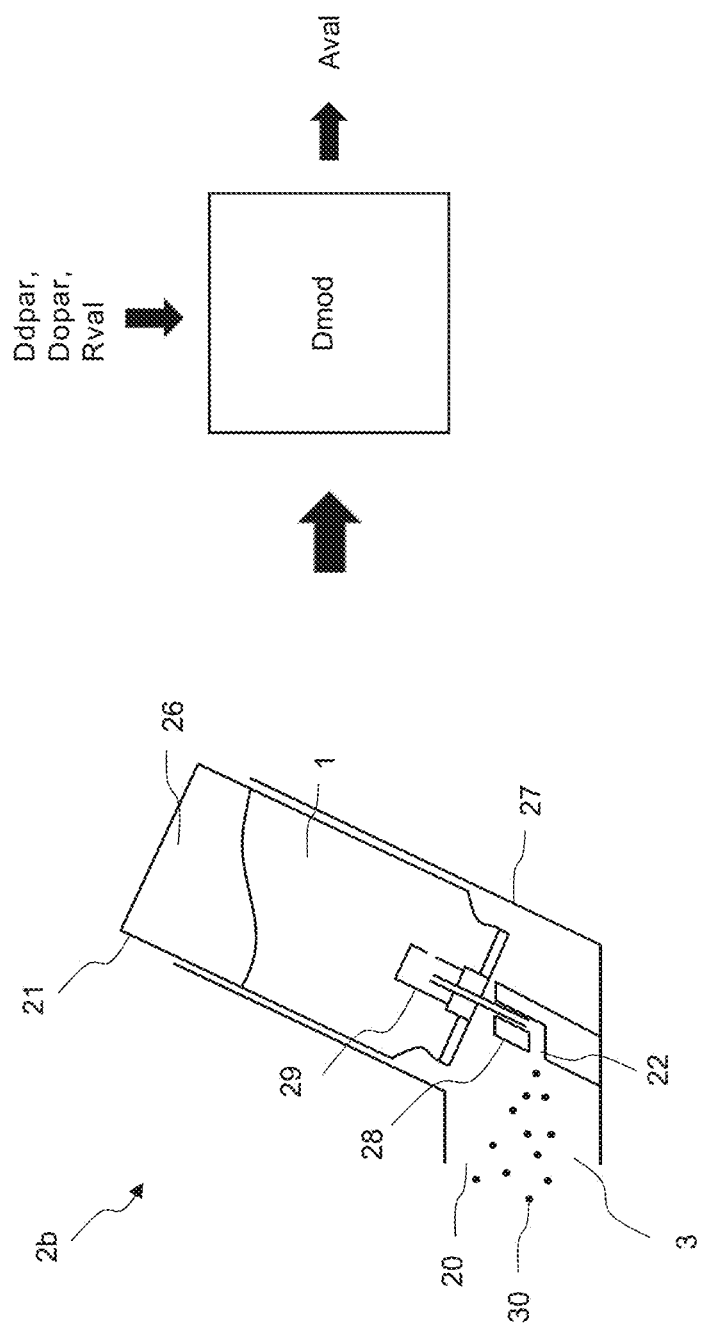
Figure 10B:
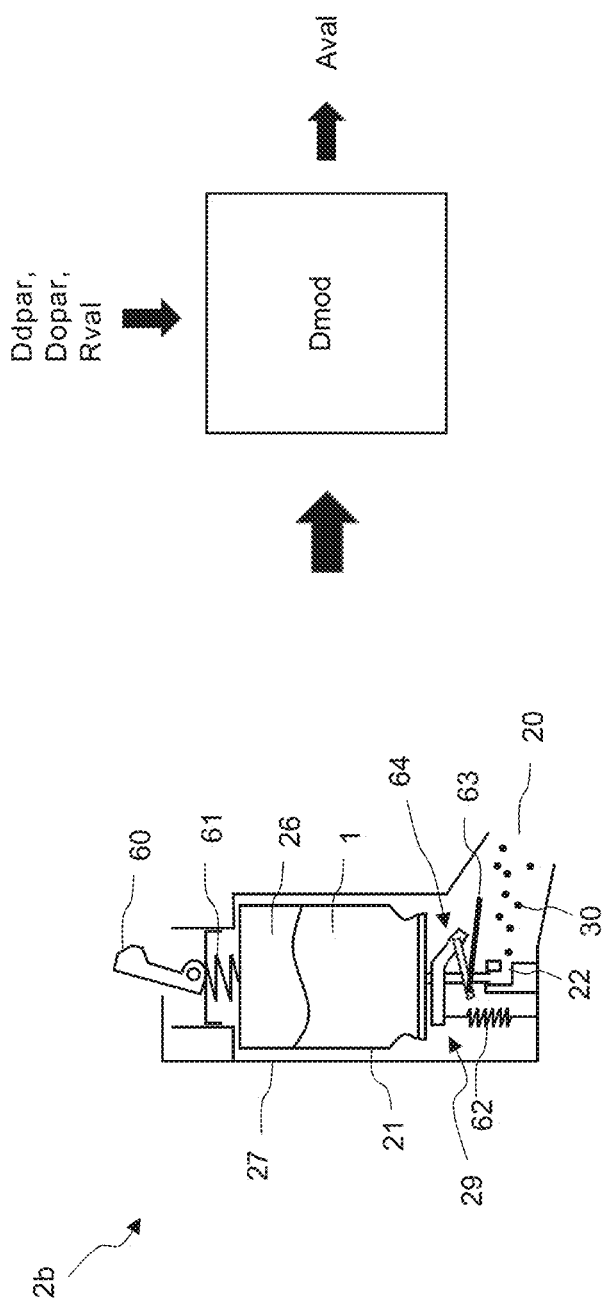
Figure 10C:
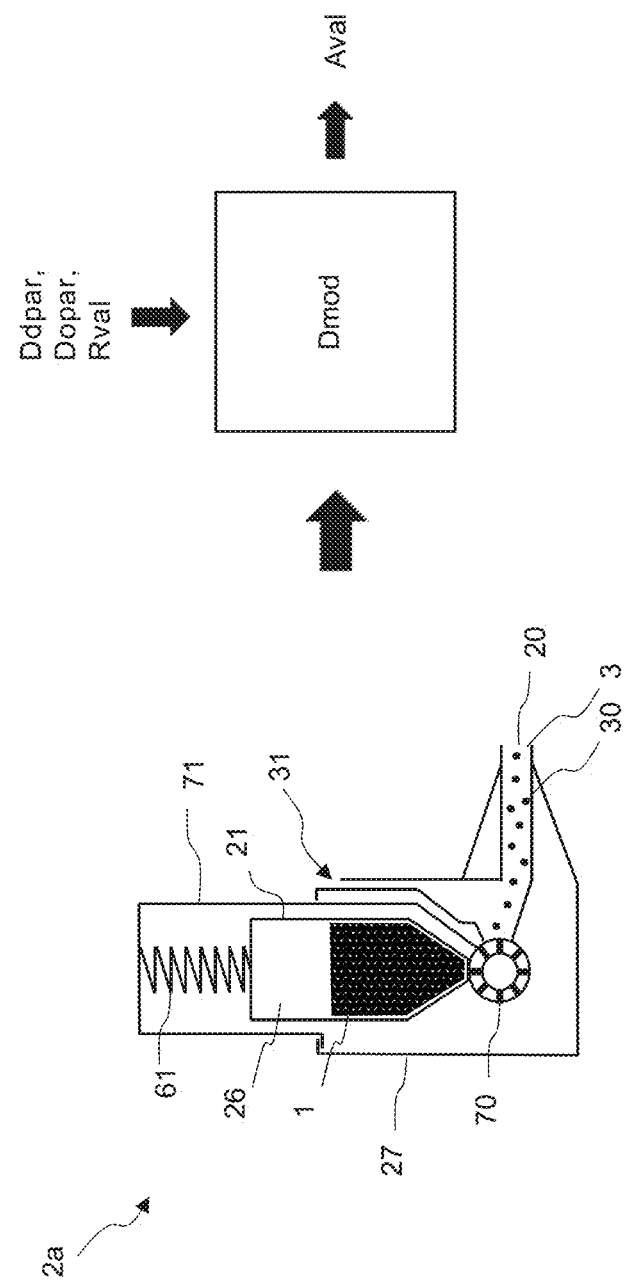
Figure 10D:
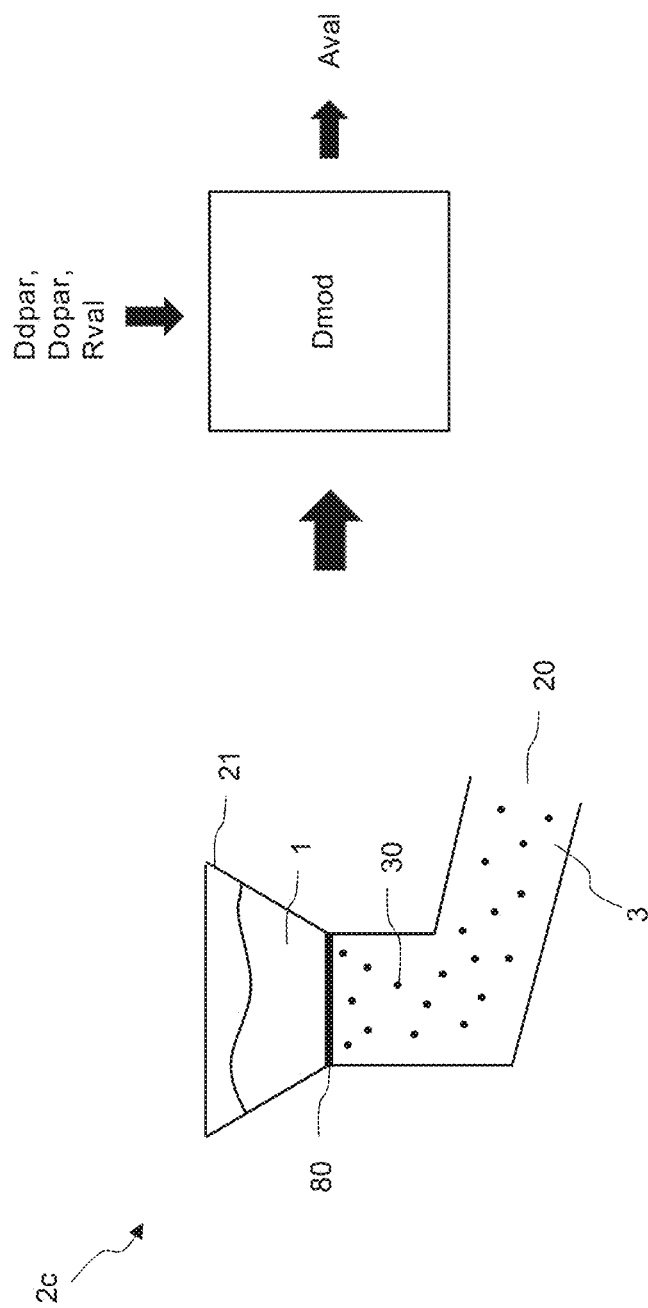
Figure 10E:
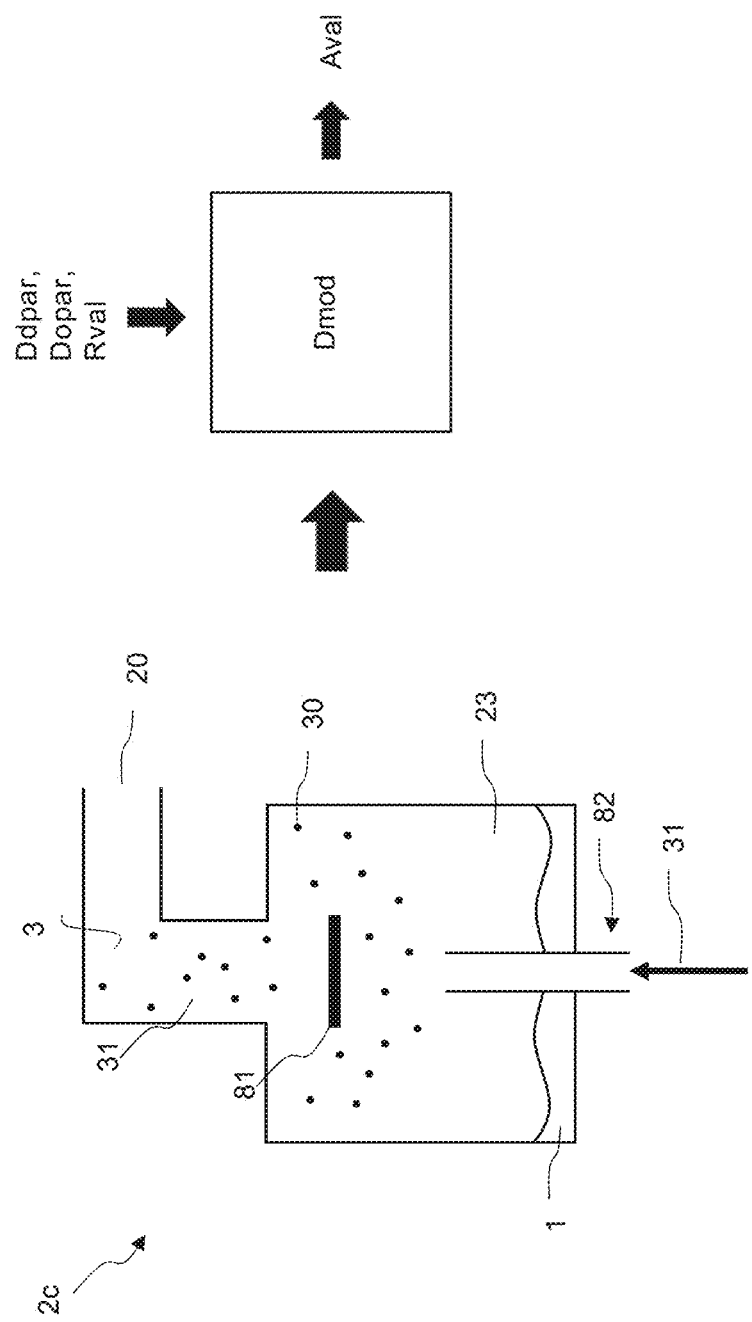
Figure 10F:
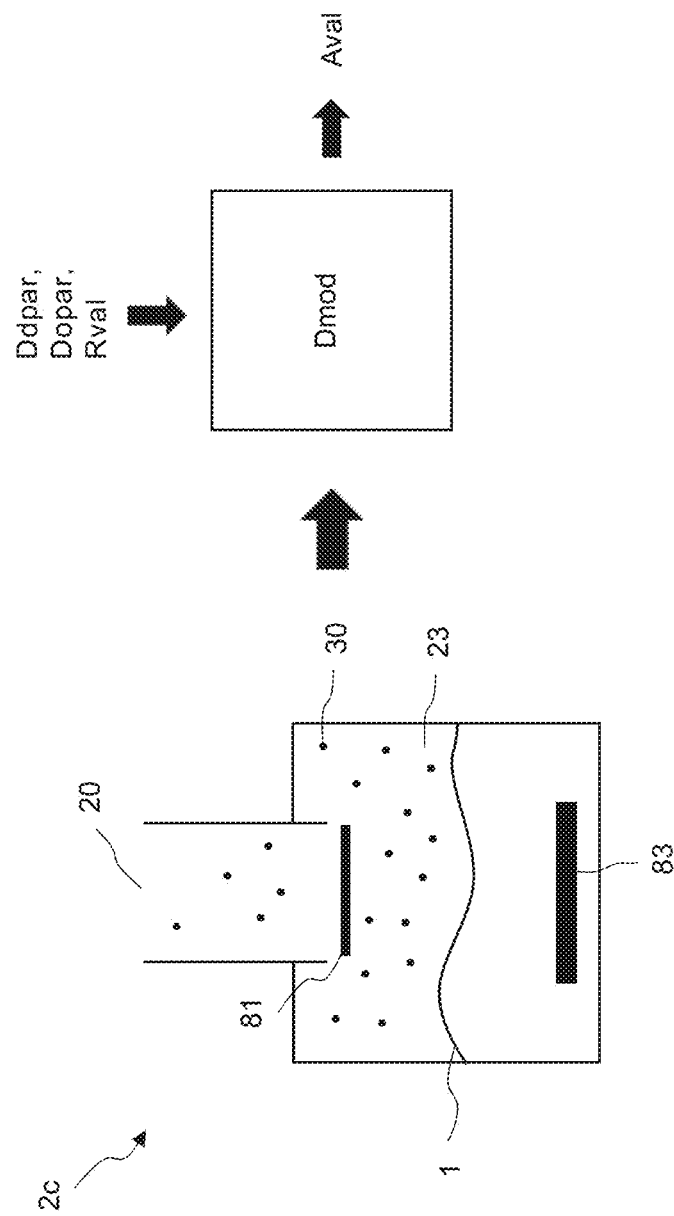
Figure 11:
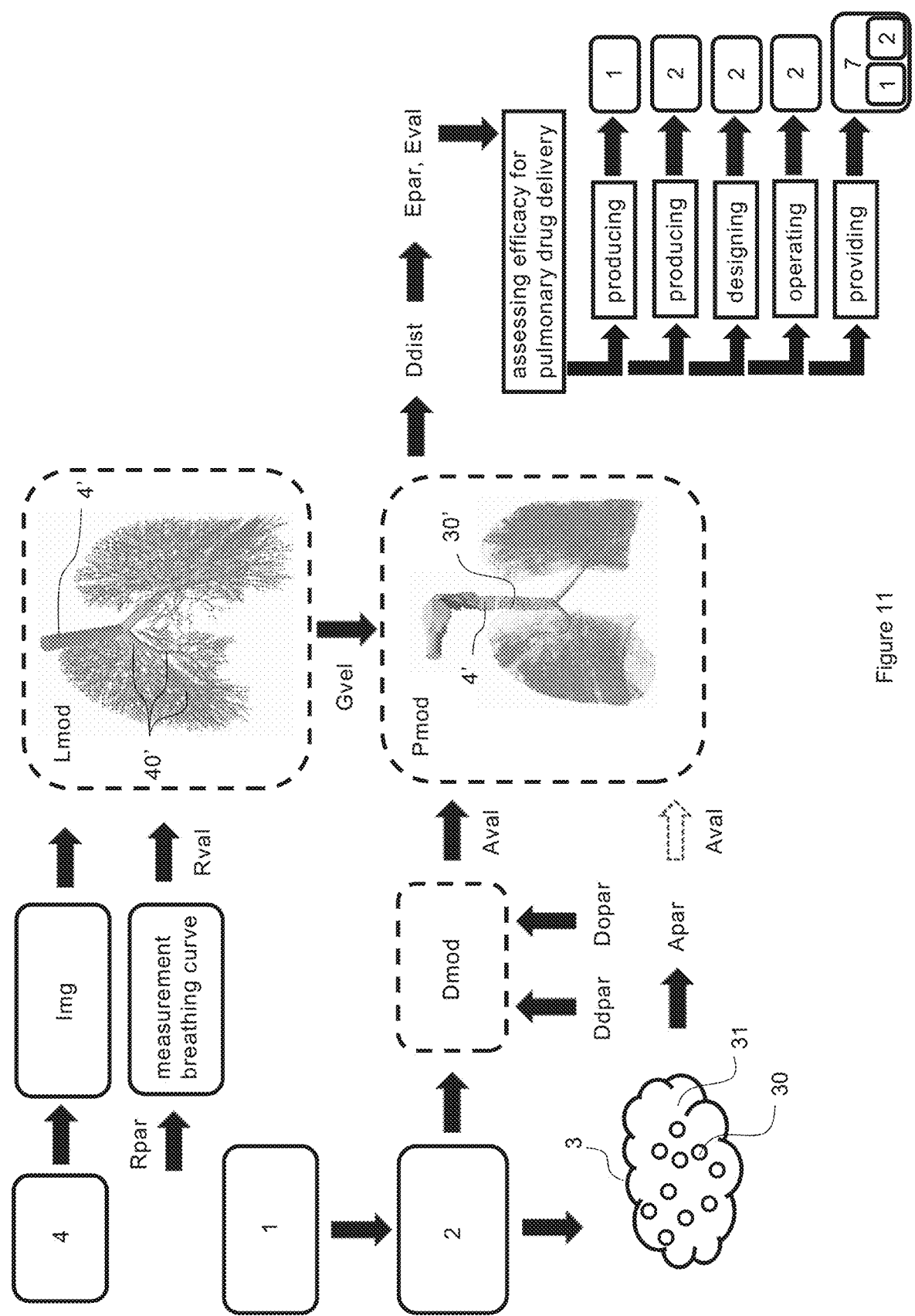

The invention also relates to a method for producing an orally inhaled and/or nasal drug product, preferably in the form of a dry powder, comprising carrying out the method according to any one of the preceding claims, wherein preferably a particle size characterizing the dry powder is chosen as the determined aerosol value;

producing an orally inhaled and/or nasal drug product, preferably in form of a dry powder, in particular based on an efficacy assessment of an aerosol characterized by the determined aerosol value according to any one of the preceding claims, in particular if the at least one efficacy value is equal to or larger than a predetermined minimum efficacy value of the efficacy parameter, such that the orally inhaled and/or nasal drug product is prepared to be administered, using an inhaler device, in the form of an aerosol characterized by the aerosol value of the aerosol parameter.

Preferably, the particle size characterizing the dry powder corresponds to a (mean) grain size of solid particles of the dry powder. The (mean) particle size of the dry powder is preferably smaller than 10 μm, preferably between 1 and 5 μm, more preferably between 1 and 3 μm or between 3 and 5 μm. Generally, particles between 1 and 3 μm have preferably a systemic therapeutic effect in the body, since relatively smaller particles are deposited (also) in the alveolar area of the lungs, and preferably transported further into the blood circulation. Particles between 3 and 5 μm have preferably a local therapeutic efficacy in the lung, since relatively larger particles are (predominantly) deposited in the (conductive) airways and are less likely to reach the alveolar area.

The invention also relates to an orally inhaled and/or nasal drug product, in particular dry powder, obtained by performing the method steps of the previously described method for producing an orally inhaled and/or nasal drug product. The effects and advantages of such a drug product are similar to those of at least one previously described method.

The invention also relates to a drug/device combination product of an orally inhaled and/or nasal drug product and an inhaler device for administering orally inhaled and/or nasal drug products, wherein the drug/device combination product comprises a previously described orally inhaled and/or nasal drug product according to the invention and/or a previously described inhaler device according to the invention. The effects and advantages of such a drug/device combination product are similar to those of at least one previously described method.

BRIEF DESCRIPTION OF THE DRAWINGS

The invention is described in the context of further embodiments shown in the Figures, wherein FIG. 1 shows an illustration of a method for assessing pulmonary drug delivery, FIG. 2 shows a schematic illustration of the human respiratory system, FIG. 3 shows a schematic illustration of a computational particle transport and deposition model used in the method according to FIG. 1, FIG. 4 shows a detailed view of a schematic illustration of a computational particle transport and deposition model and a computational absorption model used in the method according to FIG. 1, FIG. 5 shows a schematic illustration of a computational particle transport model implementing a Lagrangian approach as used in the method according to FIG. 1, FIG. 6 shows an illustration of particle transport across an exemplary schematic airway bifurcation during inhalation and exhalation as used in the method according to FIG. 1, FIG. 7 shows a schematic illustration of an exemplary airway bifurcation library as used for particle transport in FIG. 6, FIG. 8 shows a schematic illustration of a computational particle deposition model used in the method according to FIG. 1, FIG. 9 shows a schematic illustration of a pharmacometric model for determining drug efficacy used in the method according to FIG. 1, FIG. 10*a* shows a schematic illustration of a pressurized metered-dose inhaler device and a corresponding computational inhaler device model, FIG. 10*b* shows a schematic illustration of a breath-activated metered-dose inhaler device and a corresponding computational inhaler device model, FIG. 10*c* shows a schematic illustration of a dry powder inhaler device and a corresponding computational inhaler device model, FIG. 10d shows a schematic illustration of a vibrating-mesh nebulizer inhaler device and a corresponding computational inhaler device model, FIG. 10e shows a schematic illustration of a jet nebulizer inhaler device and a corresponding computational inhaler device model, FIG. 10f shows a schematic illustration of an ultrasound nebulizer inhaler device and a corresponding computational inhaler device model, FIG. 10g shows a schematic illustration of a nebulizer inhaler device including ventilation tubing and a corresponding computational inhaler device model, and FIG. 11 shows an illustration of different methods using a method for assessing pulmonary drug delivery.

Figure 12:
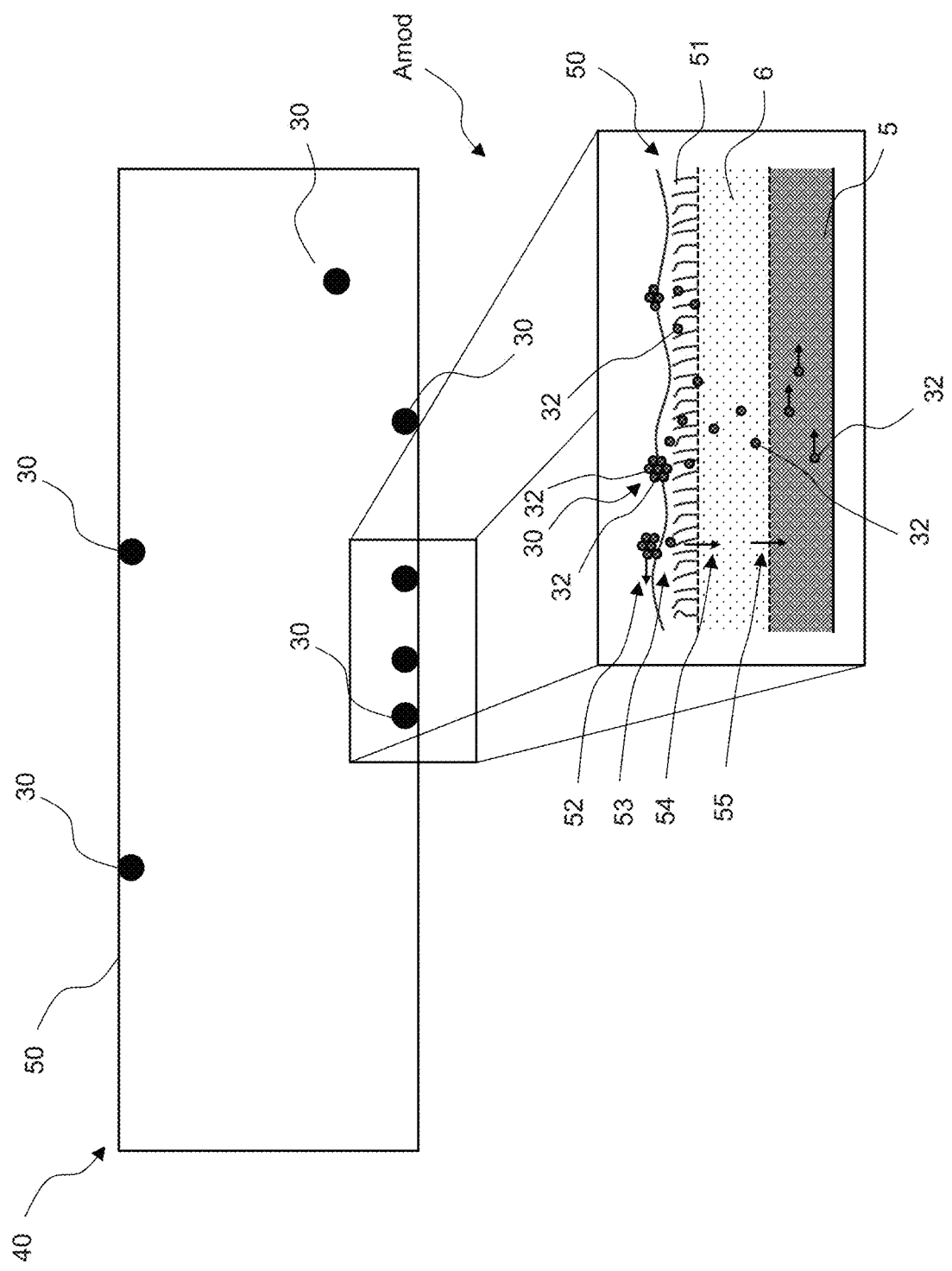
Figure 13:
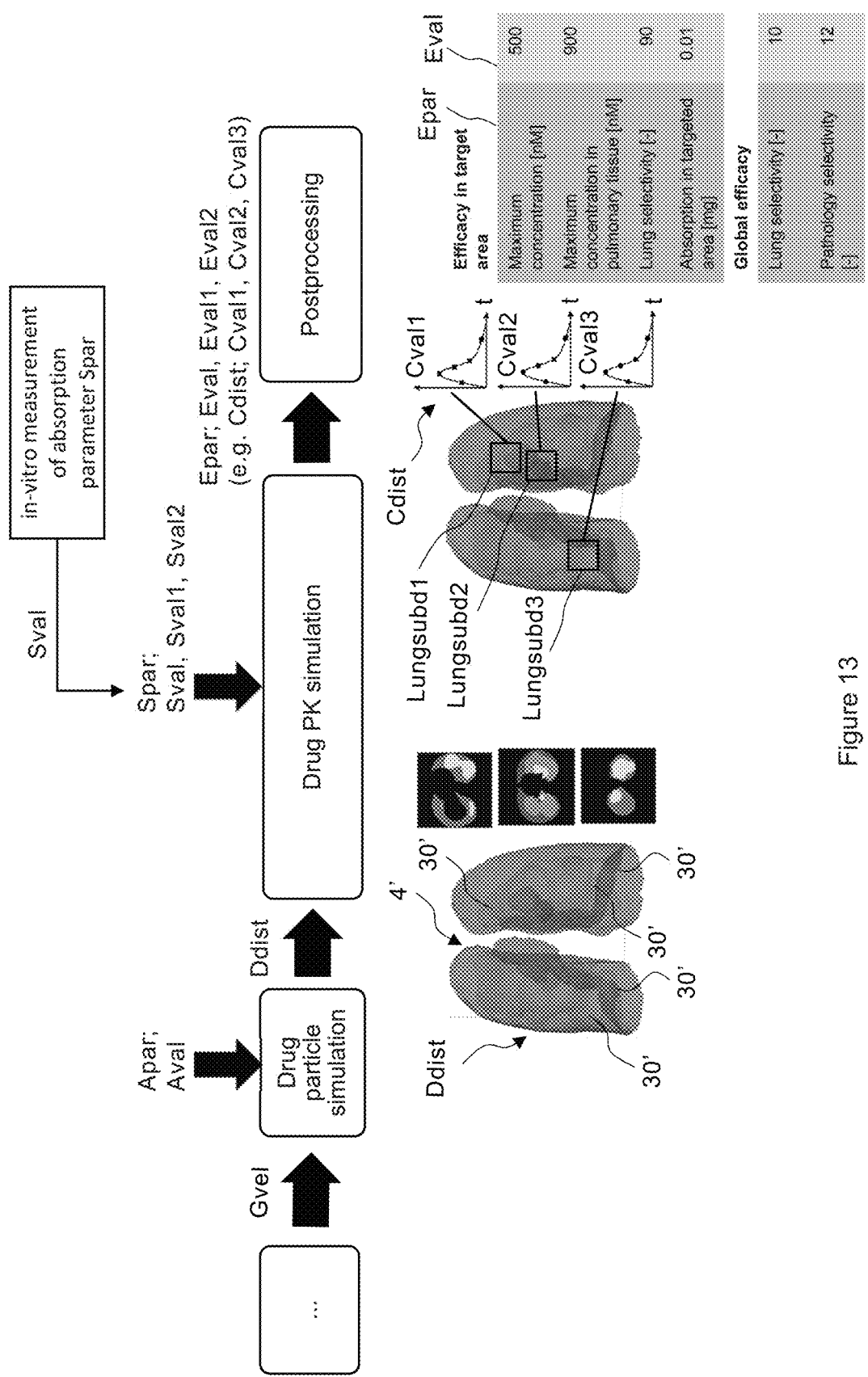

FIG. 12 shows a schematic illustration of the absorption of an active ingredient of an orally inhaled and/or nasal drug product based on pharmacokinetic modelling, FIG. 13 shows an illustration of a method for assessing pulmonary drug delivery by determining a concentration of an active ingredient of the drug in the lung tissue.

DETAILED DESCRIPTION

In the following description, the same reference numeral are used for elements having the same or a similar effect. In general, reference numerals comprising an apostrophe ('), e.g. 4', 40' or 30', refer to discretized (modelled/computational) quantities, whereas corresponding reference numerals without apostrophe, e.g. 4, 40 or 30, refer to the corresponding (real) physical quantities.

The method illustrated in FIG. 1 is suited for assessing the efficacy of an aerosol 3 (see, e.g. FIG. 2) for pulmonary drug delivery, wherein the aerosol 3 comprises aerosol particles 30 containing an orally inhaled and/or nasal drug product 1. The (real) aerosol particles 30 are represented by discrete (modelled) aerosol particles 30'.

A (single) patient-specific tomographic image Img of the respiratory system 4 of a human individual is obtained by applying an imaging method, for example by making a (single) CT-scan of the specific respiratory system 4. Also other imaging methods as computed tomography (CT) can be used, in particular magnetic resonance imaging (MRI), ultrasound, X-ray or electro impedance tomography (EIT). The (human) individual can be healthy or a patient having a lung disease. The tomographic image Img is processed in a segmentation step, which is known in the prior art, resulting in processed image data representing the respiratory system 4. Then, a discretized respiratory-system structure 4' is derived from the processed image data. A computational lung model Lmod (lung model) based on the discretized respiratory-system structure 4' is generated and calibrated. Appropriate boundary conditions are derived for the lung model Lmod based on a respiration value Rval of a respiration parameter Rpar characterizing respiration of the human individual. The lung model Lmod is described in greater detail below with reference to FIG. 2.

The discretized respiratory-system structure 4' is based on a spatial segmentation of the structure of the airways 40 of the respiratory system 4 into a plurality of discrete spatially three-dimensional (tubular) airway segments 40'. The discrete airway segments 40' can be so-called finite elements of a FEM-discretization (FEM: Finite Element Method). As a next step, the transient gas flow Gvel in the airways 40, modeled by the plurality of discrete airway segments 40', is computed in a reduced-dimensional flow simulation, preferably as OD-flow.

Then, based on the transient gas flow velocity Gvel, in a one-way coupled approach, a computational particle transport and deposition model Pmod (particle transport and deposition model) is used to compute a spatial particle deposition distribution Ddist of a plurality of individual discrete particles 30' deposited in the airways 40, particularly in the lungs 42. Inhalation and exhalation of individual particles 30' is accounted for by the particle transport and deposition model Pmod. Individual discrete particles 30' are seeded into the computational domain and tracked individually according to a Lagrangian approach throughout the entire airway tree of the discretized respiratory-system structure 4'.

The plurality of discrete particles 30' individually tracked through the airway segments 40' represent aerosol particles 30 of an aerosol 3 containing an orally inhaled and/or nasal drug product 1, in particular an active ingredient of a drug administered, preferably for treatment of a lung disease. Orally inhaled and/or nasal drug products 1 are preferably intended for, but not limited to treatment of lung diseases and can particularly comprise cannabis (THC as active ingredient).

At least one aerosol value Aval of at least one aerosol parameter Apar characterizing the aerosol 3 is determined, preferably measured, obtained from a database or from specification data of an inhaler device 2, 2*a-d* for generating an aerosol 3. An aerosol value Aval can also be computed based on analytical relations of physical properties of the aerosol 3 or as a result of a computational simulation of a generation process and/or flow of the aerosol 3 in an inhaler device 2, 2*a-d*. For such a simulation, a computational inhaler device model Dmod can be used (see FIG. 3, and in particular FIG. 10*a-g*). Typical aerosol parameters can be the (mean) particle size, preferably a (mean) particle size distribution, particle density and/or an aerosol flow (mass flow or volume flow), which is preferably time-dependent relative to a respiration cycle of a human individual (patient-specific).

In a post-processing step, at least one efficacy value Eval of an efficacy parameter Epar is computed based on the spatial particle deposition distribution Ddist. In the example of FIG. 1, the efficacy parameter Epar indicates a set of different parameters, comprising the percentage of particles deposited in a targeted area of the lungs (Eval=12%), a mean on-target particle size [μm] (Eval=2.2 μm), the standard deviation of the on-target particle size [μm] (Eval=1.5 μm) and the absorbed drug amount in the targeted area [mg] (Eval=0.01 mg). Different kinds of efficacy values Eval and further specific examples are discussed below with reference to the Examples.

The efficacy value Eval can be used for automatically assessing the efficacy of pulmonary drug delivery. The efficacy value Eval can be stored, displayed and/or transmitted for further use in various technical applications. Particularly, the efficacy value Eval can be used to assess the efficacy and/or safety of an orally inhaled and/or nasal drug product 1 or for assessing the performance of an inhaler device 2, 2*a-d* for pulmonary drug delivery, e.g. during a design or testing process of the inhaler device 2, 2*a-d*.

Orally inhaled drug products 1 can comprise the examples of active ingredients described in the following. Currently many different formulations of orally inhaled drug products are approved by regulatory bodies for oral inhalation. Many existing end-consumer drug products are based on different active ingredients for different diseases. These active ingredients can be separated into the following main groups according to their key pharmacological groups: Inhaled bronchodilators are utilized to treat obstructive airway diseases such as Asthma and COPD. Subgroups of these inhaled bronchodilators include β2 adrenoceptor agonists (exemplary active ingredients include Epinephrin Albuterol, Terbutaline, Levalbuterol, Fenoterol, Aformoterol, Formoterol, Indacaterol, Olodaterol and Salmeterol) and muscarine acetylcholine receptor antagonists (exemplary active ingredients are Ipratropium, Tiotropium, Glycopyrronium, Aclidinium, Ume-clidinium, Revefenacin); Anti-inflammatory products include gluococorticoids to treat inflammation of lung tissue, for example in asthma. Active ingredients include Beclomethasone dipropionate, Budesonide, Ciclesonide, Flunisolide, Fluticasone furoate, Fluticasone propionate, Mometasone furoate; Also combination products are comprised, combining previously mentioned active ingredients to treat COPD and Asthma; Anti-infectives are used in infective diseases like tuberculosis, influenza, pneumonia, measles and severe acute respiratory syndrome. Active ingredients include Tobramycin, Aztreonam Lysinate, Levofloxacin, Colismethate sodium, Amikacin, Ribavirin, Pentamidine; Recombinant human Deoxyribonuclease (rhDNase) is a glycosylated 260-amino-acid protein used for the treatment of cystic fibrosis; Mannitol is a nonionic sugar alcohol in dry powder form utilized to increase the periciliary fluid layer. This medication induces coughing and therefore clears the respiratory airways in bronchiectasis and cystic fibrosis; Prostacyclins are utilized for pulmonary arterial hypertension (PAH) and include Iloprost and Treprostinil as active ingredients; Lung Surfactant is administered through oral inhalation to treat respiratory distress syndrome (RDS) especially in infants. Lung surfactant is either extracted from animal lungs or synthetically produced; Drugs for systemic therapies are utilized to treat systemic diseases which are not restricted to pure respiratory diseases. Active ingredients may include Nicotine, Loxapine, Levodopa (treatment for Parkinson disease) or Insulin (treatment for diabetes).

FIG. 2 illustrates the structure of the human lung and is used to explain the computational lung model Lmod in greater detail in the following.

Typically, medical literature distinguishes 23 airway generations of the human lung (see FIG. 3), comprising the trachea 46 (generation 0), the bronchi 47, comprising the main bronchi (generation 1), the lobar bronchi (generation 2) segmental bronchi (generations 3 and 4), and sub-segmental bronchi (generations 5-11), the bronchioles 48 (generations 12-19), including terminal bronchioles (generation 16) and respiratory bronchioles (generations 17-19) and the alveoli 49, including the alveolar ducts (generations 20-22) and alveolar sacs (generation 23). Usually, generations 1-16 are assigned to the conducting airways and generations 17-23 to the respiratory airways. Within the conductive airways, each generation corresponds to a level of bifurcation of the airways. The lungs 42 are located within the thorax 8 and above the diaphragm 43.

More specifically, the (human) airways 40 are divided into the trachea 46 and the bronchial system, which is divided into a right and a left main bronchial branch (main bronchus) and which supplies oxygen to one of the two lungs. Each bronchial trunk is further divided into smaller bronchi (bronchi of the second order): The right main bronchus usually branches into three main branches, which supply the usually three lobes of the right lung. The left main bronchus is usually divided into two main branches for the usually two lobes of the left lung. These five main branches form the so-called lobar bronchi, which branch out further to the segment bronchi and into ever smaller branches (generations). After about 22 levels of bifurcation (i.e., 23 generations), a widely branched system of the bronchial tree thus arises.

This system of bronchi 47 is available via the CT-image data set and can be converted into a 3D-structure data set or segmented, for example, by means of an image recognition algorithm based on artificial intelligence. This is then made available to the lung model for constructing the model geometry of the lung.

The smaller the bronchi become, the simpler and thinner their internal structure becomes. The smallest branches of the bronchi, the bronchioles 48, have an internal diameter of less than 1 mm. Therefore, the CT resolution is not sufficient to represent these structures in a spatially resolved manner. While the lower-generation airways are segmented directly from the CT data, the higher-generation airways are generated using a space-filling algorithm, as described, for example, in "Ismail M, Comerford A, Wall W A. *Coupled and reduced dimensional modeling of respiratory mechanics during spontaneous breathing*. International Journal of Numerical Methods in Biomedical Engineering 2013; 29:1285-1305". The airways (trachea and bronchial tree) are generated recursively from the generation in which segmentation from the CT data is no longer possible or earlier, until the peripheral airways reach a length termination criterion (e.g. 1.2 mm), a radius termination criterion (e.g. 0.2 mm) or a generation termination criterion (e.g. Ngen=17). The scaling of the radius of the daughter-to-parent branch of the left and right branch of the bronchial tree is 0.876 and 0.686, respectively, as is generally known from morphological studies of the human body. The radius scaling, the airway orientation and the airway length can be adapted as a function of the CT data spatially assigned to them in order to map the inhomogeneity of the lung. The segmented lower-generation respiratory tracts, which are based on the CT data, are connected to the higher-generation respiratory tracts which are generated using the space-filling algorithm. At the distal end of the generated airway tree, so-called terminal units are created that model the remainder of the airway system which may comprise alveoli 49, alveolar ducts, alveolar sacs and/or portions of the bronchioles 48. Together the terminal units form what is referred to as lung tissue 6 herein.

A lung model is understood below as a digital, i.e. computer-implemented, model of a human lung, which is suitable for simulating the physiology of a human lung. This may be a lung model Lmod, which is based on the CT data of a patient, i.e. is specific to the patient. Alternatively, the lung model Lmod can be based on the evaluation of CT data of a patient group or generally on the evaluation of lung data from a database. A patient-specific lung model Lmod can be calibrated to a patient, for example by calibrating the lung model by means of a real breath (volume) curve of the patient.

Output variables of the simulation based on the lung model Lmod comprise in particular the pressure P and the flow rates Q in each airway segment 40', but can further comprise the strain of the lung tissue and/or a surface-active factor of the alveoli surface.

The lung model Lmod takes into account (i) the airways 40, which consist of the trachea 46, as well as the bronchi 47 and bronchioles 48, (ii) the terminal units, and preferably (iii) the terminal-unit interaction, which takes into account the viscoelastic coupling of terminal units adjacent to one another. When inhaled, the lung volume increases, which causes the alveoli 49 to stretch, among other things. In this case, the alveoli 49 which are adjacent to one another are linked in their expansion owing to the lung tissue 6 which connects them to one another.

By means of terminal-cluster linker elements, the interaction of adjacent terminal units and between terminal units and respiratory tracts is modelled. These terminal-cluster linker elements link in pairs or in groups those terminal units (and respiratory tracts) which influence each other. This interaction is caused by the volume competition of neighboring alveoli/alveolar sacs within the lung tissue 6. The resulting mutual influence is realized by additional forces at the terminal units (and respiratory tracts) connected to the terminal unit linker element. As a result, terminal units can be stretched even if the pressure is exerted only on the subpleural terminal units. In other words, the boundary condition of the pleural pressure is only applied to those terminal units actually adjoining the pleural gap.

The lung model Lmod takes into account the three-dimensional geometric structure of a patient's lung. For this purpose, a data set which forms the 3D structure geometry of a patient lung (discretized respiratory-system structure 4'), is read into the lung model Lmod as an input variable.

In one embodiment, the data set can alternatively be averaged over the structural geometry of a plurality of patients. For example, an averaged structural data set (averaged discretized respiratory-system structure 4') can be generated for patients with a certain pre-existing lung disease and can be read into the lung model Lmod for assessing the efficacy of pulmonary drug delivery to that specific lung.

The lung model Lmod follows an approach in which the pressure difference $\Delta P$ along an airway segment 40' is represented as a linearly dependent variable of the flow resistance R and of the flow rate Q through the respiratory tract channel as $\Delta P = Q*R$.

More details and a mathematical description of the lung model Lmod are specified in WO 2021/204931 A1 and references cited therein.

The lung model Lmod represents the entire human lung encompassing also the elasticity of the airway walls 50 and the lung (alveolar) tissue 6. Consequently, the lung model Lmod also accounts for exhalation due to consideration of the resilient reaction forces compressing the lungs during exhalation.

Figure 3:
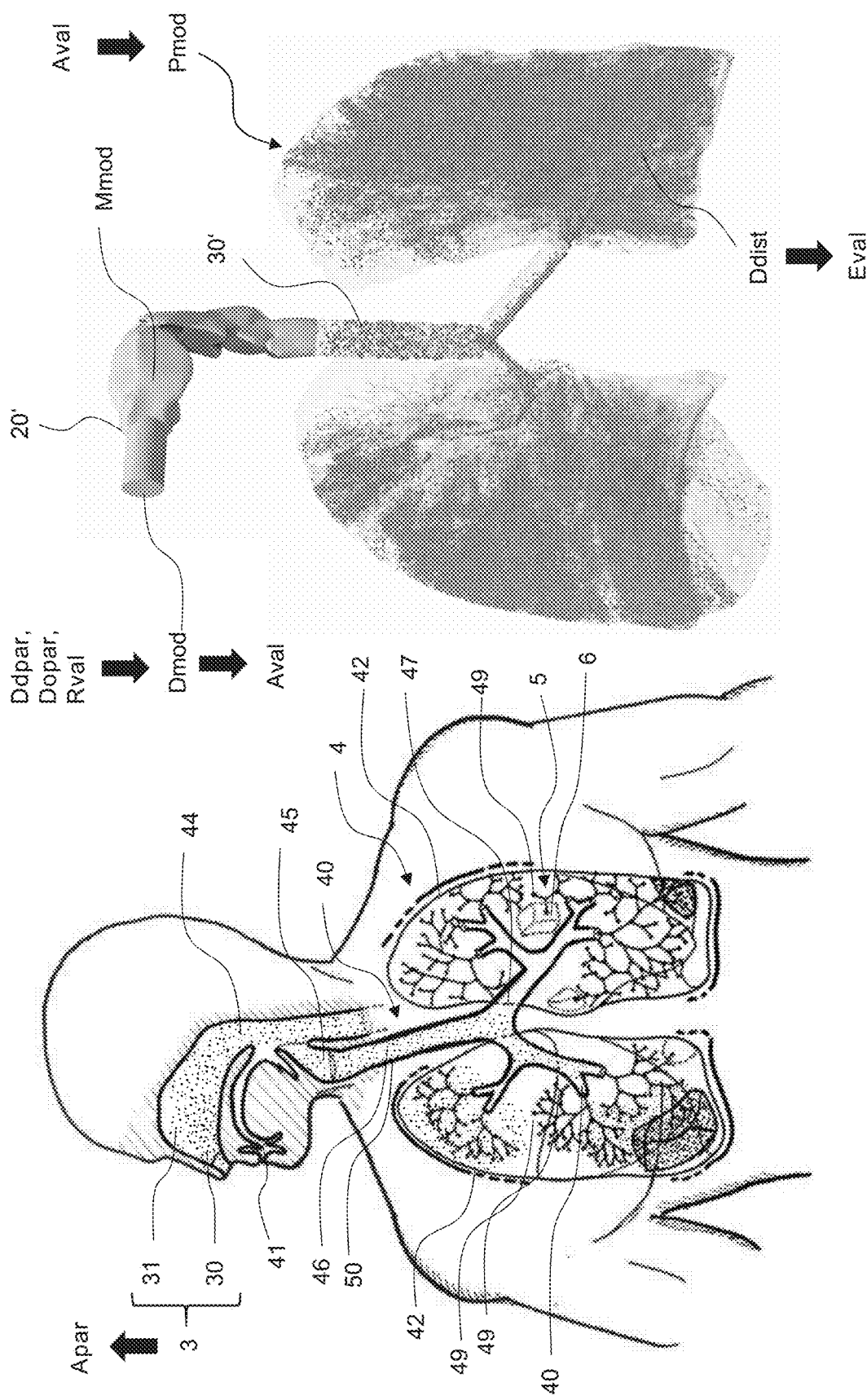

FIG. 3 shows the spatial particle deposition distribution Ddist computed based on the computational particle transport and deposition model Pmod in more detail.

The computational inhaler device model Dmod represents aerosol flow in a mouthpiece 20 (discretized mouthpiece 20') of an inhaler device 2, 2a-c and the computational mouth model Mmod accounts for aerosol flow in the region of the mouth 41, pharynx 44 and larynx 45. Dmod and Mmod can be based on a CFD model taking into account particle transport, preferably a 3D-CFPD model.

The method comprises a step of seeding individual discrete particles 30' into the gas flow in the airways 40. Seeding of particles can be understood as initializing (new) particles that shall enter the computational domain. It is important that particle transport is represented and solved in 3D space by as explained in further detail below. At discrete points in time, individual discrete particles 30' are seeded in (at least one location of) the lung model domain, preferably in an inflow cross-section of the trachea 46, by initializing at least one Lagrangian particle 30' with its corresponding position, velocity, acceleration, density, mass, drag coefficient, radius or shape information and corresponding dimensions. The number of seeded particles and their individual properties and seeding times can be determined in several different ways to match the real aerosol characteristics at the seeding location, for instance from (any combination of): directly specified list of values; measured values obtained from an experiment; values determined as the result of another computer model and simulation, e.g., including the aerosol generation process and/or flow and/or the upper airways; values determined as the solution of an analytical model, e.g., including the aerosol generation process and/or flow and/or the upper airways; and randomly generated values satisfying a statistical distribution obtained by any of the previous options.

For illustration purposes, two specific use cases shall be described in greater detail. Given a time-dependent aerosol mass rate, time-dependent particle size distribution (e.g. log-normal distribution with mass median diameter and geometric standard deviation as measured for the inhaler in an experiment), constant particle density and spherical shape of the particles, an ensemble of discrete particles 30' is generated by randomly assigning a diameter drawn from the log-normal distribution and assigning/computing the remaining properties such as density, mass and drag coefficient. The particle generation for the currently considered discrete time interval is stopped as soon as the target aerosol mass for this time interval is reached. The specific seeding location of each of the particles within the cross-section at the trachea entry, i.e. inflow, is randomly chosen based on the assumption of an equal distribution of particles per cross-section area.

Figure 4:
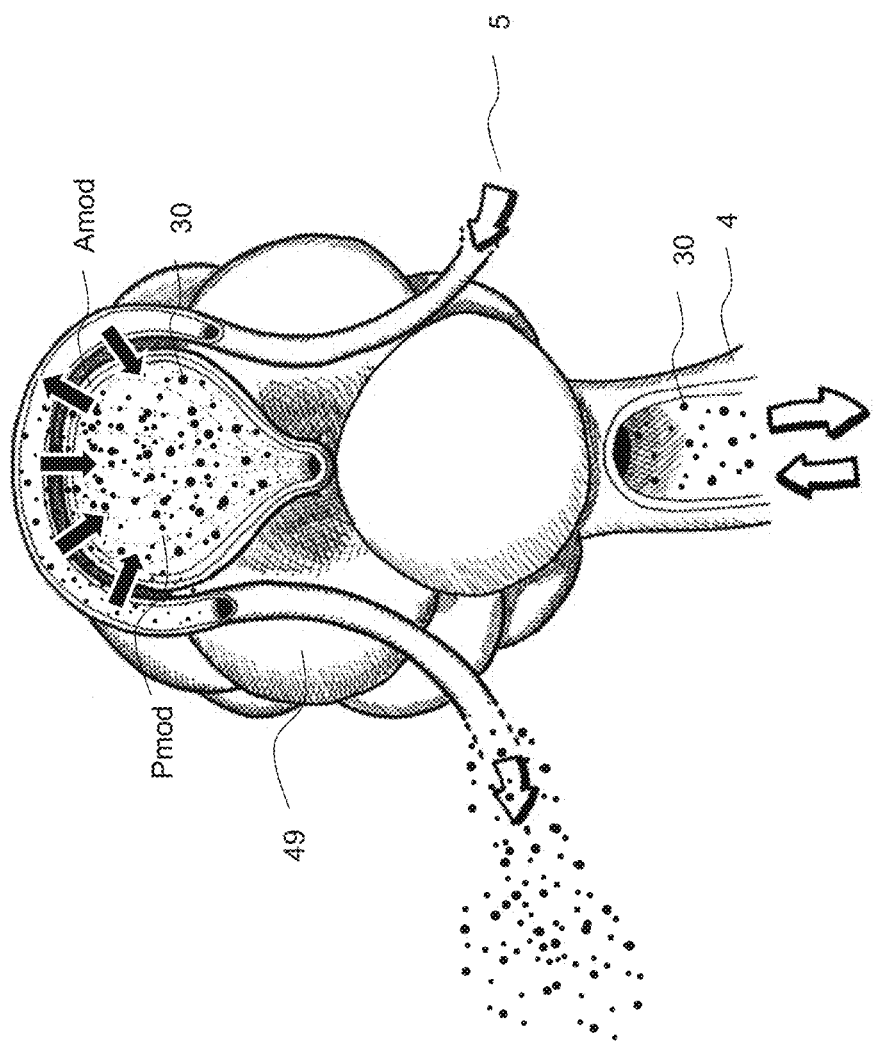

FIG. 4 illustrates the particle transport and deposition of aerosol particles 30 on the level of the alveoli 49 using the computational particle transport and deposition model Pmod. The aerosol particles 30 contain a predetermined dose of an active ingredient of the orally inhaled and/or nasal drug product 1, which can be absorbed into the blood circulation 5 in the alveoli 49. A computational absorption model Amod is evaluated to account for absorption of the active ingredient contained in aerosol particles 30, which have been deposited in the alveoli 49, i.e. in terminal units comprising the alveoli 49, into the blood circulation 5. The computational absorption model Amod is preferably based on pharmacometric modelling, in particular on first-order, Michaelis-Menten, or parallel first-order plus Michaelis-Menten kinetics. Pharmacometric modelling allows to assess drug concentration at any point in time, e.g., in plasma as well as drug effect. The efficacy parameter Epar can be indicative of a blood concentration (e.g. [mg/ml]) of the active ingredient in the blood.

Figure 5:
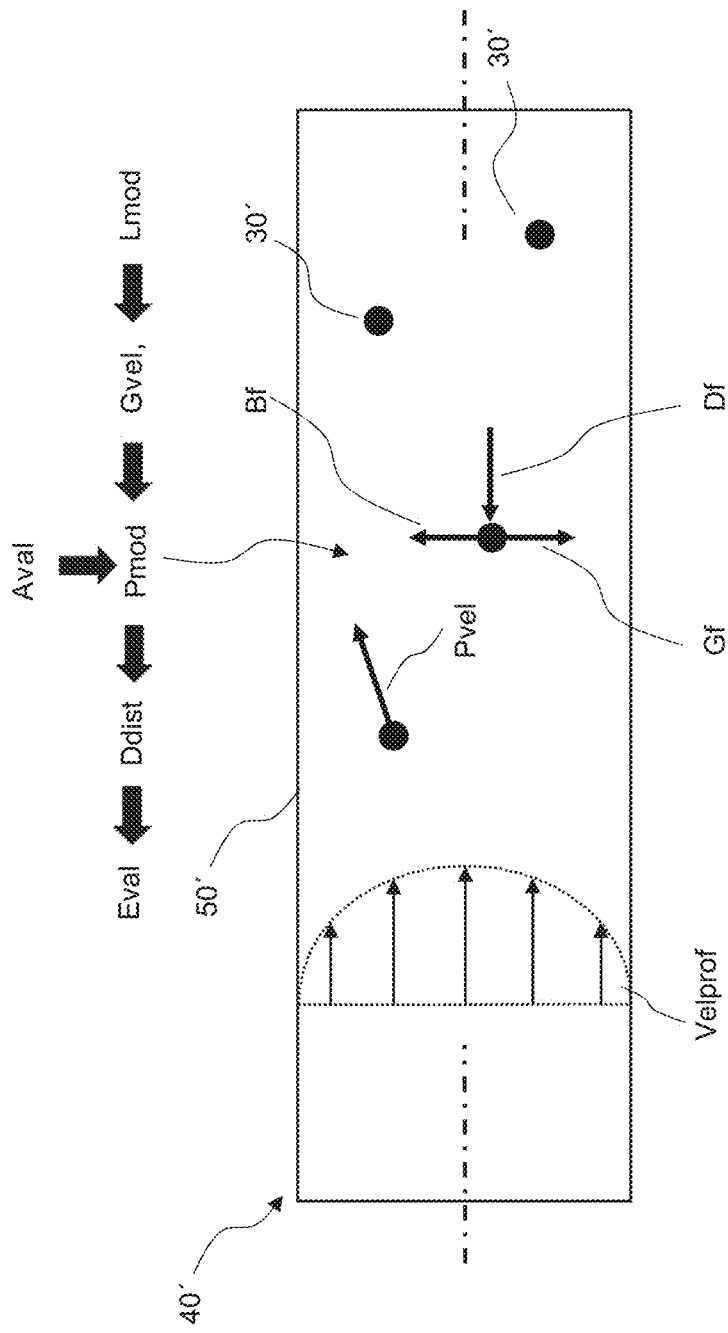

FIG. 5 illustrates how 3D particle transport through the airways is represented by a 0D-fluid field, which saves computing resources and renders the method computationally affordable although a high spatial resolution of the airway tree is considered. This important advantage of the method is achieved by utilizing 3D particle dynamics in a Lagrangian formulation for modelling the aerosol transport through airways 40. The information from the fluid field required to compute coupling forces on the discrete particles 30' (e.g. drag force Df, buoyancy force Bf, gravitational force Gf and optionally Brownian motion force BMf) is obtained by reconstructing the 3D fluid field from the solution of the reduced-dimensional fluid field. The computational particle transport and deposition model Pmod implements a Lagrangian approach to tracking individual discrete particles 30' transported by the gas flow Gvel. The Lagrangian formulation is a one-way coupled approach, meaning that the effect of the transient gas flow in the airways on the particles is considered, but not vice versa.

The reconstructed velocity profile Velprof is based on the assumption of a radially symmetric, parabolic flow profile in a cylindrical airway segment 40' (see FIG. 5). Given the radius of the airway segment and the volumetric flow rate and pressure at the inlet and outlet from the 0D fluid solution, the fluid velocity and pressure (as well as their gradients and other derived quantities) at any point in the 3D domain can be computed.

Alternatively, another set of assumptions can be used for the dimensional reduction from 3D to 0D and vice versa, e.g., conical airways or a different flow profile. But the concept of dimensional reduction of the fluid field, solving the reduced dimensional problem, and reconstruction of the full-dimensional fluid field for the purpose of calculating forces exerted on the transported particles remains the same.

Figure 6:
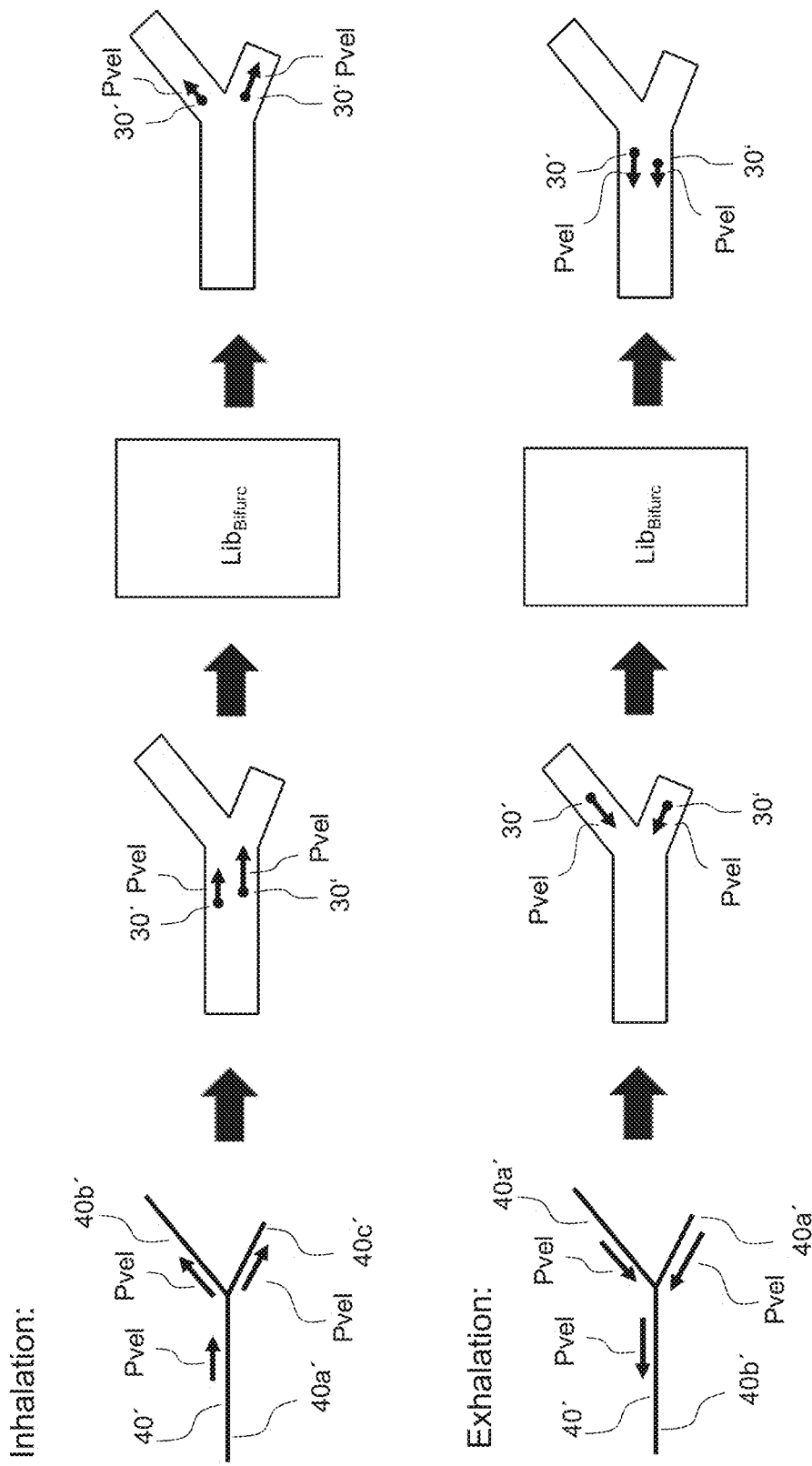

FIG. 6 illustrates the particle transfer approach between individual airway segments 40', 40a', 40b', 40c'. This dedicated approach for transferring discrete particles 30' across airway bifurcations is necessary since the 0D fluid field is discontinuous across the boundaries of individual airway segments 40', 40a', 40b', 40c'. When simulating a discrete particle 30' in a 0D-fluid consisting of individual airway segments 40' during inhalation, a transfer is initiated when the particle exits the upstream airway segment 40a'. The discrete particle can either be transferred into one of the downstream airway segments 40b' and 40c' using a pure geometric approach (geometric bifurcation criterion) or with additional information resulting from an interpolation approach using a bifurcation library $Lib_{bifurc}$. Similarly, particles are transferred in the reverse direction during exhalation when exiting either one of the downstream airway segments 40b' and 40c'.

Figure 7:
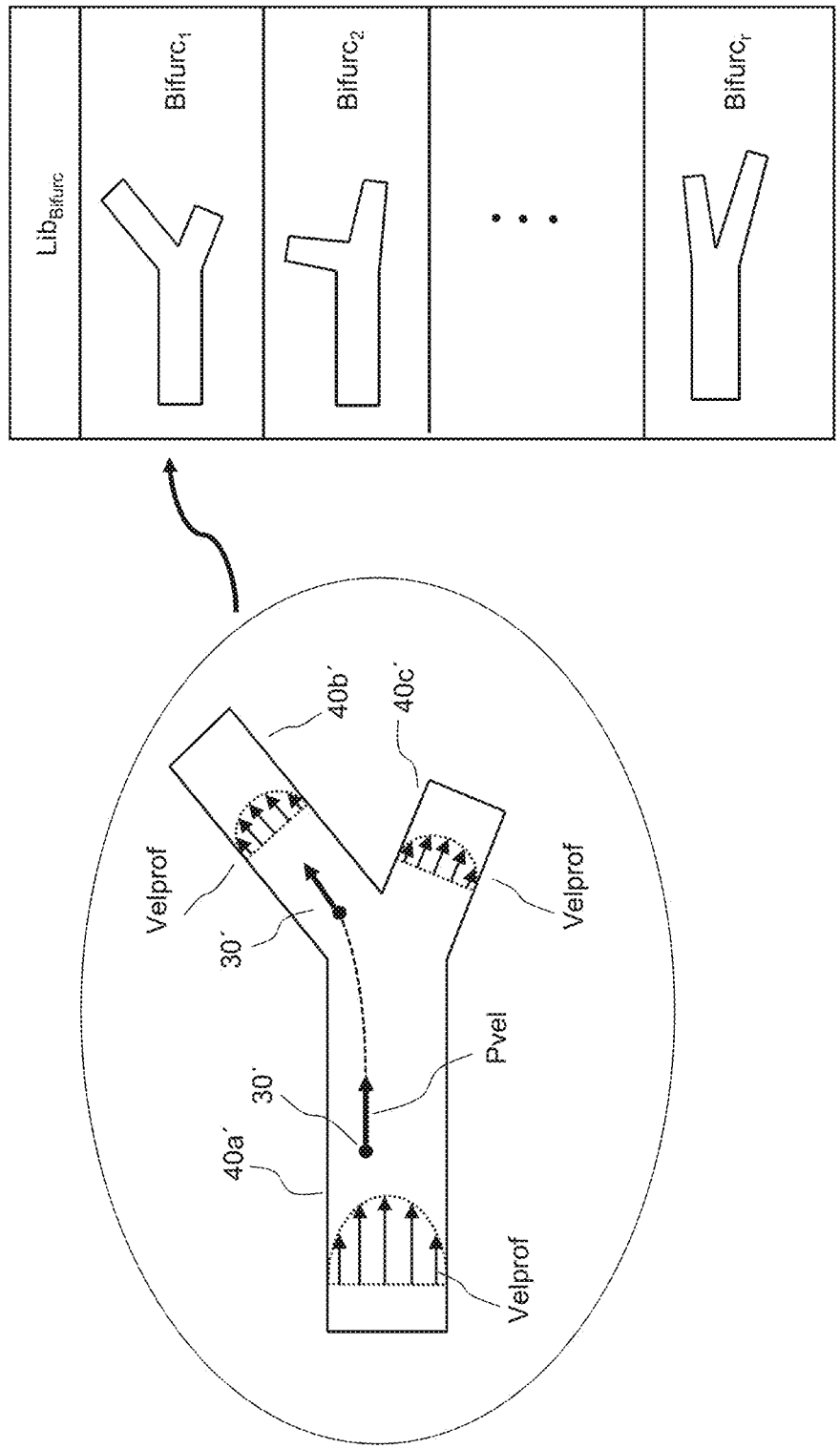

FIG. 7 illustrates the process of creating an airway bifurcation library $Lib_{bifurc}$ storing a plurality of different pre-computed airway bifurcation scenarios. The airway bifurcation library $Lib_{bifurc}$ can be used for the transfer of discrete particles 30' across airway bifurcations. This airway bifurcation library Lib bifurc contains pre-computed particle transfer information from numerous pre-computed 3D-CFPD simulations. These 3D-CFPD simulations include various differing flow regimes, bifurcation geometries and aerosol parameters Apar. This results in different pre-computed airway bifurcation scenarios (Bifurc1, Bifurc2, Bifurc3, . . . . Bifurcr). Pre-computed bifurcation scenarios can be based on relatively complex pre-computed three-dimensional simulations across bifurcations at high spatial and temporal resolution, preferably also taking account turbulent flow for various different geometries of the bifurcation. A pre-computed bifurcation scenario is preferably used for the more complex bifurcation scenarios in the inhalation flow direction, whereas a purely geometric bifurcation criterion can be used in the (reversed) exhalation flow direction.

Figure 8:
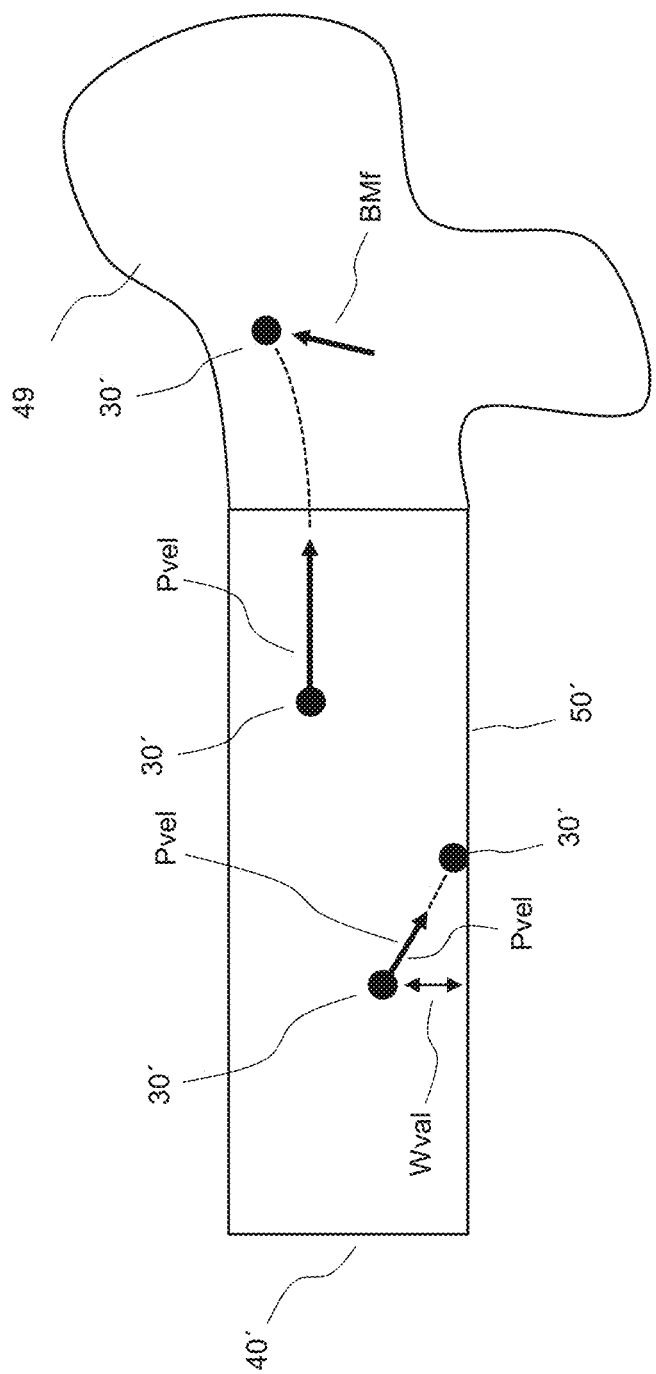

FIG. 8 is an exemplary illustration of the two particle deposition mechanisms which typically occur across the lung domain.

According to the first deposition mechanism, a deposition model based on different deposition criteria is evaluated for each discrete particle 30. The deposition model is preferably a sub-model (sub-routine) of the computational particle transport and deposition model Pmod. These deposition criteria include a comparison of the distance value Wval between a discrete particle 30' and the airway wall 50' of the airway segment 40' with a predefined deposition distance Dval. Deposition occurs if the distance value Wval is smaller than the deposition distance Dval. Further deposition criteria may include the current particle velocity Pvel, the angle of impact between the discrete particle 30' and the airway segment 40', the shape of the discrete particle 30' or attraction forces between the discrete particle 30' and the airway segment 40'.

The second deposition mechanism occurs when a discrete particle 30' reaches the end of a terminating airway segment 40'. The particle 30' is deposited in the associated terminal unit, which represents individual alveoli 49 or a larger region inside the lung.

The spatial particle deposition distribution Ddist is computed based on all deposited particles within the discretized respiratory-system structure 4' comprising the airway segments 40' representing the airways 40 and terminal units representing the alveoli 49.

FIG. 5 (FIG. 9) illustrates pharmacometric modelling for computing blood (plasma) concentration of the drug as an example of determining drug efficacy. Results from the particle transport and deposition simulation using Pmod, in particular a spatial particle deposition distribution Ddist, can be used as inputs for a subsequent pharmacometric model to assess drug exposure, i.e., drug concentration at any point in time, e.g., in plasma as well as drug effect. In particular, pharmacokinetic (PK) models can be used to relate local deposited dose to the time course of measured drug concentration in the body (usually the plasma)

Figure 9:
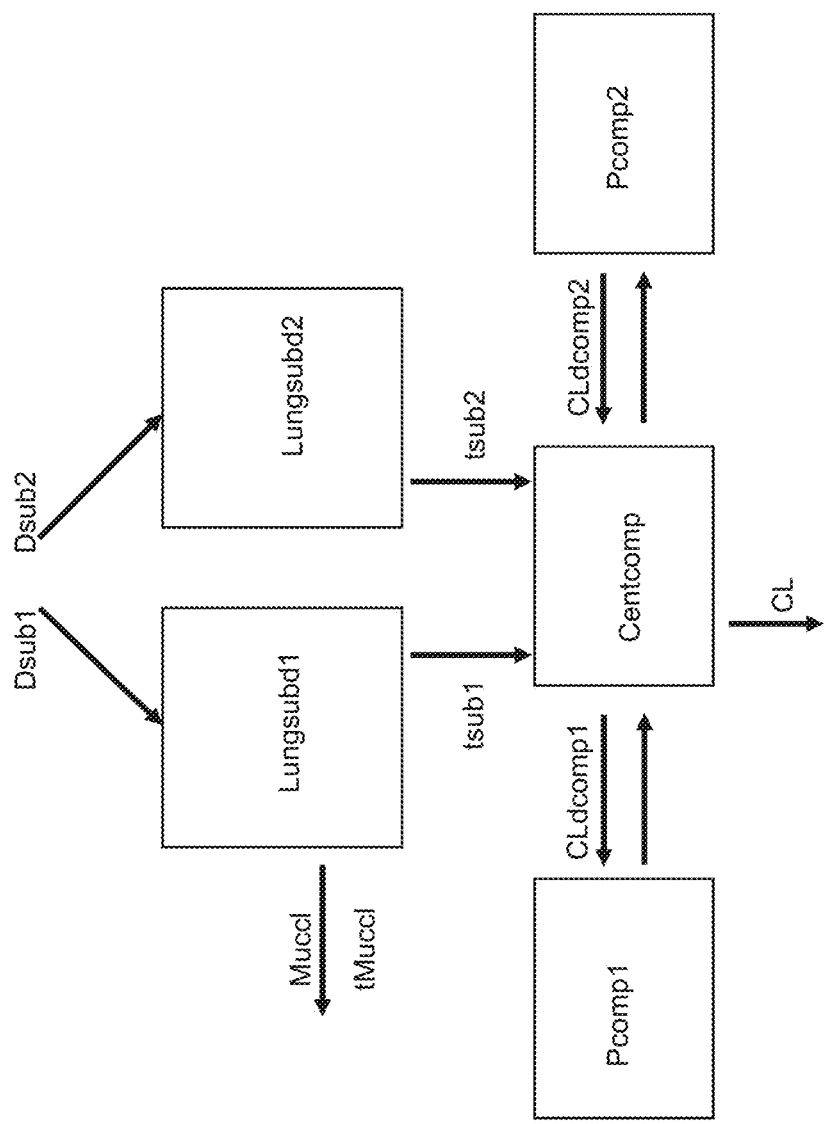

For the described method, a PK model with a compartmental structure with input and disposition models is used. The input model describes the time course of drug movement from a region or subdomain of deposition to the side of drug measurement, e.g., in plasma. The disposition model on the other hand describes time course of drug distribution, metabolism, and elimination from the body. One preferred variant is schematically depicted in FIG. 9.

Based on a computed spatial deposition distribution Ddist in the lung, the doses Dsub1, Dsub2, . . . , Dsubn of the active ingredient for arbitrary subdomains Lungsubd1, Lungsubd2, . . . . Lungsubdn of the lung model can be computed. These subdomains can be based on a spatial subdivision of the discretized structure of the respiratory system 4', e.g., a peripheral and a central region or based on airway generation, e.g., conducting airways and respiratory airways. For each lung subdomain Lungsubd1, Lungsubd2, . . . . Lungsubdn or compartment, absorption can be modelled through first order, Michaelis-Menten, or parallel first order plus Michaelis-Menten kinetics. Similarly, systemic disposition can be modelled by one or more compartments, a central compartment Centcomp and peripheral compartments Pcomp1, Pcomp2, as shown in FIG. 9. Mucociliary clearance Muccl can be modelled by a one or more separate first order elimination processes.

The parameters of the PK model, consisting of at least one or more absorption half-lives (tMuccl, tsub1, tsub2) and one or more clearances CLdcomp1, CLdcomp2, CL can be computed using state-of-the-art methods for population PK models as outlined in (Bauer R J, Guzy S, Ng C. *A survey of population analysis methods and software for complex pharmacokinetic and pharmacodynamic models with examples*. AAPS J. 2007; 9 (1): E60-E83. doi: 10.1208/aapsj0901007) in combination with data, preferably from measurements about the time course of plasma concentration of the drug.

Figure 10G:
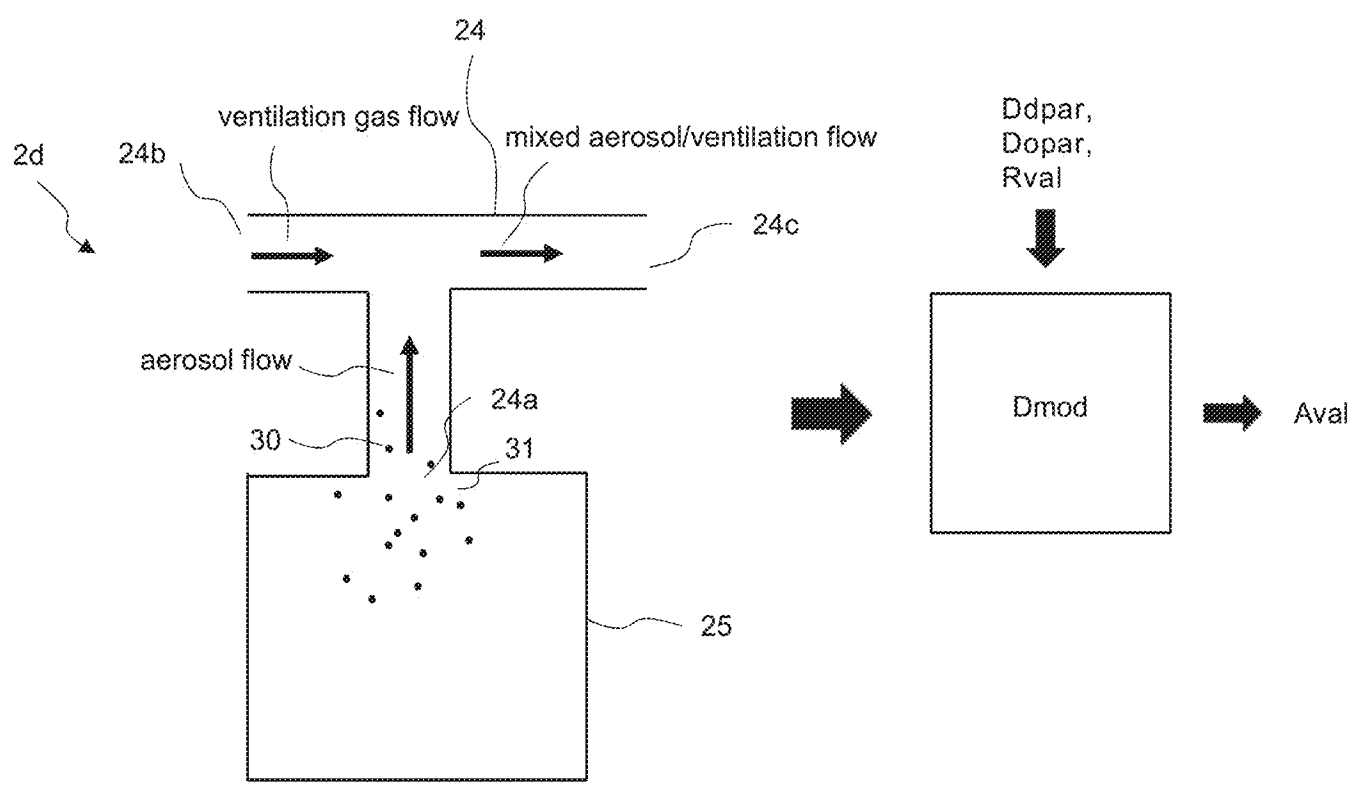

FIGS. 10a-10g show different inhalator devices 2, 2a-d that can generate aerosols 3 containing orally inhaled and/or nasal drug products 1 containing an active ingredient of the drug. The aerosol 3 contains a carrier gas 31 and aerosol particles 30 that can be inhaled by a person. FIGS. 10a and 10b show metered-dose inhalers 2a, FIG. 10c shows a dry powder inhaler 2a, FIGS. 10d-f show nebulizer inhaler devices and FIG. 10g shows a nebulizer device 2d including a ventilation tubing 24 for mechanical ventilation.

The generation process and flow of the aerosol 3 in the respective inhaler devices 2, 2a-d (inhaler) is represented by corresponding computational inhaler device models Dmod. An aerosol value Aval of an aerosol parameter Apar characterizing the aerosol 3 generated in the respective inhaler devices 2, 2a-d can be determined by simulating the generation and flow of the aerosol 3 using the computational inhaler device models Dmod. For example, the aerosol flow in the inhaler device 2, 2a-d can be computed using a 3D-CFD simulation on the discretized domain of the geometry of the inhaler device 2 and its components, e.g. obtained from a CAD model. The computed aerosol value Aval is then used as input for the computational particle transport and deposition model Pmod to determine efficacy of the aerosol 3 for pulmonary drug delivery.

The computational inhaler device models Dmod can depend on one or more inhaler design parameter Ddpar and/or inhaler operation parameter Dopar, which can differ according to the type of inhaler device 2, 2a-d. A respiration value Rval indicating a respiration parameter Rpar, such as an inhalation gas flow and/or a inhalation suction pressure, can be prescribed as a boundary condition for the computational inhaler device model Dmod at the outflow of the inhaler device 2, e.g. at an outflow opening of a mouthpiece 20, that is at a discretized mouthpiece 20' of the model Dmod.

FIG. 10a shows a metered-dose inhaler device 2b (inhaler), namely a pressurized metered-dose inhaler (pMDI). The inhaler 2b comprises a canister 21 and an actuator 27. The canister 21 includes a substance, which contains an orally inhaled drug product 1 (liquid) and a propellant 26, such that the substance is under pressure. The canister 21 further contains a valve 29. The actuator 27 comprises an actuator seat 28, a nozzle 22, and a mouthpiece 20. When the canister 21 (cartridge) is inserted into the actuator 27, the valve 29 is inserted into the actuator seat 28. When the canister 21 is pushed further towards the actuator 27, the valve 29 is pressed against the actuator seat 28, thereby activating the valve 29 and the entire drug product 1 (drug) or a portion thereof is released through the nozzle 22 in the form of aerosol particles 30. The aerosol particles 30 exit the actuator 27 through the mouthpiece 20.

FIG. 10b shows a metered-dose inhaler device 2b (inhaler), namely a breath-activated metered dose inhaler (BAMDI). The inhaler 2b comprises a canister 21 and an actuator 27. The canister 21 includes a substance, which contains orally inhaled drug product 1 (liquid) and a propellant 26, such that the substance is under pressure. The canister 21 contains a valve 29. The activated 27 comprises a lever 60, a first spring 61, a second spring 62, a vane 63, and activation mechanism 64, and actuator seat 28, a nozzle 22 and a mouthpiece 20. When the liver 60 is primed, the first spring 61 is tensioned and the canister 21 is pushed against the activation mechanism 64. When a negative pressure, in particular a suction pressure Rval, is applied at the mouthpiece 20, vane 63 is pulled towards the mouthpiece 20, thereby triggering the activation mechanism 64. When the activation mechanism 64 is triggered, the involved 29 is pressed against the actuator seat 28, thereby activating the valve 29 and releasing at least a portion of the drug product 1 through the nozzle 22 in the form of aerosol particles 30. The aerosol particles 30 exit the actuator 27 through the mouthpiece 20. While the activation mechanism 64 is triggered, the second spring 62 is under tension. When the negative pressure application at the mouthpiece 20 terminates, the second spring 62 deactivates the activation mechanism 64 and the release of aerosol particles 30 is stopped.

Several device design parameters Ddpar of metered-dose inhaler devices 2b can be varied to improve pulmonary drug delivery into certain regions of the lung. For example, the diameter and/or geometry of the nozzle 22 and/or the distance from the nozzle 22 to the mouthpiece 20 influences the particle size distribution. The pressure inside the canister 21 is a device operation parameter Dopar influencing the speed of the ejecting drug 1.

FIG. 10c shows a dry powder inhaler device 2a (DPI), which can be configured as a single-dose DPI, a multi-unit-dose DPI or a multi-dose DPI. The inhaler 2a comprises a canister 21 and an actuator 27. The canister 21 contains an orally inhaled drug product 1 in the form of a dry powder. A propellant 26 can also be contained in a pressurized canister 21. The actuator 27 comprises an actuator 71, a spring 61, a metering mechanism 70 and a mouthpiece 20. When the actuator cap 71 is pushed down, the metering mechanism 70 is activated and at least a portion of the drug 1 is released from the canister 1 as solid aerosol particles 30 through the mouthpiece 20.

The efficacy of the dry powder inhaler device 2a for pulmonary drug delivery can be influenced by adapting the particle size of the preloaded dry powder. The geometry of the mouthpiece 20 is a device design parameter Ddpar that can affect the flow rate of the aerosol 3, thus also influencing the speed of particles 30 when inhaled.

FIG. 10d shows a nebulizer inhaler device 2c (inhaler), namely a vibrating mesh nebulizer (VMN). The inhaler 2c can be configured as actively vibrating mesh nebulizer or passively vibrating mesh nebulizer. The inhaler 2c comprises a reservoir filled with a liquid orally inhaled drug product 1, here a canister 21, a mesh 80 (or membrane) and a mouthpiece 20. The mesh 80 can be connected to a power source (not shown). When the mesh 80 vibrates, a portion of the drug product 1 is nebulized and released through the mouthpiece 20 as a result particles 30 forming droplets. The mouthpiece 20 can be formed as an inhalation mask, through which a patient can brief through the mouth and/or nose.

FIG. 10e shows a different type of nebulizer inhaler device 2c (inhaler), namely a jet nebulizer (JN). The inhaler 2c comprises an aerosol generation chamber 23 containing a liquid orally inhaled drug product 1 and a mouthpiece 20. A gas source (not shown) for a carrier gas 31 forms a high-pressure gas jet 82 entering the aerosol generation chamber 23 from the bottom to generate aerosol particles 30 in the form of droplets. The aerosol particles 30 are released from the aerosol generation chamber 23 together with the carrier gas 31 as a flow of aerosol 3 through the mouthpiece 20. The inhaler to see may contain a baffle 81 having the purpose to deflect larger aerosol particles, thus generating an aerosol 3 with relatively small particles (droplets) 30.

FIG. 10f shows another type of nebulizer inhaler device 2c (inhaler), namely an ultrasound nebulizer (UN). The inhaler 2c comprises an aerosol generation chamber 23 containing a liquid orally inhaled drug product 1 (drug) and a mouthpiece 20. When the vibrating component 83 vibrates, at least a portion of the drug product 1 is nebulized into aerosol particles 30. The vibrating component may comprise or be a piezoelectric crystal. The aerosol particles 30 are release from the generation chamber 23 through the mouthpiece 20. The inhaler 2c may further include a baffle 81 to deflect larger aerosol particles 30 and prevent them from leaving the generation chamber 23.

The efficacy of nebulizer inhaler devices 2c, also called soft-mist inhalers (SMIs), for pulmonary drug delivery could be improved by adapting, in particular optimizing, certain device operation parameters Dopar, scu as frequency at which vibrating mesh nebulizers (VMNs) or ultrasound nebulizers (UMs) operate. Furthermore, device design parameters Ddpar, such as the geometry of the mouthpiece 20 and/or the baffle 81 as well as the dimensions of the aerosol generation chamber 23 can be chosen appropriately during a design process of an inhaler device 2c in order to influence aerosol parameters Apar and thus improve efficacy of the inhaler 2c for pulmonary drug delivery. Surface tension and/or viscosity of a specific liquid drug product 1 may also influence the aerosol generation (nebulizing) process and consequently the properties of the generated aerosol 3, in particular the size (diameter) of the particles 30.

Nebulizer inhaler devices 2c can further comprise an aerosol storage chamber and an inhalation valve and/or exhalation valve, wherein the aerosol storage chamber can collect and temporarily store a volume of already generated aerosol while the patient exhales. The exhalation valve can be integrated into a mouthpiece 20.

For spinning-disk inhaler devices (not shown), the efficacy of drug delivery can be influenced by setting the rotational speed of the disk as a device operating parameter Dopar and/or choose an appropriate groove geometry on the spinning disk as a device design parameter Ddpar.

FIG. 10g shows an inhaler device 2d comprising a ventilation tubing (24) for administering orally inhaled and/or nasal drug products to mechanically ventilated patients. The ventilation tubing comprises a first inlet for an aerosol flow and a second inlet for a ventilation gas (air or oxygen) flow generated by a ventilation device (not shown). The ventilation tubing 24 has a common outlet 24c for the mixed aerosol/ventilation flow. The aerosol 3 is generated by a nebulizer device 25, which can function according to the aerosol-generation principles of any of the previously describes nebulizer inhaler devices 2c or other nebulizer types. The ventilation gas flow takes up the aerosol from the outlet of the nebulizer device 25. A setting of the ventilation device determining the ventilation gas flow can be a device operation parameter Dopar influencing the aerosol flow at the common outlet. The nebulizer device 25 is integrated into the ventilator tubing 24 inserted into the patient's respiratory system for mechanical ventilation. The aerosol enters the patient's respiratory system at the outlet of a ventilation tube. Such an inhaler device 2d allows for administering orally inhaled and/or nasal drug products 1 to mechanically ventilated patients and consequently unable to breath (inhale) actively.

FIG. 11 illustrates different methods comprising method steps for assessing pulmonary drug delivery, in particular according to the method shown in FIG. 1. Similar as explained with respect to FIG. 1, an inhaler device 2 is used to generate an aerosol 3 from an orally inhaled drug product 1, which can be a liquid to be nebulized or a dry powder, for example. The aerosol 3 consists of liquid (droplet particles of liquid substance) or solid (powder particles) aerosol particles 30 and a carrier gas 31. An aerosol parameter Apar physically characterizes the aerosol 3. A tomographic image Img, e.g. a CT-scan, of an individual (human) respiratory system 4 comprising the lung is the basis of a computational lung model Lmod. A respiration value Rvar of a respiration parameter Rpar characterizing respiration behavior (respiration characteristics) of the respiratory system 4 is derived from measurement of a breathing curve of the individual (patient). The breathing curve can be a time curve of the inhaled and exhaled air volume during a full respiration cycle of the individual (patient). The measurement is preferably carried out using a spirometer. A computational device model Dmod is derived depending on the structure of the inhaler device 2. Dmod depends on, i.e. is parameterized by, device design parameters Ddpar and/or device operation parameters Dopar. The computational device model Dmod is used to simulate the generation and/or flow of an aerosol 3 containing individual discrete aerosol particles 30'.

The aerosol value Aval of the aerosol parameter Apar is determined based on the simulation of the inhaler device 2 using the computational device model Dmod. Alternatively (see dotted arrow Aval in FIG. 11), instead of or in addition to modelling aerosol flow in the inhaler device 2, one or more aerosol value(s) Aval can be determined by other means, for example by measuring the aerosol parameter Apar of the aerosol 3. For measurements of particle sizes or particle size distributions of the aerosol 3, for example, preferably optical and/or aerodynamic methods are applied, e.g. using a laser aerosol spectrometer or an aerodynamic particle sizer. The aerosol value Aval could also be obtained from a database containing data indicating physical properties of the aerosol 3 or from specification data of the inhaler device 2 and the type of aerosol 3 it generates, in particular depending on specific inhaler operation parameter settings.

Based on the gas flow velocity Gvel in the discretized airways 40' computed using the lung model Lmod, the computational particle transport and deposition model Pmod computes the spatial particle deposition distribution Ddist, preferably a local spatial density of deposited aerosol particles in different areas of the respiratory system 4, in particular the lung. One or more value(s) Eval of an efficacy parameter Epar is computed based on the spatial particle deposition distribution Ddist. The efficacy parameter Epar is preferably indicative of a local effective dose of the drug product 1, for example a blood concentration of the active ingredient of the drug product 1 in the blood circulation 5 or a tissue concentration in the lung tissue 6. Such a blood concentration Eval can be computed based on Ddist using an additional absorption model Amod. A predetermined minimum efficacy value Eval_min can define a lower threshold of a desired efficacy of pulmonary drug delivery above which a desired medical effect of the active ingredient is observed. A predetermined maximum efficacy value Eval_max can define an upper threshold of a desired efficacy of pulmonary drug delivery above which an undesired effect of the active ingredient is observed, in particular undesired side effects or even a toxic effect. Preferably, Eval is in between Eval_min and Eval_max for an aerosol value Aval well-suited for pulmonary drug delivery.

Efficacy of the orally inhaled drug product 1 for pulmonary drug delivery, in particular of the active ingredient contained in the orally inhaled drug product 1, is automatically assessed, e.g. using a computer, based on the efficacy value Eval. In particular, Eval could be stored in a storage device (not shown), displayed using a display device (not shown) and/or transmitted via a transmitting device (not shown), e.g. via mobile communication, for being used or further processed at a different location, in particular of a local or remote computer network.

In one embodiment, the efficacy value Eval can be used for producing an orally inhaled drug product 1, e.g. by producing a dry powder having a mean particle size corresponding to Aval, if the value Aval is well-suited for pulmonary drug delivery based on the assessment of Eval. The particle size characterizing the dry powder corresponds to a mean grain size of solid particles of the dry powder of the drug product 1. The formulation of the drug product 1 can contain excipients in addition to the active ingredient.

In further embodiments, the efficacy assessment could be used for producing, designing and/or operating and inhaler device 2 such that it generates an aerosol 3 characterized by the value Aval, in particular by choosing design parameters (e.g. a nozzle diameter) appropriately such that the inhaler device 2 generates an aerosol 3 with an aerosol parameter Apar corresponding to Aval.

Besides from the previously described advantages of the method, the method can be applied for the assessment of drug/device combination products 7 comprising an orally inhaled drug 1 and an inhaler device 2, 2a-d. An example of a drug/device combination product 7 is a nebulizer inhaler device 2c with a canister 21 pre-filled with an orally inhaled drug product 1 in liquid form. The drug product 1 is to be nebulized by the inhaler device 2c to generate an aerosol 3 having a desired particle size well-suited for pulmonary drug delivery according the assessment based on Eval. In particular, in the first stages of the development and regulatory approval process for new drug-device combination products, the method shown in FIG. 11 can provide reproducible, digital evidence that a new drug/device combination product 7 based on the same active ingredient as an approved drug product will result in the same effective lung dose and similar spatial aerosol particle deposition distributions. For example, a number of different patient-specific lung models Lmod can be used to define a digital patient cohort and then carry out an in-silico study according to the described method to compute digital biomarkers to predict or optimize target-effectiveness, dosing ranges or population restrictions.

If the described method is recognized by regulatory bodies, it can also be applied in later stage clinical trials to provide augmentative or supplementary information in the regulatory approval of pharmaceutical products. In addition, given a set of candidates of inhaler devices 2, the best inhaler device 2 for a combination with a given drug product 1 to achieve drug delivery to a certain target region of the lung can be selected. Information to modify a given inhaler device 2 or the associated inhalation protocol can be provided as well.

FIG. 12 illustrates absorption of an active ingredient 32 of an orally inhaled and/or nasal drug product 1 based on pharmacokinetic modelling. A detailed view of the airway wall 50 explains the pharmacokinetic absorption model underlying the computational absorption model Amod. While other possible absorption models, like the previously described pharmacometric model (see FIG. 9), are based on heuristics, pharmacokinetic absorption models describe the transport of the active (pharmaceutical) ingredient 32 (Active Pharmaceutical Ingredient: API) contained in aerosol particles 30 deposited in a segment of the airways 40 through the airway wall 50 and further into the blood circulation 5 by modelling the physical laws of pharmacokinetics (PK).

The airway wall 50 shown in FIG. 12 comprises the following layers: a pulmonary lining fluid 51 (mucus for conducting airways or alveolar lining fluid in the alveolar space), lung tissue (pulmonary tissue) 6, which can be alveolar tissue or conducting airway tissue, and the (systemic) blood circulation 6 (blood plasma). The computational absorption model Amod models how aerosol particles deposited in the respiratory system 4—and the (molecules of the) active ingredient 32 contained therein—are absorbed in the lung tissue 6 and in the (systemic) blood circulation 5. The computational absorption model Amod may model how deposited particles 30 are transported within the airway tree towards the mouth-throat region due to mucociliary clearance 52. The present computational absorption model (Amod) illustrated in FIG. 12 represents the processes of mucociliary clearance 52, dissolution 53 of the active ingredient in a pulmonary lining fluid 51, absorption 54 of the active ingredient in the lung tissue 6 and disposition 55 of the active ingredient from the lung tissue 6 into the blood circulation 5. The lung (pulmonary) tissue 6 may further be divided into one or more sub-layers including: epithelium, interstitium, basement membrane, and endothelium. The computational absorption model Amod may also model the absorption of an active ingredient from the mouth throat region into the systemic blood circulation 5 via the gastrointestinal tract. In the computational absorption model Amod, the airways 40 are represented by the airway segments 40' of the discretized respiratory-system structure 4' and the discretized airway wall 50' and the absorption process is based on the dose of active ingredient 32 contained in deposited discretized particles 30'.

The present embodiment of the computational absorption model Amod computes at least one efficacy value Eval of at least one efficacy parameter Epar based on the particle deposition distribution Ddist and the at least one absorption value Sval. For example, the efficacy parameter Epar can be a, preferably time-depend-ent, spatial concentration distribution Cdist of the active ingredient 32 of an orally inhaled drug product 1 in the lung tissue 6. The one or more efficacy value Eval, Eval1, Eval2 can be a, preferably time-dependent, local concentration value Cval1, Cval2, Cval3 of the active ingredient 32 in one specific region of the lung tissue 6, also denoted as Cuis in the following. Alternatively or in addition, an efficacy parameter Epar and its efficacy values can also indicate a, preferably time-dependent, (local) concentration of the active ingredient 32 in the blood circulation 5.

In the following, the pharmacokinetic modelling of the different physical subprocesses involved in the absorption of the active ingredient in the lungs as implemented in an embodiment of the computational absorption model Amod are explained. The computational absorption model Amod represents mucociliary clearance 52, dissolution 53 of the active ingredient 32 (contained in a solid/liquid aerosol particle 30) in a pulmonary lining fluid 51, absorption 54 of the active ingredient 32 in the lung tissue 6 and disposition 55 of the active ingredient 32 from the lung tissue 6 into the blood circulation 5. This embodiment is based on a physiologically structured population model (PSPM) according to "Hartung N, Bor-ghardt J. *A mechanistic framework for a priori pharmacokinetic predictions of orally inhaled drugs*. PLOS Computational Biology (2020); 16: e1008466". Efficacy values Eval of the efficacy parameters Epar are computed based on the spatial particle deposition distribution Ddist and at least one absorption value Sval, Sval1, Sval2 of at least one absorption parameter Spar. Geometric absorption pa-rameters Spar can be derived from the discretized respiratory-system structure 4'. Other absorption parameters Spar can be obtained from measurements and/or databases.

The spatial particle deposition distribution Ddist can comprise, preferably averaged, subdomain-specific particle deposition distributions in a plurality of subdomains Lungsubd1, Lungsubd2, . . . , Lungsubdn of the discretized respiratory-sys-tem structure 4' (i.e. local spatial particle deposition distributions). Efficacy values Eval, Eval1, Eval2 of the one or more efficacy parameters Epar are deter-mined depending on at least one of the subdomain-specific particle deposition distributions. A different subdomain-specific particle deposition distribution Ddist can be determined and used for each subdomain. A subdomain-specific particle deposition distribution Ddist can be derived from a spatial distribution of the density of deposited aerosol particles (particle sizes) in different areas of the discretized respiratory system 4', preferably by averaging over the subdomain (also referred to as "reduced" particle deposition distribution). The (local) subdomain-specific particle deposition distributions are derived from the (global) particle deposition distribution Ddist obtained based on Pmod (see method illustrated in FIG. 1).

In a preferred employment, each subdomain Lungsubd1, Lungsubd2, . . . , Lung-subdn represents a specific generation of the (conducting) airways 40 (generational depth x), in particular a specific generation of an airway segment 40', or to the alveolar region of the alveoli 49. For example, typically in a subdomain of a lower airway generation deposited discretized particles 30' (on average) have larger particle sizes, whereas in a subdomain of a higher airway generation de-posited discretized particles 30' (on average) have smaller particle sizes. Other subdomain-specific particle deposition distributions Ddist can be derived for subdomains belonging to a healthy region or to a pathological region of the discretized respiratory system 4' or a specific lobe of the lungs 42.

In a particularly preferred embodiment, a reduced particle deposition distribution Ddist for subdomains of the conducting airways 40' comprises the generational depth x (i.e. the airway generation that the particle is located in) and the geo-metric particle volume s. A reduced particle deposition distribution Ddist for subdomains of the alveolar region comprises the (averaged) geometric particle volume s of the particles 30' deposited therein.

In a preferred embodiment of the pharmacokinetic computational absorption model Amod, the process of mucociliary clearance is modelled according to the equation $$\frac{dx}{dt}(t) = -0.8791 \frac{cm}{min} \cdot \left(\frac{r^{br}(x)}{1\, cm}\right)^{2.808}$$

using the airway radius rbr (including lining fluid and typically in cm) at generational depth x. The generational depth x refers to a specific generation of the (conducting) airways 40 or of an airway segment 40', respectively, hence indicating a spatial dimension. The at least one absorption parameter Spar includes the airway radius rbr. The at least one efficacy parameter Epar may include the amount or fraction of the active ingredient 32 removed from the lung due to mucociliary clearance 52.

In this embodiment, the process of dissolution 53 of the active ingredient 32 into the pulmonary lining fluid 51 is modelled according to the equation $$\frac{ds}{dt}(t) = -\frac{4rr\, k_{diss}}{\left(\frac{4}{3}rr\right)^{1/3} p} \cdot \left(1 - \frac{C_{flu}}{C_s}\right) \cdot s^{1/3}$$

using the particle density p (preferably in M=mol/L), the saturation solubility $C_s$ (typically in M=mol/L, µM=$10^{-6}$ mol/L, or nM=$10^{-9}$ mol/L), the local maximum dissolution $k_{diss}$=D*$C_s$ (typically in nmol/cm*min) using diffusivity D, and the local concentration of the active ingredient 32 in the pulmonary lining fluid 51 $C_{flu}$ (typically in M=mol/L, µM=$10^{-6}$ mol/L, or nM=$10^{-9}$ mol/L). Herein, "local" refers to one or more of: in the alveolar region, in the conducting airway region, or at a certain generational depth x. In this embodiment, the at least one absorption parameters Spar include the particle density p, the saturation solubility $C_s$, and the maximum dissolution rate $k_{diss}$. The at least one efficacy parameter Epar may include the local concentration of the active ingredient in the pulmonary lining fluid 51 $C_{flu}$.

In this embodiment, the process of absorption 54 from the pulmonary lining fluid 51 into the lung tissue (pulmonary tissue) 6 is modelled according to the equation $$k_a = P_{app} \cdot SA \cdot \left(C_{flu} - \frac{C_{tis}}{K_{pu,tis}}\right)$$

using the effective permeability $P_{app}$ (typically in $^{cm}$), the airway surface area SA (typically in $m^2$), the lung-to-unbound plasma partition coefficient $K_{pu,tis}$ (typically unitless), the absorption rate between pulmonary lining fluid 51 and lung tissue 6 $k_a$ (typically in $^{mol}$), the local concentration of the active ingredient in the pulmonary lining fluid 51 $C_{flu}$ $$\left(\text{typically in M} = \frac{mol}{L},\, \mu M = 10^{-6}\frac{mol}{L},\, \text{or nM} = 10^{-9}\frac{mol}{L}\right),$$

and the local concentration of the active ingredient in the lung tissue $C_{tis}$ (typically in $$M = \frac{mol}{L},\, \mu M = 10^{-6}\frac{mol}{L},\, \text{or nM} = 10^{-9}\frac{mol}{L}\right).$$

Herein, the "local" refers to one or more of: in the alveolar region, in the conducting airway region, or at a certain generational depth x. In this embodiment, the at least one absorption parameter Spar the effective permeability $P_{app}$, the airway surface area SA, and the lung-to-unbound plasma partition coefficient $K_{pu,tis}$. The at least one efficacy parameter Epar may include the local concentration of the active ingredient in the pulmonary lining fluid 51 $C_{flu}$ and/or a local concentration of the active ingredient in the lung tissue 6 $C_{tis}$ (also denoted as Cval1, Cval2, Cval3).

In this embodiment the process of absorption 55 of the active ingredient from the lung tissue 6 in to the systemic blood circulation 5 is modelled according to $$k_{sys} = Q \cdot \left(\frac{BP \cdot C_{tis}}{K_{p,tis}} - C_{sys}\right)$$

Using the local perfusion/blood flow Q (typically in L/h), the blood-to-plasma ratio in the lung BP (typically unitless), the local concentration of the active ingredient 32 in the lung tissue 6 $C_{tis}$ $$\left(\text{typically in M} = \frac{mol}{L},\, \mu M = 10^{-6}\frac{mol}{L},\, \text{or nM} = 10^{-9}\frac{mol}{L}\right).$$

the lung-to-plasma partition coefficient $K_{p,ti}$ (typically unitless0, and the local concentration of the active ingredient 32 in the systemic blood circulation 5 $C_{sys}$ (typically in $$M = \frac{mol}{L}, \mu M = 10^{-6}\frac{mol}{L}, \text{ or } nM = 10^{-9}\frac{mol}{L}\Big).$$

Herein, "local" refers to one or more of: in the alveolar region, in the conducting airway region, or at a certain generational depth x. In this preferred, the at least one absorption parameter Spar includes the local perfusion/blood flow Q, the blood-to-plasma ratio in the lung BP, and the lung-to-plasma partition coefficient $K_{p,tis}$. The at least one efficacy parameter Epar may include the local concentration of the active ingredient 32 in the lung tissue 6 $C_{tis}$ (also denoted as Cval1, Cval2, Cval3) and/or the local concentration of the active ingredient 32 in the systemic blood circulation 5 $C_{sys}$.

In other embodiments, the computational absorption model Amod may also model the drug absorption process directly on the full (global) spatial particle deposition distribution Ddist, i.e. without using averaged (reduced) sub-domain-specific particle deposition distributions.

FIG. 13 illustrates a method for assessing the efficacy of an aerosol 3 for pulmonary drug delivery using the computational absorption model Amod. A particle deposition distribution Ddist is obtained using the method illustrated in FIG. 1 (see previous steps in FIG. 1 denoted by " . . . " in FIG. 13). At least one absorption value Sval of at least one absorption parameter Spar characterizing the absorption characteristic of aerosol 3 in the lungs 42 is determined and used in deter-mining at least one value Eval, Eval 1, Eval 2 of one or more efficacy parameter Epar. In the embodiment shown in FIG. 13, the efficacy parameter Epar is a time-dependent spatial concentration distribution Cdist (t) of an active ingredient 32 of the orally inhaled and/or nasal drug product 1 in the lung tissue 6. The efficacy values Eval, Eval1, Eval2 are time-dependent concentration values Cval1 (*t*), Cval2 (*t*), Cval3 (*t*) of the active ingredient (32) in different subdomains Lung-subd1, Lungsubd2, Lungsubd3 of the lung tissue 6. A first time-dependent concentration value Cval1 (*t*) of the active ingredient 32 in the lung tissue 6 in a first region (Lungsubd1) of the discretized respiratory-system structure 4' is different from a second time-dependent concentration value Cval2 (*t*) of the active ingredi-ent 32 in the lung tissue 6 in a second region (Lungsubd2) of the discretized res-piratory-system structure 4'.

In a first exemplary application of the method, efficacy of pulmonary drug delivery can be assessed (predicted) for a patient suffering from a lung disease that affects the lung tissue based on a spatial concentration distribution Cdist of the active ingredient 32 in the lung tissue 6, because the lung tissue 6 is where the drug is to be delivered to obtain the maximum effect in treatment. In a second exemplary application of the method, efficacy of pulmonary drug delivery can be assessed (predicted) for a patient suffering from a disease affecting other parts of the body than the lungs (i.e. not a lung disease) based on a spatial concentration distribution Cdist of the active ingredient 32 in the blood circulation 5, because administering the drug via the lungs is a suitable (efficient) way of delivering the drug into the body (e.g. for example more efficient than via injection or transdermal therapy). In a third exemplary application of the method, a spatial concentration distribution Cdist of the active ingredient 32 can be used to assess (predict or monitor) toxicity levels (concentration peaks) of the drug in the lungs, in particular in the lung tissue 6 and/or the blood circulation 5.

In some embodiments, an efficacy value Eval may be a function of at least one other (postprocessed) efficacy value. Typical functions are the area-under-the-curve (AUC) of a time-resolved concentration, such as Cval1 (*t*), Cval2 (*t*), Cval3 (*t*) (in a defined time-interval; typically in nM·h), the maximum value of a time-resolved concentration $$\Big(\text{typically in } M = \frac{mol}{L}, \mu M = 10^{-6}\frac{mol}{L}, \text{ or } nM = 10^{-9}\frac{mol}{L}\Big),$$

the time to reach the maximum concentration after administration of the drug product 1 $T_{max}$ (typically in min), the peak-sharpness (fraction of maximum concentration to AUC) of a time-resolved concentration, and the (time-resolved) pulmonary retention of the active ingredient (typically in percent). An efficacy value Eval may be dose-normalized (divided by the mass of the administered dose).

20 Absorption values Sval of an efficacy parameter Spar may further be computed considering additional properties of the lung model Lmod. Examples for proper-ties of lung model Lmod that can be included in the computation of the at least one efficacy value Eval are (local) volume of pulmonary lining fluid 51, (local) volume of lung tissue 6 and/or (local) volume of blood to translate per-volume concentration values to absolute (molar) masses of the active ingredient in any one of the layers of the airway wall 50. An absorption value Sval may also be deter-mined based on a simulation result including, but not limited to, spatially dependent values for pressure P, blood flow rate Q, strain of the lung tissue 6 and/or surface-active factor of the alveoli surface. The at least one absorption value Sval may also be determined based on the spatially dependent result of a blood flow simulation.

Generally, the at least one efficacy parameter Epar can be: a global, local, or functional concentration of the active ingredient 32; a global, local, or functional area-under-the-curve (AUC) of the active ingredient's concentration; a global, local, or functional peak-sharpness (fraction of maximum concentration to AUC) of the concentration; a global, local, or functional lung retention of the active ingredient; a global, local, or functional lung selectivity (fraction of the pulmonary concentration to the systemic concentration) of the active ingredient 32. In this context, the term "global" refers to the whole lung, "local" refers to a parameter's value in a predetermined spatial area-of-interest (AOI) within the lungs 42 (sub-domains of interest), and "functional" refers to a parameter's value in a functional unit (FU) of the lung. A functional unit FU can be understood as a subdomain of the lungs 42 having a specific function. AOIs can be one or more of: left/right lung, selected lobe(s) of the lungs 42, areas classified as healthy/pathological, central/peripheral parts of the lungs 42, one or more of the anatomical lung entities shown in FIG. 2, or any combination thereof. For example, FUs can be one or more of: airways 40, pulmonary lining fluid 51, mucus, alveolar lining fluid, lung tissue 6, epithelium, interstitium, basement membrane, endothelium, systemic blood circulation 5, blood plasma, or any combination thereof. The at least one efficacy value Eval may be used to evaluate the efficacy and/or toxicity of the active ingredient 32.

The computational absorption model Amod may further consider at least one ab-sorption value Spar, which is a function of the spatial location of the particle 30' to be absorbed within the lung. An absorption value Sval can be determined depending on the spatial particle deposition distribution Ddist, in particular depending on subdomain-specific particle deposition distributions in a plurality of subdomains Lungsubd1, Lungsubd2, . . . , Lungsubdn of the discretized respiratory-sys-tem structure 4'. Absorption values Sval may be determined based on a spatially dependent pathological condition of the lung. A pathological condition of the lung can be understood as a predetermined pathological modification of at least one zone of the respiratory system 4 caused by a lung disease of the lung. For example, a pathological condition can be due to emphysema or fibrosis in a specific pathological region of the lungs of a patient. Examples for pathological lung conditions that can influence the absorption process are narrowing of airways 40 due to asthma, reduced mucociliary clearance in diseased airways or altered perfusion in diseased areas.

The computational absorption model Amod may be adapted for modeling chemical and/or biological dissolution of aerosols 3, which may include one or more inter-mediate substances. Amod may be adapted for modeling dissolution and absorption of lipid nanoparticles (LNP). The absorption model Amod may be capable of modeling perfusion mechanisms within the lung. Examples of efficacy values Eval obtained for different aerosol values Aval and respiration values Rval based in different patient-specific lung models Lmod according to the described method are summarized in the following tables of Examples 1 and 2.

EXAMPLE 1

For the first exemplary study, the mass median aerodynamic diameter of aerosol particles 30 of an aerosol 3 was selected as aerosol parameter Apar, with two different aerosol values Aval (3 μm and 6 μm, see left columns). Based on the computed spatial particle deposition distribution Ddist, efficacy values Eval (see right columns) of the following efficacy parameters Epar were computed:

The percentage of aerosol mass deposited in lung tissue as fraction of inhaled aerosol mass (Epar):

| Mass median aerodynamic diameter [μm] | Aerosol mass deposited in lung tissue as fraction of inhaled [%] |
|---|---|
| 3 | 52 |
| 6 | 30 |

The percentage of aerosol mass deposited in conducting airways as fraction of the inhaled aerosol mass (Epar):

| Mass median aerodynamic diameter [μm] | Aerosol mass deposited in conducting airways as fraction of inhaled [%] |
|---|---|
| 3 | 21 |
| 6 | 26 |

The percentage of aerosol mass deposited per airway generation as fraction of the deposited aerosol mass (Epar). It can be derived that the remainder of the deposited aerosol mass has been delivered to airway generations higher than 16, particularly to the level or the alveoli 49 and/or into the blood circulation 5.

| Mass median aerodynamic diameter [μm] | Aerosol mass deposited per airway generation as fraction of deposited [%] | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 3 | 1.6 | 1.5 | 1.8 | 2.9 | 1.5 | 0.8 | 2.0 | 1.7 | 1.1 | 1.1 | 0.7 | 1.7 | 1.0 | 1.9 | 1.6 | 0.3 |
| 6 | 4.2 | 3.7 | 3.6 | 3.4 | 3.8 | 2.8 | 2.8 | 1.4 | 1.7 | 1.3 | 1.6 | 2.1 | 0.8 | 1.5 | 1.4 | 1.5 |

The percentage of aerosol mass deposited in the lung as a fraction of the inhaled aerosol mass (Epar):

| Mass median aerodynamic diameter [μm] | Aerosol mass deposited in lung as fraction of inhaled [%] |
|---|---|
| 3 | 73 |
| 6 | 56 |

The ratio between central and peripheral deposition (Epar), wherein "central" refers to a central area of the lung, whereas "peripheral" refers to the area of the portion of the lung around the outer boundary of the central area. With respect to the structure of the airways, the central area mostly comprises lower generations of the conductive airways (i.e. rather large airways), whereas the peripheral area mostly comprises the remaining higher generations (i.e. the smaller airways):

| Mass median aerodynamic diameter [μm] | Central/peripheral ratio [—] |
|---|---|
| 3 | 0.2 |
| 6 | 0.25 |

The percentage of aerosol mass deposited per lobe as fraction of the deposited aerosol mass (Epar), e.g. in the upper lobe of the left lung 42 (left upper):

| Mass median aerodynamic diameter [μm] | Aerosol mass deposited per lobe as fraction of deposited [%] | | | | |
|---|---|---|---|---|---|
| | Left upper | Left lower | Right lower | Right middle | Right upper |
| 3 | 19 | 24 | 26 | 8 | 16 |
| 6 | 17 | 23 | 26 | 6 | 12 |

The average deposited mass concentration in the lung [μg/ml] (Epar):

| Mass median aerodynamic diameter [μm] | Average deposited mass concentration in lung [μg/ml] |
|---|---|
| 3 | 1.0 |
| 6 | 3.6 |

EXAMPLE 2

In a second exemplary study, the tidal volume of the lung [ml] was selected as a respiration parameter Rpar with two different respiration values Rval (600 ml and 1000 ml). Based on the computed spatial particle deposition distribution Ddist for a determined aerosol parameter Apar and aerosol value Aval (e.g. Apar: mass median aerodynamic diameter, Aval: 3 μm), efficacy values Eval (see right columns) of the following efficacy parameters Epar were computed depending on two different respiration values Rval (see left column):

The percentage of aerosol mass deposited in lung tissue as fraction of inhaled aerosol mass (Epar):

| Tidal volume [ml] | Aerosol mass deposited in lung tissue as fraction of inhaled [%] |
|---|---|
| 600 | 54 |
| 1000 | 60 |

The percentage of aerosol mass deposited in conducting airways as fraction of the inhaled aerosol mass (Epar):

| Tidal volume [ml] | Aerosol mass deposited in conducting airways as fraction of inhaled [%] |
|---|---|
| 600 | 23 |
| 1000 | 23 |

The percentage of aerosol mass deposited per airway generation as fraction of the deposited aerosol mass (Epar):

| Tidal volume [ml] | Aerosol mass deposited per airway generation as fraction of deposited [%] | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 600 | 1.5 | 2.8 | 1.9 | 2.3 | 2.3 | 1.2 | 1.9 | 1.2 | 0.7 | 0.6 | 1.0 | 1.3 | 1.7 | 0.8 | 1.6 | 0.9 |
| 1000 | 1.5 | 2.3 | 2.3 | 2.5 | 2.1 | 1.1 | 1.5 | 1.0 | 0.9 | 0.8 | 1.4 | 1.4 | 1.7 | 0.9 | 1.6 | 1.1 |

The percentage of aerosol mass deposited in the lung as a fraction of the inhaled aerosol mass (Epar):

| Tidal volume [ml] | Aerosol mass deposited in lung as fraction of inhaled [%] |
|---|---|
| 600 | 77 |
| 1000 | 83 |

The ratio between central and peripheral deposition (Epar):

| Tidal volume [ml] | Central/peripheral ratio [—] |
|---|---|
| 600 | 0.23 |
| 1000 | 0.2 |

The percentage of aerosol mass deposited per lobe as fraction of the deposited aerosol mass (Epar):

| Tidal volume [ml] | Aerosol mass deposited per lobe as fraction of deposited [%] | | | | |
|---|---|---|---|---|---|
| | Left upper | Left lower | Right lower | Right middle | Right upper |
| 600 | 30 | 25 | 29 | 18 | 22 |
| 1000 | 25 | 23 | 28 | 19 | 21 |

The average deposited mass concentration in the lung [μg/ml] (Epar):

| Tidal volume [ml] | Average deposited mass concentration in lung [μg/ml] |
|---|---|
| 600 | 0.67 |
| 1000 | 1.2 |

The experiments show that the efficacy for pulmonary drug delivery can be assessed accurately, in particular locally throughout the lung. Moreover, the efficacy of drug delivery to a specific predetermined target area in the lung can be assessed accurately.

LIST OF REFERENCE NUMERALS

1 drug product
2 inhaler device
2a dry powder inhaler device
2b metered-dose inhaler device
2c nebulizer inhaler device (soft-mist inhaler device)
2d inhaler device including a ventilation tubing
3 aerosol
4 respiratory system
4' discretized structure of the respiratory system
5 blood circulation
6 lung tissue
7 inhaler/drug combination product
8 thorax
20, 20' mouthpiece
21 canister
22 nozzle
23 aerosol generation chamber
24 ventilation tubing
24a first inlet
24b second inlet
24c outlet
25 nebulizer device 26 propellant
27 actuator
28 actuator seat
29 valve
30 aerosol particle
30' discrete particle
31 carrier gas
40 airways
40' airway segment
40a' upstream airway segment
40b', 40c' downstream airway segment
41 mouth
42 lungs
43 diaphragm
44 pharynx
45 larynx
46 trachea
47 bronchi
48 bronchioles
49 alveoli
50, 50' airway wall
51 pulmonary lining fluid
52 mucociliary clearance
53 dissolution of active ingredient in pulmonary lining fluid
54 absorption of active ingredient in lung tissue
55 disposition of active ingredient into blood circulation
60 lever
61, 62 spring
63 vane
64 activation mechanism
70 metering mechanism
71 actuator cap
80 mesh
81 baffle
82 gas jet
83 vibrating component
Img tomographic image
Apar aerosol parameter
Epar efficacy parameter
Dopar inhaler operation parameter
Ddpar inhaler design parameter
Rpar respiration parameter
Aval aerosol value of the aerosol parameter
Eval efficacy value of the efficacy parameter
Eval_min minimum value of the efficacy parameter
Eval_max maximum value of the efficacy parameter
Rval respiration value of the respiration parameter
Ddist spatial particle deposition distribution
Dval deposition distance
Wval wall distance value
Gvel gas flow velocity
Pvel particle transport velocity vector
Velprof velocity profile
Gf gravitational force
Df flow resistance force (drag)
Bf buoyancy force
BMf Brownian motion force
Mmod computational mouth model
Lmod computational lung model
Pmod computational particle transport and deposition model
Amod computational absorption model
Dmod computational inhaler device model
$Lib_{Bifurc}$ airway bifurcation library
$Bifurc_1$, $Bifurc_2$, $Bifurc_3$, . . . . $Bifurc_r$ pre-computed airway bifurcation scenario
$Dsub1$, $Dsub2$, . . . , $Dsubn$ dose of the active ingredient
$Lungsubd1$, $Lungsubd2$, . . . . $Lungsubdn$ lung subdomain
Centcomp central compartment
$Pcomp1$, $Pcomp2$ peripheral compartment
Muccl mucociliary clearance
$tMuccl$, $tsub1$, $tsub2$ absorption half-live
$CLdcomp1$, $CLdcomp2$, CL clearance

The invention claimed is:

1. A method for assessing efficacy of an aerosol for pulmonary drug delivery, wherein the aerosol comprises aerosol particles containing an orally and/or nasally inhaled drug product, comprising:
determining at least one aerosol value of at least one aerosol parameter characterizing the aerosol;
determining a computational lung model representing a structure of a respiratory system and transient gas flow in airways of the respiratory system at least between trachea and lungs, the transient gas flow being modeled during inhalation and/or exhalation;
determining a computational particle transport and deposition model representing transient transport of individual aerosol particles in the transient gas flow in the airways and deposition of the individual aerosol particles in the respiratory system;
determining a spatial particle deposition distribution of a plurality of discrete particles representing the aerosol particles of the aerosol deposited in the structure of the respiratory system based on the at least one aerosol value using the computational lung model and the computational particle transport and deposition model; and
determining at least one efficacy value of an efficacy parameter indicating efficacy of pulmonary drug delivery of the aerosol based on the spatial particle deposition distribution.

2. The method of claim 1, further comprising:
using the at least one efficacy value for automatically assessing the efficacy for pulmonary drug delivery, storing the at least one efficacy value in a storage device, displaying the at least one efficacy value using a display device and/or transmitting the at least one efficacy value for use in assessing the efficacy for pulmonary drug delivery.

3. The method of claim 1, the computational lung model being based on a discretized respiratory-system structure derived from processed image data representing at least one respiratory system.

4. The method of claim 1, the computational lung model being based on a discretized respiratory-system structure derived from processed image data of a single tomographic image of at least one respiratory system.

5. The method of claim 1,
wherein the at least one aerosol parameter is indicative of one or more of:
a particle size,
a particle size distribution,
a particle density,
a particle shape,
an aerosol flow,
a flow velocity of the aerosol,
a type of carrier gas, and
a pressure of a carrier gas of the aerosol.

6. The method of claim 1, wherein the at least one aerosol value is determined by:
measuring the at least one aerosol value,
obtaining the at least one aerosol value from a database containing data indicating physical properties of the aerosol,
obtaining or deriving the at least one aerosol value from specification data of an inhaler device,
determining the at least one aerosol value based on analytical relations of physical properties of the aerosol, and/or
determining the at least one aerosol value, as a result of a computational simulation of a generation process and/or flow of the aerosol, in an inhaler device.

7. The method of claim 1, further comprising:
determining at least one respiration value of a respiration parameter characterizing respiration of the respiratory system, the respiratory system comprising spontaneous breathing, assisted spontaneous breathing and/or artificial respiration, wherein the at least one respiration value defines a boundary condition of the computational lung model,
wherein the respiration parameter is one or more of:
a time-dependent pressure difference between a pleural space and the trachea,
a time-dependent inhalation and/or exhalation gas flow,
a minimum and/or maximum lung pressure value and a respiration cycle frequency value, for pressure-controlled artificial respiration, and
an inhalation and/or exhalation gas volume for volume-controlled artificial respiration.

8. The method of claim 1,
wherein the computational lung model is based on:
a discretized individual respiratory-system structure derived from processed image data representing an individual respiratory system, or
a discretized averaged respiratory-system structure derived from processed image data representing an average of a plurality of respiratory systems.

9. The method of claim 1,
wherein the computational lung model is based on a discretized respiratory-system structure derived from processed image data representing at least one healthy respiratory system and at least one predetermined pathological image-data pattern representing a pathological modification of at least one zone of the respiratory system caused by a lung disease.

10. The method of claim 1,
wherein the computational particle transport and deposition model implements a Lagrangian approach to individually tracking each of the plurality of discrete particles transported in the transient gas flow, based on modelling at least one physical force acting on each of the plurality of discrete particles, the at least one physical force comprising a gravitational force, a flow resistance force, a buoyancy force, and/or a Brownian motion force,
wherein a direction of the gravitational force in the computational particle transport and deposition model is set depending on a spatial orientation of the respiratory system represented by processed image data.

11. The method of claim 3,
wherein a discretized particle transport velocity field, within a spatially three-dimensional airway segment, has a higher spatial dimension than a discretized gas flow velocity field within the spatially three-dimensional airway segment, and
wherein a three-dimensional discretized particle transport velocity field within a spatially three-dimensional airway segment is determined based on a constant discretized gas flow velocity within the spatially three-dimensional airway segment,
at least within a part of the discretized respiratory-system structure, within airway segments belonging to at least a second generation of the airways represented by the computational lung model.

12. The method of claim 1,
wherein the computational particle transport and deposition model individually tracks each of the plurality of discrete particles within a spatially three-dimensional airway segment by applying a particle transport velocity vector as a velocity of a particle,
wherein the particle transport velocity vector is determined based on a predetermined three-dimensional velocity profile across a cross-section of the spatially three-dimensional airway segment and a gas flow velocity obtained from the computational lung model for the spatially three-dimensional airway segment.

13. The method of claim 3, further comprising:
individually seeding each of the plurality of discrete particles into the transient gas flow in the airways by:
assigning a seeding location in an inflow cross-section of the discretized respiratory-system structure to each of the plurality of discrete particles, and/or
assigning a seeding time to each of the plurality of discrete particles based on a determined aerosol flow relative to a respiration cycle,
wherein individually seeding each of the plurality of discrete particles further comprises assigning one or more of a seeding velocity, seeding acceleration, particle density, particle size, particle shape, particle mass and drag coefficient to each-of the plurality of discrete particles,
wherein the seeding location assigned to each of the plurality of discrete particles is determined based on:
obtaining or deriving a statistical spatial distribution of the aerosol particles in the aerosol,
determining a particle location of each of the plurality of discrete particles in a computational simulation of a generation process and/or flow of the aerosol in an inhaler device, and/or
measuring a spatial distribution of the aerosol particles in the aerosol.

14. The method of claim 1,
wherein determining the at least one aerosol value uses a computational inhaler device model representing flow of the aerosol in an inhaler device,
wherein the computational inhaler device model represents at least one component of the inhaler device characterized by at least one device design parameter,
wherein the at least one device design parameter is indicative of one or more of:
a shape of a mouth piece and/or ventilation tubing of the inhaler device,
a diameter and/or shape of a nozzle of the inhaler device,
a flow channel geometry from an outlet of an aerosol generation and/or aerosol storage chamber to an outlet, and
a volume and/or geometry of a canister.

15. The method of claim 1,
wherein the efficacy parameter is indicative of one or more of:
an effective dose, a density of deposited aerosol particles, and
a concentration of an active ingredient of the orally and/or nasally inhaled drug product.

16. The method of claim 1,
wherein the aerosol particles contain a predetermined dose of an active ingredient of the orally and/or nasally inhaled drug product,
wherein the efficacy parameter corresponds to a blood concentration of the active ingredient in blood, and/or
wherein the efficacy parameter corresponds to a tissue concentration of the active ingredient in lung tissue.

17. The method of claim 1, further comprising:
determining, as the efficacy parameter, at least one value of a blood concentration using a computational absorption model representing absorption of an active ingredient contained in the aerosol particles in blood circulation, and/or
determining, as the efficacy parameter, at least one value of a tissue concentration using a computational absorption model representing absorption of the active ingredient contained in the aerosol particles into lung tissue.

18. The method of claim 1,
wherein the efficacy parameter is indicative of a time-dependent, spatial concentration distribution of an active ingredient of the orally and/or nasally inhaled drug product in a lung tissue of the respiratory system and/or in a blood circulation,
wherein the at least one efficacy value is at least one, time-dependent, concentration value of the active ingredient in the lung tissue and/or in the blood circulation.

19. The method of claim 3,
wherein the spatial particle deposition distribution comprises subdomain-specific particle deposition distributions in a plurality of subdomains of the discretized respiratory-system structure, and
wherein the at least one efficacy value of the efficacy parameter is determined depending on at least one of the subdomain-specific particle deposition distributions.

20. The method of claim 19,
wherein each subdomain represents:
a healthy region or a pathological region of the respiratory system, and/or
at least a part of the airways, the part of the airways comprising a specific generation of the airways, and/or of alveoli, and/or
a specific lobe of the lungs.

21. The method of claim 1, further comprising:
determining a predetermined minimum efficacy value of the efficacy parameter;
adapting the at least one aerosol value to generate an adapted aerosol value, and repeatedly performing steps of the method, until the at least one efficacy value determined is equal to or larger than the predetermined minimum efficacy value; and
outputting the adapted aerosol value to a display device and/or providing the adapted aerosol value for use in assessing the efficacy for pulmonary drug delivery as an optimized aerosol value of the at least one aerosol parameter.

22. The method of claim 1,
wherein the at least one aerosol value, if the at least one efficacy value is equal to or larger than a predetermined minimum efficacy value of the efficacy parameter and lower than a predetermined maximum efficacy value of the efficacy parameter, is used for one or more of:
generating the aerosol comprising the aerosol particles containing the orally and/or nasally inhaled drug product, wherein the aerosol generated is characterized by the at least one aerosol value,
setting a device operation parameter of an inhaler device such that the inhaler device generates an aerosol characterized by the at least one aerosol value, and
determining parameters for the inhaler device configured to generate the aerosol characterized by the at least one aerosol value.

23. The method of claim 1,
wherein the at least one efficacy value, if the at least one efficacy value is larger than a predetermined minimum efficacy value of the efficacy parameter and lower than a predetermined maximum efficacy value of the efficacy parameter, is used for one or more of:
assessing performance of an inhaler device for pulmonary drug delivery by determining an effect of a setting of a device operation parameter and/or the effect of a device design parameter of the inhaler device on the performance for pulmonary drug delivery, wherein the inhaler device is configured, when operated with a predetermined setting of a device operation parameter, to generate the aerosol for pulmonary drug delivery such that the aerosol is characterized by the at least one aerosol value of the at least one aerosol parameter,
assessing efficacy and/or safety of a dose of an active ingredient of an orally and/or nasally inhaled drug product, for pulmonary drug delivery, wherein the orally and/or nasally inhaled drug product is prepared to be administered as the aerosol, using an inhaler device, characterized by the at least one aerosol value of the at least one aerosol parameter, and
assessing efficacy of a drug/device combination product of an orally and/or nasally inhaled drug product and an inhaler device for pulmonary drug delivery, wherein the orally and/or nasally inhaled drug product is prepared to be administered as an aerosol characterized by the at least one aerosol value using the inhaler device, when operated with a predetermined setting of a device operation parameter, and the inhaler device is configured, when operated with a predetermined setting of a device operation parameter, to generate an aerosol characterized by the at least one aerosol value of the at least one aerosol parameter.

24. The method of claim 1, further comprising:
providing an orally and/or nasally inhaled drug product, based on an efficacy assessment, if the at least one efficacy value exceeds a first predetermined threshold value of the efficacy parameter;
providing an inhaler device, based on the efficacy assessment, if the at least one efficacy value exceeds a second predetermined threshold value of the efficacy parameter;
supplying the orally and/or nasally inhaled drug product to the inhaler device; and
operating the inhaler device, if the at least one efficacy value is equal to or larger than a predetermined minimum efficacy value of the efficacy parameter, such that the inhaler device generates the aerosol characterized by the at least one aerosol value of the at least one aerosol parameter.

25. The method of claim 1, further comprising:
determining at least one value of a device design parameter characterizing an inhaler device; and
designing and/or producing an inhaler device, based on an efficacy assessment, if the at least one efficacy value is equal to or larger than a predetermined minimum efficacy value of the efficacy parameter, such that the inhaler device implements a chosen value of the device design parameter.

26. The method of claim 25, wherein the inhaler device comprises a ventilation tubing for administering orally and/or nasally inhaled drug products to mechanically ventilated patients, and wherein the ventilation tubing comprises a first inlet for an aerosol flow and a second inlet for a ventilation gas flow generated by a ventilation device and a common outlet for the aerosol flow and the ventilation gas flow.

27. The method of claim 1, further comprising:
determining a particle size characterizing a dry powder as the at least one-aerosol value; and
producing an orally and/or nasally inhaled drug product, based on an efficacy assessment of the aerosol characterized by the at least one aerosol value, if the at least one efficacy value is equal to or larger than a predetermined minimum efficacy value of the efficacy parameter, such that the orally and/or nasally inhaled drug product is prepared to be administered, using an inhaler device, as the aerosol characterized by the at least one aerosol value of the at least one aerosol parameter.

28. A system, comprising:

at least one memory storing instructions; and at least one processor operatively connected to the at least one memory, and configured to execute the instructions to perform operations, comprising:

determining at least one aerosol value of at least one aerosol parameter characterizing an aerosol;

determining a computational lung model representing a structure of a respiratory system and transient gas flow in airways of the respiratory system at least between trachea and lungs, the transient gas flow being modeled during inhalation and/or exhalation;

determining a computational particle transport and deposition model representing transient transport of individual aerosol particles in the transient gas flow in the airways and deposition of the individual aerosol particles in the respiratory system;

determining a spatial particle deposition distribution of a plurality of discrete particles representing aerosol particles of the aerosol deposited in the structure of the respiratory system based on the at least one aerosol value using the computational lung model and the computational particle transport and deposition model; and determining at least one efficacy value of an efficacy parameter indicating efficacy of pulmonary drug delivery of the aerosol based on the spatial particle deposition distribution.

29. A non-transitory computer-readable storage medium encoded with computer readable instructions, which, when executed by a processor of a computing system, executes operations comprising:

determining at least one aerosol value of at least one aerosol parameter characterizing an aerosol;

determining a computational lung model representing a structure of a respiratory system and transient gas flow in airways of the respiratory system at least between trachea and lungs, the transient gas flow being modeled during inhalation and/or exhalation;

determining a computational particle transport and deposition model representing transient transport of individual aerosol particles in the transient gas flow in the airways and deposition of the individual aerosol particles in the respiratory system;

determining a spatial particle deposition distribution of a plurality of discrete particles representing aerosol particles of the aerosol deposited in the structure of the respiratory system based on the at least one aerosol value using the computational lung model and the computational particle transport and deposition model; and determining at least one efficacy value of an efficacy parameter indicating efficacy of pulmonary drug delivery of the aerosol based on the spatial particle deposition distribution.

30. A drug/device combination product comprising an inhaler device and orally and/or nasally inhaled drug product, the orally and/or nasally inhaled drug product having been determined at least in part by operations comprising:

determining at least one aerosol value of at least one aerosol parameter characterizing an aerosol;

determining a computational lung model representing a structure of a respiratory system and transient gas flow in airways of the respiratory system at least between trachea and lungs, the transient gas flow being modeled during inhalation and/or exhalation;

determining a computational particle transport and deposition model representing transient transport of individual aerosol particles in the transient gas flow in the airways and deposition of the individual aerosol particles in the respiratory system;

determining a spatial particle deposition distribution of a plurality of discrete particles representing aerosol particles of the aerosol deposited in the structure of the respiratory system based on the at least one aerosol value using the computational lung model and the computational particle transport and deposition model; and determining at least one efficacy value of an efficacy parameter indicating efficacy of pulmonary drug delivery of the aerosol based on the spatial particle deposition distribution.

31. A system, comprising:

at least one memory storing instructions; and at least one processor operatively connected to the at least one memory, and configured to execute the instructions to perform operations, comprising:

determining at least one aerosol value of at least one aerosol parameter characterizing an aerosol;

determining a computational lung model representing a structure of a respiratory system and transient gas flow in airways of the respiratory system at least between trachea and lungs, the computational lung model being based on a discretized respiratory-system structure derived from processed image data of a single tomographic image of the respiratory system, and the transient gas flow being modeled during inhalation and/or exhalation;

determining a computational particle transport and deposition model representing transient transport of individual aerosol particles in the transient gas flow in the airways and deposition of the individual aerosol particles in the respiratory system; and determining a spatial particle deposition distribution of a plurality of discrete particles representing aerosol particles of the aerosol deposited in the structure of the respiratory system based on the at least one aerosol value using the computational lung model and the computational particle transport and deposition model.

32. A system, comprising:
at least one memory storing instructions; and
at least one processor operatively connected to the at least one memory, and configured to execute the instructions to perform operations, comprising:
  determining at least one aerosol value of at least one aerosol parameter characterizing an aerosol;
  determining a computational lung model representing a structure of a respiratory system and transient gas flow in airways of the respiratory system at least between trachea and lungs, wherein the computational lung model is based on:
    a discretized individual respiratory-system structure derived from processed image data representing an individual respiratory system, or
    a discretized averaged respiratory-system structure derived from processed image data representing an average of a plurality of respiratory systems, and
  wherein the transient gas flow is modeled during inhalation and/or exhalation;
  determining a computational particle transport and deposition model representing transient transport of individual aerosol particles in the transient gas flow in the airways and deposition of the individual aerosol particles in the respiratory system; and
  determining a spatial particle deposition distribution of a plurality of discrete particles representing aerosol particles of the aerosol deposited in the structure of the respiratory system based on the at least one aerosol value using the computational lung model and the computational particle transport and deposition model.

33. A system, comprising:
at least one memory storing instructions; and
at least one processor operatively connected to the at least one memory, and configured to execute the instructions to perform operations, comprising:
  determining at least one aerosol value of at least one aerosol parameter characterizing an aerosol;
  determining a computational lung model representing a structure of a respiratory system and transient gas flow in airways of the respiratory system at least between trachea and lungs, wherein the computational lung model is based on a discretized respiratory-system structure derived from processed image data representing at least one healthy respiratory system and at least one predetermined pathological image-data pattern representing a pathological modification of at least one zone of the respiratory system caused by a lung disease, and wherein the transient gas flow is modeled during inhalation and/or exhalation;
  determining a computational particle transport and deposition model representing transient transport of individual aerosol particles in the transient gas flow in the airways and deposition of the individual aerosol particles in the respiratory system; and
  determining a spatial particle deposition distribution of a plurality of discrete particles representing aerosol particles of the aerosol deposited in the structure of the respiratory system based on the at least one aerosol value using the computational lung model and the computational particle transport and deposition model.

34. A system, comprising:
at least one memory storing instructions; and
at least one processor operatively connected to the at least one memory, and configured to execute the instructions to perform operations, comprising:
  determining at least one aerosol value of at least one aerosol parameter characterizing an aerosol, the at least one aerosol value determined using a computational inhaler device model representing flow of the aerosol in an inhaler device, wherein the computational inhaler device model represents at least one component of the inhaler device characterized by at least one device design parameter, and wherein the at least one device design parameter is indicative of one or more of:
    a shape of a mouth piece and/or ventilation tubing of the inhaler device,
    a diameter and/or shape of a nozzle of the inhaler device,
    a flow channel geometry from an outlet of an aerosol generation and/or aerosol storage chamber to an outlet, and
    a volume and/or geometry of a canister;
  determining a computational lung model representing a structure of a respiratory system and transient gas flow in airways of the respiratory system at least between trachea and lungs, the transient gas flow being modeled during inhalation and/or exhalation;
  determining a computational particle transport and deposition model representing transient transport of individual aerosol particles in the transient gas flow in the airways and deposition of the individual aerosol particles in the respiratory system; and
  determining a spatial particle deposition distribution of a plurality of discrete particles representing aerosol particles of the aerosol deposited in the structure of the respiratory system based on the at least one aerosol value using the computational lung model and the computational particle transport and deposition model.

* * * * *